United States Patent
Thum et al.

(10) Patent No.: US 11,685,905 B2
(45) Date of Patent: Jun. 27, 2023

(54) RHAMNOLIPID-PRODUCING CELL HAVING REDUCED GLUCOSE DEHYDROGENASE ACTIVITY

(71) Applicant: Evonik Operations GmbH, Essen (DE)

(72) Inventors: Oliver Thum, Ratingen (DE); Steffen Schaffer, Herten (DE); Christoph Schorsch, Frankfurt am Main (DE); Mirja Wessel, Bochum (DE)

(73) Assignee: Evonik Operations GmbH, Essen (DE)

( * ) Notice: Subject to any disclaimer, the term of this patent is extended or adjusted under 35 U.S.C. 154(b) by 477 days.

(21) Appl. No.: 16/333,719

(22) PCT Filed: Oct. 18, 2017

(86) PCT No.: PCT/EP2017/076620
§ 371 (c)(1),
(2) Date: Mar. 15, 2019

(87) PCT Pub. No.: WO2018/077700
PCT Pub. Date: May 3, 2018

(65) Prior Publication Data
US 2019/0271020 A1    Sep. 5, 2019

(30) Foreign Application Priority Data

Oct. 24, 2016 (EP) .................................... 16195194

(51) Int. Cl.
| *C12N 9/04* | (2006.01) |
| *C12P 19/44* | (2006.01) |
| *C12N 15/78* | (2006.01) |
| *C12N 15/52* | (2006.01) |

(52) U.S. Cl.
CPC ............ *C12N 9/0006* (2013.01); *C12N 15/52* (2013.01); *C12N 15/78* (2013.01); *C12P 19/44* (2013.01); *C12Y 101/05002* (2013.01)

(58) Field of Classification Search
CPC ............................... C12N 9/0006; C12P 19/44
See application file for complete search history.

(56) References Cited

U.S. PATENT DOCUMENTS

| 6,013,494 A | 1/2000 | Schaffer et al. |
| 6,136,576 A | 10/2000 | Diaz-Torres et al. |
| 8,911,982 B2 | 12/2014 | Schaffer et al. |
| 9,005,928 B2 | 4/2015 | Schaffer et al. |
| 9,068,211 B2 | 6/2015 | Schaffer et al. |
| 9,085,787 B2 | 7/2015 | Schaffer et al. |
| 9,102,968 B2 | 8/2015 | Schaffer et al. |
| 9,157,108 B2 | 10/2015 | Schaffer et al. |
| 9,243,212 B2 | 1/2016 | Kuppert et al. |
| 9,580,720 B2 | 2/2017 | Schaffer et al. |
| 10,174,353 B2 | 1/2019 | Thum et al. |
| 2014/0148588 A1 | 5/2014 | Schilling et al. |
| 2014/0296168 A1 | 10/2014 | Schilling et al. |

FOREIGN PATENT DOCUMENTS

| DE | 100 31 999 A1 | 4/2001 | |
| DE | 10 2012 201 360 A1 | 8/2013 | |
| WO | WO-2015180907 A1 * | 12/2015 | ............. A01N 25/30 |
| WO | 2018/077700 A1 | 5/2018 | |
| WO | 2018/077701 A1 | 5/2018 | |

OTHER PUBLICATIONS

Poblete-Castro. In-silico-driven metabolic engineering of Pseudomonas putida for enhanced production of poly-hydroxyalkanoates. Metabolic Engineering 15 (2013) 113-123.*
Q88MX4. UniProtKB/TrEMBL Database. 2015.*
Soberon-Chavez. Production of rhamnolipids by Pseudomonas aeruginosa. Appl. Microbiol. Biotechnol (2005) 68: 718-725.*
Dobler et al., "Rhamnolipids in Perspective: Gene Regulatory Pathways, Metabolic Engineering, Production and Technological Forecasting," copyright Jan. 2016, New Biotechnology, See Abstract, vol. 33, No. 1, pp. 123-135 (1 page).
International Search Report dated Apr. 18, 2018 in PCT/EP2017/076620 (5 pages).
Lovaglio et al., "Rahmnolipids Know-How: Looking for Strategies for Its Industrial Dissemination," copyright Sep. 2015, Biotechnology Advances, Elsevier Publishing, Barking, GB, See Abstract, vol. 33, No. 8, pp. 1715-1726 (1 page).
Shigematsu et al., "Cellulose Production From Glucose Using a Glucose Dehydrogenase Gene (GDH)-Deficient Mutant of Gluconacetobacter Xylinus and Its Use for Bioconversion of Sweet Potato Pulp," copyright Apr. 2005, Journal of Bioscience and Bioengineering, Elsevier, Amsterdam, NL, See Abstract, vol. 99, No. 4, pp. 415-422 (1 page).
Tiso et al., "Creating Metabolic Demand as an Engineering Strategy in Pseudomonas Putida—Rhamnolipid Synthesis as an Example," copyright Aug. 2016, Metabolic Engineering Communications, vol. 3, pp. 234-244 (11 pages).
Wittgens et al., "Growth Independent Rhamnolipid Production From Glucose Using the Non-Pathogenic Pseudomonas Putida KT2440," copyright Oct. 2011, Microbial Cell Factories, Biomed Central, GB, vol. 10, No. 1 (18 pages).
Written Opinion dated Apr. 18, 2018 in PCT/EP2017/076620 (7 pages).
Sage et al., "Hexose Phosphate Metabolism and Exopolysaccharide Formation in Psuedomonas cepacia," copyright 1990, Current Microbiology, vol. 20, pp. 191-198 (7 pages).

\* cited by examiner

*Primary Examiner* — Yong D Pak
(74) *Attorney, Agent, or Firm* — Grüneberg and Myers PLLC

(57) ABSTRACT

The invention relates to cells which make rhamnolipids and are genetically modified such that they have a decreased activity, compared to the wild type thereof, of a glucose dehydrogenase and to a method for producing rhamnolipids using the cells according to the invention.

8 Claims, 1 Drawing Sheet
Specification includes a Sequence Listing.

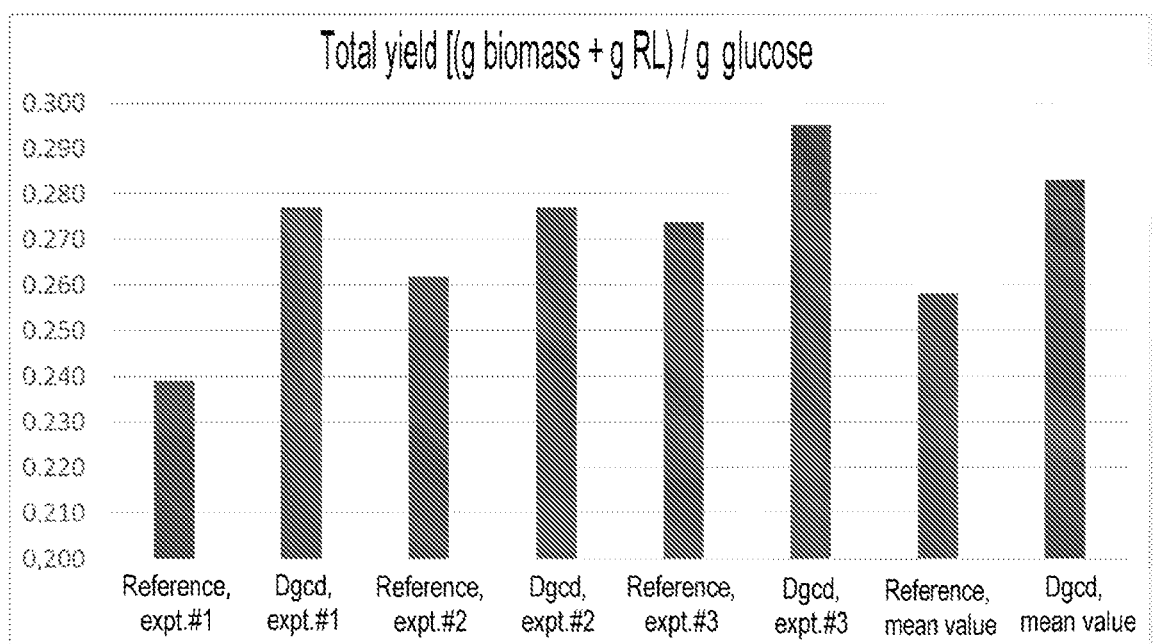

RHAMNOLIPID-PRODUCING CELL HAVING REDUCED GLUCOSE DEHYDROGENASE ACTIVITY

CROSS REFERENCE TO RELATED APPLICATIONS

This application is a 35 U.S.C. § 371 U.S. national phase entry of International Application No. PCT/EP2017/076620 having an international filing date of Oct. 18, 2017, which claims the benefit of European Application No. 16195194.2 filed Oct. 24, 2016, each of which is incorporated herein by reference in its entirety.

FIELD

The invention relates to cells which make rhamnolipids and are genetically modified such that they have a decreased activity, compared to the wild type thereof, of a glucose dehydrogenase and to a method for producing rhamnolipids using the cells according to the invention.

BACKGROUND

DE102012201360 describes cells which make rhamnolipids and are genetically modified such that they have decreased or increased activities, compared to the wild type thereof, of certain enzymes and enzyme combinations, meaning that the cells advantageously produce rhamnolipids, and a method for producing rhamnolipids using the cells according to the invention.

SUMMARY

It is an object of the invention to provide cells having an increased yield of rhamnolipids on the basis of the carbon source used.

DETAILED DESCRIPTION

It was found that, surprisingly, the cells described below are able to achieve the aforementioned object.

The invention provides cells which make rhamnolipids and are genetically modified such that they have a decreased activity, compared to the wild type thereof, of a glucose dehydrogenase. The invention further provides a method for producing rhamnolipids using the aforementioned cells as biocatalyst.

One advantage of the present invention is that it is possible to use organisms which are not pathogenic and are easy to culture.

Another advantage of the present invention is that it is possible to make use of a large selection of carbon sources.

A further advantage is that it is not necessary in all circumstances to use oils as sole substrate or as co-substrate.

Another advantage is that it is possible with the aid of the invention to produce rhamnolipids having defined and modulatable properties.

A further advantage is that it is possible to produce rhamnolipids with higher space-time and carbon yields than with cells with no change in these activities.

The present invention therefore provides a cell, preferably an isolated cell able to make at least one rhamnolipid, characterized in that it has been genetically modified such that it, compared to the wild type thereof, has a decreased activity of at least one enzyme $E_1$, which catalyses the conversion of D-glucose and quinone to D-glucono-1,5-lactone and quinol.

The term "wild type" of a cell denotes here a cell whose genome is present in a state as has arisen naturally by evolution. The term is used both for the whole cell and for individual genes. The term "wild type", therefore, particularly does not include those cells or genes whose gene sequences have been at least partially modified by man by means of recombinant techniques. The term "wild type" denotes in particular the phenotype, the genotype or the gene that occurs most frequently in numbers in a natural population of organisms.

In the context of the present invention, the term "rhamnolipid" is understood to mean a compound of the general formula (I) or the salt thereof,

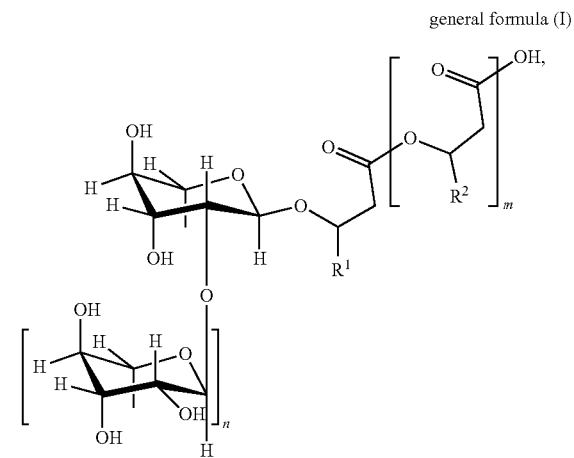

general formula (I)

where m=2, 1 or 0, in particular 1 or 0, n=1 or 0, in particular 1, $R^1$=organic radical having 2 to 24, preferably 5 to 13, carbon atoms, in particular optionally branched, optionally substituted, in particular hydroxy-substituted, optionally unsaturated, in particular optionally mono-, bi- or tri-unsaturated, alkyl radical, preferably one selected from the group consisting of pentenyl, heptenyl, nonenyl, undecenyl and tridecenyl and $(CH_2)_o$—$CH_3$ where o=1 to 23, preferably 4 to 12, and $R^2$=independently of one another, identical or different, organic radical having 2 to 24, preferably 5 to 13, carbon atoms, in particular optionally branched, optionally substituted, in particular hydroxy-substituted, optionally unsaturated, in particular optionally mono-, bi- or tri-unsaturated, alkyl radical, preferably one selected from the group consisting of pentenyl, heptenyl, nonenyl, undecenyl and tridecenyl and $(CH_2)_o$—$CH_3$ where o=1 to 23, preferably 4 to 12.

If the cell according to the invention is able to make a rhamnolipid where m=1, it is preferred that the radical determined via $R^1$ and $R^2$ is

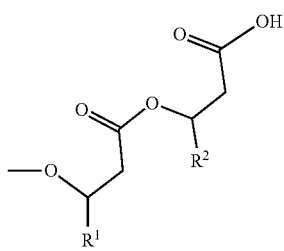

derived from 3-hydroxyoctanoyl-3-hydroxyoctanoic acid, 3-hydroxyoctanoyl-3-hydroxydecanoic acid, 3-hydroxydecanoyl-3-hydroxyoctanoic acid, 3-hydroxyoctanoyl-3-hydroxydecenoic acid, 3-hydroxydecenoyl-3-hydroxyoctanoic acid, 3-hydroxyoctanoyl-3-hydroxydodecanoic acid, 3-hydroxydodecanoyl-3-hydroxyoctanoic acid, 3-hydroxyoctanoyl-3-hydroxydodecenoic acid, 3-hydroxydodecenoyl-3-hydroxyoctanoic acid, 3-hydroxydecanoyl-3-hydroxydecanoic acid, 3-hydroxydecanoyl-3-hydroxydecenoic acid, 3-hydroxydecenoyl-3-hydroxydecanoic acid, 3-hydroxydecanoyl-3-hydroxydecenoic acid, 3-hydroxydecenoyl-3-hydroxydodecanoic acid, 3-hydroxydodecanoyl-3-hydroxydecanoic acid, 3-hydroxydodecanoyl-3-hydroxydecenoic acid, 3-hydroxydecenoyl-3-hydroxydodecenoic acid, 3-hydroxytetradecenoyl-3-hydroxytetradecenoic acid, 3-hydroxytetradecanoyl-3-hydroxydecenoic acid, 3-hydroxydodecenoyl-3-hydroxydecanoic acid, 3-hydroxydecanoyl-3-hydroxytetradecanoic acid, 3-hydroxytetradecanoyl-3-hydroxydecanoic acid, 3-hydroxydecanoyl-3-hydroxytetradecenoic acid, 3-hydroxytetradecenoyl-3-hydroxydecanoic acid, 3-hydroxydecanoyl-3-hydroxydodecanoic acid, 3-hydroxydodecanoyl-3-hydroxydodecenoic acid, 3-hydroxydodecanoyl-3-hydroxydodecanoic acid, 3-hydroxydodecenoyl-3-hydroxydodecanoic acid, 3-hydroxytetradecanoyl-3-hydroxytetradecanoic acid, 3-hydroxydodecanoyl-3-hydroxytetradecanoic acid, 3-hydroxytetradecanoyl-3-hydroxyhexadecanoic acid, 3-hydroxytetradecanoyl-3-hydroxytetradecanoic acid, 3-hydroxyhexadecanoic acid or 3-hydroxyhexadecanoyl-3-hydroxyhexadecanoic acid.

It is evident to a person skilled in the art that a cell according to the invention is also able to make mixtures of various rhamnolipids of the general formula (I).

In this connection, it is preferred that the cells according to the invention are able to make mixtures of rhamnolipids of the general formula (I), characterized in that n=1 in more than 80% by weight, preferably more than 90% by weight, particularly preferably more than 95% by weight, of the rhamnolipids made and the radical determined via $R^1$ and $R^2$ is derived from 3-hydroxydecanoyl-3-hydroxyoctanoic acid or 3-hydroxyoctanoyl-3-hydroxydecanoic acid in less than 20% by weight, preferably less than 15% by weight, of the rhamnolipids made, the specified % by weight being based on the sum of all rhamnolipids of the general formula (I) made.

The accession numbers listed in the context of the present invention correspond to the protein bank database entries of the NCBI with a date of 26 Jan. 2016; generally, in the present case, the version number of the entry is identified by ".number" such as, for example, "0.1". Unless stated otherwise, all percentages (%) given are percentages by mass.

The expression "decreased activity of an enzyme Ex" used is accordingly understood to mean preferably activity decreased by a factor of at least 0.5, particularly preferably at least 0.1, further preferably at least 0.01, still further preferably at least 0.001 and most preferably at least 0.0001. The expression "decreased activity" also includes no detectable activity ("activity of zero").

Methods for decreasing enzymatic activities in microorganisms are known to a person skilled in the art. Molecular biology techniques in particular are useful here. For example, the activity of a certain enzyme can be decreased by targeted mutation or by other measures known to a person skilled in the art for decreasing the activity of a certain enzyme. Instructions for modifying and decreasing protein expression and associated enzyme activity decrease specifically for *Pseudomonas* and *Burkholderia*, in particular for interrupting specific genes, can be found by a person skilled in the art in, for example, Dubeau et al. 2009. BMC Microbiology 9:263; Singh & Röhm. Microbiology. 2008. 154:797-809 or Lee et al. FEMS Microbiol Lett. 2009. 297(1):38-48. The preferred ways of decreasing the enzymatic activity of the enzyme $E_1$ that are described below can similarly be preferably used for further enzyme activities to be decreased in the context of the present invention.

Cells preferred according to the invention are characterized in that the decrease in enzymatic activity is achieved by genetic modification of the gene encoding the enzyme $E_1$, said modification being selected from the group comprising, preferably consisting of, insertion of foreign DNA into the gene, deletion of at least parts of the gene, point mutations in the gene sequence, especially in or of regulatory sequences, such as, for instance, promoters and terminators or of ribosomal binding sites.

In this context, foreign DNA is understood to mean any DNA sequence which is "foreign" to the gene (and not to the organism), i.e. endogenous DNA sequences can also function as "foreign DNA" in this context. In this context, the gene is particularly preferably interrupted by insertion of a selection marker gene; the foreign DNA is therefore a selection marker gene, the insertion preferably having taken place by homologous recombination into the gene locus.

Cells alternatively preferred according to the invention are characterized in that the decrease in enzymatic activity is achieved by a targeted, transcriptional or post-transcriptional gene silencing of the gene encoding the enzyme $E_1$, especially with the aid of at least one repressor binding to the promoter of the gene encoding the enzyme $E_1$, by means of nonsense-mediated mRNA decay (NMD) and RNA interference (RNAi), with RNAi preferably making use of microRNA methodology (miRNA) or of the small interfering RNA method (siRNA), by means of which the mRNA of the enzyme $E_1$ is degraded.

According to the invention, it is preferred that $E_1$ is a glucose 1-dehydrogenase of EC 1.1.5.2. Particularly preferred enzymes $E_1$ are selected from enzymes encoded by a gcd gene and also enzymes having a polypeptide sequence in which up to 25%, preferably up to 20%, particularly preferably up to 15%, in particular up to 10, 9, 8, 7, 6, 5, 4, 3, 2, 1%, of the amino acid residues are modified with respect to the enzymes encoded by a gcd gene by deletion, insertion, substitution or a combination thereof and which still has at least 10%, preferably 50%, particularly preferably 80%, in particular more than 90%, of the enzymatic activity of the enzyme having the reference sequence of the enzymes encoded by a gcd gene.

In particular, the enzymes $E_1$ are selected from enzymes $E_1$ having polypeptide sequence AAN67066.1 or having a polypeptide sequence in which up to 25%, preferably up to 20%, particularly preferably up to 15%, in particular up to 10, 9, 8, 7, 6, 5, 4, 3, 2, 1%, of the amino acid residues are modified with respect to AAN67066.1 by deletion, insertion, substitution or a combination thereof and which still has at least 10%, preferably 50%, particularly preferably 80%, in particular more than 90%, of the enzymatic activity of the enzyme having the reference sequence AAN67066.1.

The cells according to the invention can be prokaryotes or eukaryotes. They can be mammalian cells (such as human cells), plant cells or microorganisms such as yeasts, fungi or bacteria, with microorganisms being particularly preferred and bacteria and yeasts being most preferred. Furthermore, it is advantageous according to the invention when the cell according to the invention is a cell which, as wild type, is able to make polyhydroxyalkanoates having chain lengths of the monoalkanoate of from $C_6$ to $C_{16}$. Such cells are, for example, *Burkholderia* sp., *Burkholderia thailandensis*, *Pseudomonas* sp., *Pseudomonas putida*, *Pseudomonas aeruginosa*, *Pseudomonas oleovorans*, *Pseudomonas chlororaphis*, *Pseudomonas stutzeri*, *Pseudomonas fluorescens*, *Pseudomonas citronellolis*, *Pseudomonas resinovorans*, *Comamonas testosteroni*, *Aeromonas hydrophila*, *Cupriavidus necator*, *Alcaligenes latus* and *Ralstonia eutropha*. In this context, preferred inventive cells are genetically modified such that they, compared to the wild type thereof, are able to make fewer polyhydroxyalkanoates.

Within the bacteria group, particular preference is given to, in particular, *Pseudomonas putida*, *Escherichia coli* and *Burkholderia thailandensis*.

The starting strains of the cells according to the invention can be natural rhamnolipid producers, those cells which already produce rhamnolipids as wild type, or cells in which rhamnolipid production has only been made possible by gene technology.

In both cases, cells preferred according to the invention benefit from the fact that they have been genetically modified such that they, compared to the wild type thereof, have an increased activity of at least one of the enzymes selected from the group $E_2$, $E_3$ and $E_4$, the enzyme $E_2$ being able to catalyse the conversion of 3-hydroxyalkanoyl-ACP via 3-hydroxyalkanoyl-3-hydroxyalkanoic acid-ACP to hydroxyalkanoyl-3-hydroxyalkanoic acid, the enzyme $E_3$ being a rhamnosyltransferase I and being able to catalyse the conversion of dTDP-rhamnose and 3-hydroxyalkanoyl-3-hydroxyalkanoate to α-L-rhamnopyranosyl-3-hydroxyalkanoyl-3-hydroxyalkanoate, and the enzyme $E_4$ being a rhamnosyltransferase II and being able to catalyse the conversion of dTDP-rhamnose and α-L-rhamnopyranosyl-3-hydroxyalkanoyl-3-hydroxyalkanoate to α-L-rhamnopyranosyl-(1-2)-α-L-rhamnopyranosyl-3-hydroxyalkanoyl-3-hydroxyalkanoate.

Enzyme $E_2$ is preferably selected from enzymes which are encoded by an rhlA gene and also enzymes having a polypeptide sequence in which up to 25%, preferably up to 20%, particularly preferably up to 15%, in particular up to 10, 9, 8, 7, 6, 5, 4, 3, 2, 1%, of the amino acid residues are modified with respect to the enzymes encoded by an rhlA gene by deletion, insertion, substitution or a combination thereof and which still has at least 10%, preferably 50%, particularly preferably 80%, in particular more than 90%, of the enzymatic activity of the enzyme having the reference sequence of the enzymes encoded by an rhlA gene.

Enzyme $E_3$ is preferably selected from enzymes which are encoded by an rhlB gene and also enzymes having a polypeptide sequence in which up to 25%, preferably up to 20%, particularly preferably up to 15%, in particular up to 10, 9, 8, 7, 6, 5, 4, 3, 2, 1%, of the amino acid residues are modified with respect to the enzymes encoded by an rhlB gene by deletion, insertion, substitution or a combination thereof and which still has at least 10%, preferably 50%, particularly preferably 80%, in particular more than 90%, of the enzymatic activity of the enzyme having the reference sequence of the enzymes encoded by an rhlB gene.

Enzyme $E_4$ is preferably selected from enzymes which are encoded by an rhlC gene and also enzymes having a polypeptide sequence in which up to 25%, preferably up to 20%, particularly preferably up to 15%, in particular up to 10, 9, 8, 7, 6, 5, 4, 3, 2, 1%, of the amino acid residues are modified with respect to the enzymes encoded by an rhlC gene by deletion, insertion, substitution or a combination thereof and which still has at least 10%, preferably 50%, particularly preferably 80%, in particular more than 90%, of the enzymatic activity of the enzyme having the reference sequence of the enzymes encoded by an rhlC gene.

What is particularly preferred for $E_2$, $E_3$ and $E_4$:
enzyme $E_2$ is selected from the group consisting of,
at least one enzyme $E_{2a}$ having polypeptide sequence ADP06387.1, or having a polypeptide sequence in which up to 25%, preferably up to 20%, particularly preferably up to 15%, in particular up to 10, 9, 8, 7, 6, 5, 4, 3, 2, 1%, of the amino acid residues are modified with respect to the reference sequence ADP06387.1 by deletion, insertion, substitution or a combination thereof and which still has at least 10%, preferably 50%, particularly preferably 80%, in particular more than 90%, of the enzymatic activity of the enzyme having the reference sequence ADP06387.1, enzymatic activity for an enzyme $E_{2a}$ being understood to mean the ability to convert 3-hydroxydecanoyl-ACP via 3-hydroxydecanoyl-3-hydroxydecanoic acid-ACP to hydroxydecanoyl-3-hydroxydecanoic acid,
at least one enzyme $E_{2b}$ having polypeptide sequence AIP29471.1, CBI71021.1, NP_252169.1, ABR81106.1, YP_439272.1, YP_111362.1, YP_110557.1, YP_105231.1, ZP_02461688.1, ZP_02358949.1, ZP_01769192.1, ZP_04893165.1, ZP_02265387.2, ZP_02511781.1, ZP_03456835.1, ZP_03794633.1, YP_990329.1, ZP_02408727.1, YP_002908243.1, ZP_04884056.1, YP_004348703.1, ZP_04905334.1, ZP_02376540.1, EGC99875.1, ZP_02907621.1, YP_001811696.1, ZP_02466678.1, ZP_02891475.1, YP_776393.1, YP_002234939.1, YP_001778804.1, YP_371314.1, ZP_04943305.1, YP_623139.1, ZP_02417235.1 or ZP_04892059.1 or having a polypeptide sequence in which up to 25%, preferably up to 20%, particularly preferably up to 15%, in particular up to 10, 9, 8, 7, 6, 5, 4, 3, 2, 1%, of the amino acid residues are modified with respect to the particular aforementioned accession number by deletion, insertion, substitution or a combination thereof and which still has at least 10%, preferably 50%, particularly preferably 80%, in particular more than 90%, of the enzymatic activity of the enzyme having the particular aforementioned accession number, enzymatic activity for an enzyme $E_{2b}$ being understood to mean the ability to convert 3-hydroxytetradecanoyl-ACP via 3-hydroxytetradecanoyl-3-hydroxytetradecanoic acid-ACP to hydroxytetradecanoyl-3-hydroxytetradecanoic acid,
enzyme $E_3$ is selected from the group consisting of,
at least one enzyme $E_3$a having polypeptide sequence ADP06388.1, YP_001347032.1, CBI71029.1, YP_002439138.1, CBI71031.1, NP 252168.1, CBI71034.1, CBI71028.1, AAA62129.1 or ZP_04929750.1 or having a polypeptide sequence in which up to 25%, preferably up to 20%, particularly preferably up to 15%, in particular up to 10, 9, 8, 7, 6, 5, 4, 3, 2, 1%, of the amino acid residues are modified with respect to the particular aforementioned accession number by deletion, insertion, substitution or a combination thereof and which still has at least 10%, preferably 50%, particularly preferably 80%, in particular more than 90%, of the enzymatic activity of the enzyme having the particular aforementioned accession number, enzymatic activity for an enzyme $E_3a$ being understood to mean the ability to convert dTDP-rhamnose and 3-hydroxydecanoyl-3-hydroxydecanoic acid to α-L-rhamnopyranosyl-3-hydroxydecanoyl-3-hydroxydecanoic acid, at least one enzyme $E_3b$ having polypeptide sequence AJY01590.1, ABR84881.1, NP_252168.1, FN601364.1, YP_440074.1, ZP_05590657.1, ZP_04520374.1, ZP_00438360.2, ZP00438209.2, YP_001074761.1, ZP_04811084.1, YP_110558.1, YP_111361.1, ZP_02492857.1, YP_337246.1, YP_001061811.1, YP_105607.1, ZP_02371503.1, ZP_02503962.1, ZP_03456839.1, ZP_02461690.1, ZP_03794634.1, ZP_01769736.1, ZP01769308.1, ZP_02358948.1, ZP_02487736.1, ZP_02408758.1, YP_002234937.1, ZP_02891477.1, YP_001778806.1, YP_623141.1, YP_838721.1, ZP_04943307.1, YP_776391.1, YP_004348704.1, ZP_02907619.1, YP_371316.1, ZP_02389948.1, YP_001811694.1, YP_002908244.1, ZP_02511808.1, ZP_02376542.1, EGC99877.1, ZP_02451760.1 or ZP_02414414.1 or having a polypeptide sequence in which up to 25%, preferably up to 20%, particularly preferably up to 15%, in particular up to 10, 9, 8, 7, 6, 5, 4, 3, 2, 1%, of the amino acid residues are modified with respect to the particular aforementioned accession number by deletion, insertion, substitution or a combination thereof and which still has at least 10%, preferably 50%, particularly preferably 80%, in particular more than 90%, of the enzymatic activity of the enzyme having the particular aforementioned accession number, enzymatic activity for an enzyme $E_3b$ being understood to mean the ability to convert dTDP-rhamnose and 3-hydroxytetradecanoyl-3-hydroxytetradecanoic acid to α-L-rhamnopyranosyl-3-hydroxytetradecanoyl-3-hydroxytetradecanoic acid, and enzyme $E_4$ is selected from the group consisting of, at least one enzyme $E_4a$ having polypeptide sequence NP_249821.1 or having a polypeptide sequence in which up to 25%, preferably up to 20%, particularly preferably up to 15%, in particular up to 10, 9, 8, 7, 6, 5, 4, 3, 2, 1%, of the amino acid residues are modified with respect to the reference sequence NP_249821.1 by deletion, insertion, substitution or a combination thereof and which still has at least 10%, preferably 50%, particularly preferably 80%, in particular more than 90%, of the enzymatic activity of the enzyme having the reference sequence NP_249821.1, enzymatic activity for an enzyme $E_4a$ being understood to mean the ability to convert dTDP-rhamnose and α-L-rhamnopyranosyl-3-hydroxydecanoyl-3-hydroxydecanoic acid to α-L-rhamnopyranosyl-(1-2)-α-L-rhamnopyranosyl-3-hydroxydecanoyl-3-hydroxydecanoic acid, at least one enzyme $E_4b$ having polypeptide sequence AJY02981.1, FN601387.1, FN601391.1 YP_440071.1, ZP_02375899.1, ZP_02466676.1, YP_001075863.1, ZP_02408796.1, YP_335530.1, ZP_01769176.1, YP_105609.1, ZP_01770867.1, ZP_04520873.1, YP_110560.1, YP_001024014.1, ZP_03450125.1, YP_001061813.1, YP_111359.1, ZP_00440994.2, ZP_03456926.1, ZP_02358946.1, ZP_00438001.2, ZP_02461478.1, ZP_02503929.1, ZP_02511832.1, YP_004348706.1, ZP_04898742.1, YP_002908246.1, ZP02382844.1, EGD05167.1, YP_001778808.1, YP_001811692.1, YP_002234935.1, YP_371318.1, YP_623143.1, YP_776389.1, ZP_02891479.1, ZP_02907617.1, ZP_02417424.1 or ZP_04898743.1 or having a polypeptide sequence in which up to 25%, preferably up to 20%, particularly preferably up to 15%, in particular up to 10, 9, 8, 7, 6, 5, 4, 3, 2, 1%, of the amino acid residues are modified with respect to the particular aforementioned accession number by deletion, insertion, substitution or a combination thereof and which still has at least 10%, preferably 50%, particularly preferably 80%, in particular more than 90%, of the enzymatic activity of the enzyme having the aforementioned accession number, enzymatic activity for an enzyme $E_4b$ being understood to mean the ability to convert dTDP-rhamnose and α-L-rhamnopyranosyl-3-hydroxytetradecanoyl-3-hydroxytetradecanoic acid to α-L-rhamnopyranosyl-(1-2)-α-L-rhamnopyranosyl-3-hydroxytetradecanoyl-3-hydroxytetradecanoic acid.

It is clear that the activities specifically indicated above for the enzymes $E_{2a}$ to $E_4b$ are only a specific exemplary selection of a broader activity spectrum of the aforementioned enzymes; the activity mentioned in each case is that for which a reliable measurement method is available for a given enzyme. Thus, it is clear that an enzyme which converts a substrate having an unbranched, saturated $C_{10}$-alkyl radical will likewise convert—although possibly with reduced activity—those substrates having a $C_6$- or $C_{16}$-alkyl radical, which may possibly also be branched or unsaturated.

Cells preferred according to the invention are able, as wild type, to make no quantities or no detectable quantities of rhamnolipids and, furthermore, preferably have, as wild type, no activity or no detectable activity of the enzymes $E_2$, $E_3$ and $E_4$.

According to the invention, preference is given to cells which have increased activities of the following enzyme combinations:

$E_2$, $E_3$, $E_4$, $E_2E_3$, $E_2E_4$, $E_3E_4$ and $E_2E_3E_4$, of which the combination $E_3$, $E_3E_4$ and $E_2E_3E_4$, in particular $E_2E_3E_4$ is particularly preferred.

In a preferred embodiment of the cell according to the invention having an increased activity of the enzyme combination $E_2E_3E_4$, n is preferably =1.

In the context of the present invention, the term "increased activity of an enzyme" is preferably to be understood to mean an increased intracellular activity.

In principle, an increase in the enzymatic activity can be achieved by increasing the copy number of the gene sequence(s) coding for the enzyme, by using a strong promoter or an improved ribosome binding site, by attenuating negative regulation of gene expression, for example using transcription regulators, or by enhancing positive regulation of gene expression, for example using transcription regulators, by altering the codon usage of the gene, by increasing in various ways the half-life of the mRNA or of the enzyme, by modifying the regulation of expression of the gene or by using a gene or allele coding for a corresponding enzyme with increased activity and by combining these measures as appropriate. The increase in the activity is preferably increased according to the invention by increasing the copy number of the gene sequence, which codes for the enzyme, in comparison to the wild type. The incorporation of a copy of a gene sequence, which was not previously present in the wild type, self-evidently corresponds to an increase in the copy number from 0 to 1.

Cells genetically modified according to the invention are generated, for example, by transformation, transduction, conjugation, or a combination of these methods, with a vector containing the desired gene, an allele of this gene or parts thereof and optionally a promoter enabling the gene to be expressed. Heterologous expression is achieved in particular by integrating the gene or alleles into the chromosome of the cell or an extrachromosomally replicating vector.

An overview of the options for increasing enzyme activity in cells is given for pyruvate carboxylase by way of example in DE-A-100 31 999, which is hereby incorporated by way of reference and whose disclosure forms part of the disclosure of the present invention regarding the options for increasing enzyme activity in cells.

Expression of the enzymes or genes specified above and all enzymes or genes specified below is detectable with the aid of 1- and 2-dimensional protein gel separation and subsequent optical identification of the protein concentration in the gel using appropriate evaluation software. If the increase in an enzyme activity is based exclusively on an increase in expression of the corresponding gene, the increase in said enzyme activity can be quantified in a simple manner by comparing the 1- or 2-dimensional protein separations between wild type and genetically modified cell. A customary method of preparing protein gels in the case of coryneform bacteria and of identifying said proteins is the procedure described by Hermann et al. (Electrophoresis, 22: 1712.23 (2001)). Protein concentration can likewise be analysed by Western blot hybridization using an antibody specific for the protein to be detected (Sambrook et al., Molecular Cloning: a laboratory manual, 2nd Ed. Cold Spring Harbor Laboratory Press, Cold Spring Harbor, N.Y. USA, 1989) and subsequent optical evaluation using appropriate software for determination of concentration (Lohaus and Meyer (1989) Biospektrum, 5: 32-39; Lottspeich (1999) Angewandte Chemie 111: 2630-2647). The activity of DNA-binding proteins can be measured by means of DNA band shift assays (also referred to as gel retardation) (Wilson et al. (2001) Journal of Bacteriology, 183: 2151-2155). The effect of DNA-binding proteins on the expression of other genes can be detected by various well-described reporter gene assay methods (Sambrook et al., Molecular Cloning: a laboratory manual, 2nd Ed. Cold Spring Harbor Laboratory Press, Cold Spring Harbor, N.Y. USA, 1989). Intracellular enzymatic activities can be determined by various described methods (Donahue et al. (2000) Journal of Bacteriology 182 (19): 5624-5627; Ray et al. (2000) Journal of Bacteriology 182 (8): 2277-2284; Freedberg et al. (1973) Journal of Bacteriology 115 (3): 816-823). If no specific methods for determining the activity of a particular enzyme are stated in the explanations below, the increase in enzyme activity and also the decrease in an enzyme activity are preferably determined by means of the methods described in Hermann et al., Electophoresis, 22: 1712-23 (2001), Lohaus et al., Biospektrum 5 32-39 (1998), Lottspeich, Angewandte Chemie 111: 2630-2647 (1999) and Wilson et al., Journal of Bacteriology 183: 2151-2155 (2001).

If the increase in the enzyme activity is accomplished by mutation of the endogenous gene, such mutations can either be generated in a non-directed manner according to classical methods, for example by UV radiation or by chemicals which cause mutation, or specifically by means of genetic engineering methods such as deletion(s), insertion(s) and/or nucleotide substitution(s). Modified cells are obtained by these mutations. Particularly preferred mutants of enzymes are also particularly those enzymes which are no longer subject to feedback, product or substrate inhibition, or at least less so compared to the wild type enzyme.

If the increase in the enzyme activity is accomplished by increasing the synthesis of an enzyme, the copy number of the relevant genes, for example, is increased or the promoter and regulatory region or the ribosomal binding site, which is located upstream of the structural gene, is mutated. Expression cassettes which are incorporated upstream of the structural gene have a similar effect. Additionally, by means of inducible promoters, it is possible to increase expression at any desired time. Furthermore, however, so-called "enhancers" can also be assigned to the enzyme gene as regulatory sequences, which likewise cause increased gene expression via improved interaction between RNA polymerase and DNA. Expression is also improved by measures to prolong the lifetime of the mRNA. Moreover, enzyme activity is also intensified by preventing the degradation of the enzyme protein. Here, the genes or gene constructs are present either in plasmids of different copy number or are integrated in the chromosome and amplified. Alternatively, moreover, overexpression of the relevant genes can be achieved by modification of the medium composition and culturing. Instructions in relation thereto can be found by a person skilled in the art in, inter alia, Martin et al. (Bio/Technology 5, 137-146 (1987)), in Guerrero et al. (Gene 138, 35-41 (1994)), Tsuchiya and Morinaga (Bio/Technology 6, 428-430 (1988)), in Eikmanns et al. (Gene 102, 93-98 (1991)), in EP-A-0 472 869, in U.S. Pat. No. 4,601,893, in Schwarzer and Puihler (Bio/Technology 9, 84-87 (1991)), in Reinscheid et al. (Applied and Environmental Microbiology 60, 126-132 (1994)), in LaBarre et al. (Journal of Bacteriology 175, 1001-1007 (1993)), in WO-A-96/15246, in Malumbres et al. (Gene 134, 15-24 (1993)), in JP-A-10-229891, in Jensen and Hammer (Biotechnology and Bioengineering 58, 191-195 (1998)) and in known genetics and molecular biology textbooks. The measures described above, like the mutations, also result in genetically modified cells.

To increase the expression of the particular genes, episomal plasmids, for example, are used. In principle, as plasmids or vectors, all embodiments available to those skilled in the art for this purpose are possible. Such plasmids and vectors can, for example, be inferred from the brochures of Novagen, Promega, New England Biolabs, Clontech or Gibco BRL. Further preferred plasmids and vectors can be found in: Glover, D. M. (1985) DNA cloning: a practical approach, Vol. I-III, IRL Press Ltd., Oxford; Rodriguez, R. L. and Denhardt, D. T (eds) (1988) Vectors: a survey of molecular cloning vectors and their uses, 179-204, Butterworth, Stoneham; Goeddel, D. V. (1990) Systems for heterologous gene expression, Methods Enzymol. 185, 3-7; Sambrook, J.; Fritsch, E. F. and Maniatis, T. (1989), Molecular cloning: a laboratory manual, 2nd ed., Cold Spring Harbor Laboratory Press, New York.

The plasmid vector which contains the gene to be amplified is then transferred into the desired strain by conjugation or transformation. The method of conjugation is described, for example, in Schafer et al., Applied and Environmental Microbiology 60: 756-759 (1994). Methods for transformation are described, for example, in Thierbach et al., Applied Microbiology and Biotechnology 29: 356-362 (1988), Dunican and Shivnan, Bio/Technology 7: 1067-1070 (1989) and Tauch et al., FEMS Microbiology Letters 123: 343-347 (1994). After homologous recombination by means of a "cross-over" event, the resulting strain comprises at least two copies of the gene concerned.

In the context of the present invention, the increase in the activity of an enzyme is achieved particularly preferably by an increase, compared to the wild-type cell, in the copy number of the region encoding the enzyme considered, especially in conjunction with a strong promoter, and, in the case of enzymes already present in the wild type, by using a stronger promoter compared to the one present in the wild-type gene.

The wording "an increased activity, compared to the wild type thereof, of an enzyme Ex" used above and in the explanations below should preferably always be understood to mean an activity of the particular enzyme Ex increased by a factor of at least 2, particularly preferably at least 10, further preferably at least 100, still further preferably at least 1000 and most preferably at least 10 000. Furthermore, the cell according to the invention which has "an increased activity, compared to the wild type thereof, of an enzyme Ex" in particular also includes a cell, the wild type of which has no or at least no detectable activity of this enzyme Ex, and which only displays detectable activity of this enzyme Ex after increasing the enzyme activity, for example, by overexpression. In this context, the term "overexpression" or the wording "increase in expression" used in the explanations below also includes the case that a starting cell, for example a wild-type cell, displays no or at least no detectable expression and detectable synthesis of the enzyme Ex is only induced by recombinant methods.

Modifications of amino acid residues of a given polypeptide sequence which do not lead to a significant change in the properties and the function of the given polypeptide are known to the person skilled in the art. Thus, it is possible, for example, to interchange conserved amino acids; examples of such suitable amino acid substitutions are: Ala with Ser; Arg with Lys; Asn with Gln or His; Asp with Glu; Cys with Ser; Gln with Asn; Glu with Asp; Gly with Pro; His with Asn or Gln; Ile with Leu or Val; Leu with Met or Val; Lys with Arg or Gln or Glu; Met with Leu or Ile; Phe with Met or Leu or Tyr; Ser with Thr; Thr with Ser; Trp with Tyr; Tyr with Trp or Phe; Val with Ile or Leu. It is also known that modifications in particular at the N or C terminus of a polypeptide in the form of, for example, amino acid insertions or deletions frequently do not have a significant influence on the function of the polypeptide.

The "amino acid identity" in connection with the enzymes used in the context of the invention is determined with the aid of known methods. In general, use is made of special computer programs with algorithms taking into account specific requirements.

Preferred methods for determining the identity initially generate the greatest alignment between the sequences to be compared. Computer programs for determining the identity include, but are not limited to, the GCG program package including
GAP (Deveroy, J. et al., Nucleic Acid Research 12 (1984), page 387), Genetics Computer Group University of Wisconsin, Medicine (Wi), and BLASTP, BLASTN and FASTA (Altschul, S. et al., Journal of Molecular Biology 215 (1990), pages 403-410). The BLAST program can be obtained from the National Center For Biotechnology Information (NCBI) and from other sources (BLAST Handbook, Altschul S. et al., NCBI NLM NIH Bethesda ND 22894; Altschul S. et al., above).

The known Smith-Waterman algorithm can likewise be used for determining the identities. Preferred parameters for determining the "amino acid identity" are, when using the BLASTP program (Altschul, S. et al., Journal of Molecular Biology 215 (1990), pages 403-410):

| Expect Threshold: | 10 |
|---|---|
| Word size: | 3 |
| Matrix: | BLOSUM62 |
| Gap costs: | Existence: 11; Extension: 1 |
| Compositional adjustments: | Conditional compositional score matrix adjustment |

The above parameters are the default parameters for amino acid sequence comparison. The GAP program is likewise suitable for use with the above parameters.

In the context of the present invention, an identity of 60% according to the above algorithm means 60% identity. The same applies to higher identities.

The activity of an enzyme can be determined by disrupting cells containing said activity in a manner known to a person skilled in the art, for example with the aid of a bead mill, a French press or an ultrasound disintegrator, and then removing intact cells, cell debris and disruption aids, such as glass beads for instance, by 10 minutes of centrifugation at 11 000×g and 4° C.

Using the resulting cell-free crude extract, it is then possible to carry out enzyme assays with subsequent LC-ESI-MS detection of the products. Alternatively, the enzyme can be enriched or else purified to homogeneity in a manner known to a person skilled in the art by chromatographic methods (such as nickel-nitrilotriacetic acid affinity chromatography, streptavidin affinity chromatography, gel-filtration chromatography or ion-exchange chromatography).

It is trivial and only mentioned for the sake of completeness that, to determine an activity increased or reduced compared to the wild type of a cell, a wild type reference culture is used which has been exposed to the same conditions as the sample to be determined.

The activity of an enzyme $E_1$ is determined using cell-free extracts with the aid of the Colorimetric Glucose Dehydrogenase Assay Kit from Abcam (Art. # ab102532) in accordance with the requirements of the manufacturer.

The activity of the enzyme $E_2$ is determined using the crude cell-free extracts obtained as described above, as follows: A standard assay contains 100 µM E. coli ACP, 1 mM β-mercaptoethanol, 200 µM malonyl-coenzyme A, 40 µM octanoyl-coenzyme A (for $E_{2a}$) or dodecanoyl-coenzyme A (for $E_{2b}$), 100 µM NADPH, 2 µg of E. coli FabD, 2 µg of Mycobacterium tuberculosis FabH, 1 µg of E. coli FabG, 0.1 M sodium phosphate buffer, pH 7.0, and 5 µg of enzyme $E_5$ in a final volume of 120 µL. ACP, β-mercaptoethanol and sodium phosphate buffer are pre-incubated at 37° C. for 30 min in order to reduce the ACP completely. The reaction is started by addition of enzyme $E_2$. The reactions are stopped using 2 ml of water which has been acidified to pH 2.0 using HCl and then extracted twice using 2 ml of chloroform/methanol (2:1 (v:v)). Phase separation is carried out by centrifugation (16 100 g, 5 min, RT). The lower organic phase is removed, fully evaporated in a vacuum centrifuge, and the sediment is taken up in 50 µl of methanol. Undissolved constituents are sedimented by centrifugation (16 100 g, 5 min, RT) and the sample analysed by means of LC-ESI-MS. The products are identified by analysis of the corresponding mass traces and of the $MS^2$ spectra.

The activity of the enzyme $E_3$ is then determined using the cell-free crude extracts obtained as described above, as follows: A standard assay can consist of 185 µl of 10 mM Tris-HCl (pH 7.5), 10 µl of 125 mM dTDP-rhamnose and 50 µl of crude protein extract (approximately 1 mg of total protein) or purified protein in solution (5 µg of purified protein). The reaction is started by the addition of 10 µl of 10 mM ethanolic solution of 3-hydroxydecanoyl-3-hydroxydecanoic acid (for $E_3a$) or 3-hydroxytetradecanoyl-3-hydroxytetradecanoic acid (for $E_3b$) and incubated at 30° C. for 1 h with shaking (600 rpm). The reaction is then admixed with 1 ml of acetone. Undissolved constituents are sedimented by centrifugation (16 100 g, 5 min, RT) and the sample analysed by means of LC-ESI-MS. The products are identified by analysis of the corresponding mass traces and of the $MS^2$ spectra.

The activity of the enzyme $E_4$ is then determined using the crude cell-free extracts obtained as described above, as follows: A standard assay can consist of 185 µl of 10 mM Tris-HCl (pH 7.5), 10 µl of 125 mM dTDP-rhamnose and 50 µl of crude protein extract (approximately 1 mg of total protein) or purified protein in solution (5 µg of purified protein). The reaction is started by the addition of 10 µl of 10 mM ethanolic solution of α-L-rhamnopyranosyl-3-hydroxydecanoyl-3-hydroxydecanoic acid (for $E_4a$) or α-L-rhamnopyranosyl-3-hydroxytetradecanoyl-3-hydroxytetradecanoic acid (for $E_4b$) and incubated at 30° C. for 1 h with shaking (600 rpm). The reaction is then admixed with 1 ml of acetone. Undissolved constituents are sedimented by centrifugation (16 100 g, 5 min, RT) and the sample analysed by means of LC-ESI-MS. The products are identified by analysis of the corresponding mass traces and of the $MS^2$ spectra.

It is advantageous when, additionally with respect to $E_1$, the cell according to the invention has been genetically modified such that it, compared to the wild type thereof, has an increased activity, as given in detail below, of at least one of the enzymes selected from the group consisting of at least one enzyme $E_5$, a dTTP:α-D-glucose-1-phosphate thymidylyltransferase, EC 2.7.7.24, particularly selected from enzymes encoded by an rmlA or rfbA gene or having a polypeptide sequence in which up to 25%, preferably up to 20%, particularly preferably up to 15%, in particular up to 10, 9, 8, 7, 6, 5, 4, 3, 2, 1%, of the amino acid residues of the enzymes encoded by an rmlA or rfbA gene are modified by deletion, insertion, substitution or a combination thereof and which still has at least 10%, preferably 50%, particularly preferably 80%, in particular more than 90%, of the enzymatic activity of the enzyme encoded by an rmlA or rfbA gene, enzymatic activity for an enzyme $E_5$ being understood to mean the ability to convert α-D-glucose 1-phosphate and dTTP to dTDP-glucose, at least one enzyme $E_6$, a dTDP-glucose 4,6-hydrolyase, EC 4.2.1.46, particularly selected from enzymes encoded by an rmlB or rfbB gene or having a polypeptide sequence in which up to 25%, preferably up to 20%, particularly preferably up to 15%, in particular up to 10, 9, 8, 7, 6, 5, 4, 3, 2, 1%, of the amino acid residues of the enzymes encoded by an rmlB or rfbB gene are modified by deletion, insertion, substitution or a combination thereof and which still has at least 10%, preferably 50%, particularly preferably 80%, in particular more than 90%, of the enzymatic activity of the enzyme encoded by an rmlB or rfbB gene, enzymatic activity for an enzyme $E_6$ being understood to mean the ability to convert dTDP-glucose to dTDP-4-dehydro-6-deoxy-D-glucose, at least one enzyme $E_7$, a dTDP-4-dehydrorhamnose 3,5-epimerase, EC 5.1.3.13, particularly selected from enzymes encoded by an rmlC or rfbC gene or having a polypeptide sequence in which up to 25%, preferably up to 20%, particularly preferably up to 15%, in particular up to 10, 9, 8, 7, 6, 5, 4, 3, 2, 1%, of the amino acid residues of the enzymes encoded by an rmlC or rfbC gene are modified by deletion, insertion, substitution or a combination thereof and which still has at least 10%, preferably 50%, particularly preferably 80%, in particular more than 90%, of the enzymatic activity of the enzyme encoded by an rmlC or rfbC gene, enzymatic activity for an enzyme $E_7$ being understood to mean the ability to convert dTDP-4-dehydro-6-deoxy-D-glucose to dTDP-4-dehydro-6-deoxy-L-mannose and at least one enzyme $E_8$, a dTDP-4-dehydrorhamnose reductase, EC 1.1.1.133, particularly selected from enzymes encoded by an rmlD or rfbD gene or having a polypeptide sequence in which up to 25%, preferably up to 20%, particularly preferably up to 15%, in particular up to 10, 9, 8, 7, 6, 5, 4, 3, 2, 1%, of the amino acid residues of the enzymes encoded by an rmlD or rfbD gene are modified by deletion, insertion, substitution or a combination thereof and which still has at least 10%, preferably 50%, particularly preferably 80%, in particular more than 90%, of the enzymatic activity of the enzyme encoded by an rmlD or rfbD gene, enzymatic activity for an enzyme $E_8$ being understood to mean the ability to convert dTDP-4-dehydro-6-deoxy-L-mannose to dTDP-6-deoxy-L-mannose.

The activity of the enzyme $E_5$ is determined using the samples obtained as described above for the enzymes $E_2$ to $E_4$, by incubating α-D-glucose 1-phosphate (1.3 mM) with dTTP (5 mM) and g of purified enzyme $E_5$ in 50 µl of sodium phosphate buffer, pH 8.5, and stopping the reaction after 5, 10 and 20 min of incubation at 30° C. by addition of 20 µl of chloroform. The mixture is then vortexed and centrifuged for 5 min at 16 000 g and room temperature. The aqueous phase is transferred to a new reaction tube and the organic phase re-extracted using 80 µl of water. Both aqueous phases are combined and analysed by HPLC. This involves using a Phenosphere ODS2 column (250×4.6 mm; Phenomenex, Torrance, USA) or a Spheresorb ODS2 column (250×4.6 mm; Waters, Milford, USA). The analytes are eluted using 0.5 M $KH_2PO_4$ (Eluent A) at a flow rate of 1 ml min$^{-1}$ for 15 min, followed by a linear gradient up to 80% Eluent A and 20% methanol over a period of 14 min at a flow rate of 0.7 ml min$^{-1}$. Analytes eluting from the ODS2 columns are then injected into a Phenosphere SAX ion-exchange column (250×4.6 mm; Phenomenex, Torrance, USA) and the analytes are eluted at a flow rate of 1 ml min$^{-1}$ and with a linear ammonium formate gradient (2 to 600 mM over 25 min). dTDP-glucose is then quantified via its UV absorption using a photodiode array detector (DAD). The absorption maximum of thymidine is 267 nm. Calibration is carried out using authentic nucleotide sugars (Sigma-Aldrich, St. Louis, USA).

The activity of the enzyme $E_6$ is then determined using the samples obtained as described above for the enzymes $E_2$ to $E_4$, by incubating dTDP-α-D-glucose (1.3 mM) with 5 µg of purified enzyme $E_6$ in 50 µl of sodium phosphate buffer, pH 8.5, and stopping the reaction after 5, 10 and 20 min of incubation at 30° C. by addition of 20 µl of chloroform. The mixture is then vortexed and centrifuged for 5 min at 16 000 g and room temperature. The aqueous phase is transferred to a new reaction tube and the organic phase re-extracted using 80 µl of water. Both aqueous phases are combined and analysed by HPLC. This involves using a Phenosphere ODS2 column (250×4.6 mm; Phenomenex, Torrance, USA) or a Spheresorb ODS2 column (250×4.6 mm; Waters, Milford, USA). The analytes are eluted using 0.5 M $KH_2PO_4$ (Eluent A) at a flow rate of 1 ml min$^{-1}$ for 15 min, followed by a linear gradient up to 80% Eluent A and 20% methanol over a period of 14 min at a flow rate of 0.7 ml min$^{-1}$. Analytes eluting from the ODS2 columns are then injected into a Phenosphere SAX ion-exchange column (250×4.6 mm; Phenomenex, Torrance, USA) and the analytes are eluted at a flow rate of 1 ml min$^{-1}$ and with a linear ammonium formate gradient (2 to 600 mM over 25 min).

dTDP-glucose and dTDP-4-dehydro-6-deoxy-D-glucose are then quantified via their UV absorption using a photodiode array detector (DAD). The absorption maximum of thymidine is 267 nm. Calibration is carried out using authentic nucleotide sugars (Sigma-Aldrich, St. Louis, USA).

The activity of the enzyme $E_7$ is then determined using the samples obtained as described above for the enzymes $E_2$ to $E_4$, by first incubating dTDP-α-D-glucose (1.3 mM) with 5 µg of purified enzyme $E_6$ in 50 µl of sodium phosphate buffer, pH 8.5, for 10 min at 30° C. Thereafter, 0.5 µg of purified enzyme $E_7$ is added, and the reaction is stopped after 5, 10 and 20 min of incubation at 30° C. by addition of 20 µl of chloroform. The mixture is then vortexed and centrifuged for 5 min at 16 000 g and room temperature. The aqueous phase is transferred to a new reaction tube and the organic phase re-extracted using 80 µl of water. Both aqueous phases are combined and analysed by HPLC. This involves using a Phenosphere ODS2 column (250×4.6 mm; Phenomenex, Torrance, USA) or a Spheresorb ODS2 column (250×4.6 mm; Waters, Milford, USA). The analytes are eluted using 0.5 M $KH_2PO_4$ (Eluent A) at a flow rate of 1 ml $min^{-1}$ for 15 min, followed by a linear gradient up to 80% Eluent A and 20% methanol over a period of 14 min at a flow rate of 0.7 ml $min^{-1}$. Analytes eluting from the ODS2 columns are then injected into a Phenosphere SAX ion-exchange column (250×4.6 mm; Phenomenex, Torrance, USA) and the analytes are eluted at a flow rate of 1 ml $min^{-1}$ and with a linear ammonium formate gradient (2 to 600 mM over 25 min). dTDP-glucose, dTDP-4-dehydro-6-deoxy-D-glucose and dTDP-6-deoxy-L-mannose are then quantified via their UV absorption using a photodiode array detector (DAD). The absorption maximum of thymidine is 267 nm. Calibration is carried out using authentic nucleotide sugars (Sigma-Aldrich, St. Louis, USA).

The activity of the enzyme $E_8$ is then determined using the samples obtained as described above for the enzymes $E_2$ to $E_4$, by first incubating dTDP-α-D-glucose (1.3 mM) with 5 µg of purified enzyme $E_6$ in 50 µl of sodium phosphate buffer, pH 8.5, for 10 min at 30° C. Thereafter, 5 µg of purified enzyme $E_7$ and 0.5 µg of purified enzyme $E_8$ and also NADPH (10 mM) are added, and the reaction is stopped after 5, 10 and 20 min of incubation at 30° C. by addition of 20 µl of chloroform. The mixture is then vortexed and centrifuged for 5 min at 16 000 g and room temperature. The aqueous phase is transferred to a new reaction tube and the organic phase re-extracted using 80 µl of water. Both aqueous phases are combined and analysed by HPLC. This involves using a Phenosphere ODS2 column (250×4.6 mm; Phenomenex, Torrance, USA) or a Spheresorb ODS2 column (250×4.6 mm; Waters, Milford, USA). The analytes are eluted using 0.5 M $KH_2PO_4$ (Eluent A) at a flow rate of 1 ml $min^{-1}$ for 15 min, followed by a linear gradient up to 80% Eluent A and 20% methanol over a period of 14 min at a flow rate of 0.7 ml $min^{-1}$. Analytes eluting from the ODS2 columns are then injected into a Phenosphere SAX ion-exchange column (250×4.6 mm; Phenomenex, Torrance, USA) and the analytes are eluted at a flow rate of 1 ml $min^{-1}$ and with a linear ammonium formate gradient (2 to 600 mM over 25 min). dTDP-glucose, dTDP-4-dehydro-6-deoxy-D-glucose, dTDP-6-deoxy-L-mannose and dTDP-4-dehydro-6-deoxy-L-mannose are then quantified via their UV absorption using a photodiode array detector (DAD). The absorption maximum of thymidine is 267 nm. Calibration is carried out using authentic nucleotide sugars (Sigma-Aldrich, St. Louis, USA).

According to the invention, preference is given to cells which have increased activities of the following enzyme combinations:

$E_5E_6$, $E_5E_7$, $E_5E_8$, $E_6E_7$, $E_6E_8$, $E_7E_8$, $E_5E_6E_7$, $E_5E_6E_8$, $E_6E_7E_8$, $E_5E_7E_8$, $E_5E_6E_7E_8$, of which the combination $E_5E_6E_7E_8$ is particularly preferred.

Particularly preferably, the increased activities of the aforementioned enzyme combinations can be combined with those of the above-described enzymes $E_2$ to $E_4$, wherein the combination $E_2E_3E_4E_5E_6E_7E_8$ is particularly preferred.

It is further advantageous and thus preferred when, additionally with respect to $E_1$, the cell according to the invention has been genetically modified such that it, compared to the wild type thereof, has an increased activity of at least one enzyme $E_9$, which is a glucose transporter. Particularly preferably, use is made here of glucose transporters that are foreign to the cell according to the invention, therefore those that are not present in the wild-type genome. Preferred enzymes $E_9$ are particularly selected from enzymes encoded by a galP, glf, iolT1, glcP, gluP, SemiSWEET or glcU gene and PTS systems (consisting of the components enzyme I, HPr, enzyme IIA, enzyme IIB and enzyme IIC, it being possible for enzymes IIA, IIB and IIC to be present as fusion proteins) or enzymes having a polypeptide sequence in which up to 25%, preferably up to 20%, particularly preferably up to 15%, in particular up to 10, 9, 8, 7, 6, 5, 4, 3, 2, 1%, of the amino acid residues of the galP, glf, iolT1, glcP, gluP, SemiSWEET or glcU gene-encoded enzymes and PTS systems are modified by deletion, insertion, substitution or a combination thereof and which still has at least 10%, preferably 50%, particularly preferably 80%, in particular more than 90%, of the enzymatic activity of the galP, glf, iolT1, glcP, gluP, SemiSWEET or glcU gene-encoded enzyme and PTS system, enzymatic activity for an enzyme $E_9$ being understood to mean the ability to get 2-(N-(7-nitrobenz-2-oxa-1,3-diazol-4-yl)amino)-2-deoxyglucose (2-NBDG) into the cell.

For the aforementioned polypeptide sequences, the iolT1 gene is especially that from *C. glutamicum*, the glcP gene is especially one from *M. smegmatis*, *S. frigidimarina* or *S. amazonensis*, the gluP gene is especially that from *B. abortus*, the SemiSWEET gene is that from *L. biflexa* and the glcU gene is especially one from *B. subtilis* or *S. xylosus*.

The activity of the enzyme $E_9$ can be determined with the aid of the Glucose Uptake Cell-Base Assay Kit, item No. 600470 from Cayman Chemicals, specifically in accordance with the manufacturer's instructions dated 9 Oct. 2015.

In conjunction with the increased activity of at least one enzyme $E_9$, it may be advantageous according to the invention and thus preferred when the cell according to the invention has, as wild type, an enzyme $E_{10}$, an ABC glucose transporter, and is characterized in that it has been genetically modified such that it, compared to the wild type thereof, has a decreased activity of the enzyme $E_{10}$, which gets 2-(N-(7-nitrobenz-2-oxa-1,3-diazol-4-yl)amino)-2-deoxyglucose (2-NBDG) into the cell. The activity of the enzyme $E_{10}$ can be determined as described above for $E_9$. It is clear to a reasonable person skilled in the art that, to this end, cells merely differing in the genetic modification directly directed towards the decrease in activity of $E_{10}$ are directly compared with one another in order to determine whether there is a difference in activity.

Particularly preferably, the modified activities of the aforementioned enzymes are in the combinations $E_2E_3E_4E_9E_{10}$, $E_5E_6E_7E_8E_9E_{10}$ and $E_2E_3E_4E_5E_6E_7E_8E_9E_{10}$, wherein $E_2E_3E_4E_5E_6E_7E_8E_9E_{10}$ is particularly preferred.

Furthermore, it is advantageous according to the invention when the cell according to the invention is a cell which, as wild type, is able to make polyhydroxyalkanoates having chain lengths of the monoalkanoate of from $C_6$ to $C_{16}$. Such cells are, for example, Burkholderia sp., Burkholderia thailandensis, Pseudomonas sp., Pseudomonas putida, Pseudomonas aeruginosa, Pseudomonas oleovorans, Pseudomonas stutzeri, Pseudomonas fluorescens, Pseudomonas citronellolis, Pseudomonas resinovorans, Comamonas testosteroni, Aeromonas hydrophila, Cupriavidus necator, Alcaligenes latus and Ralstonia eutropha. In this context, preferred inventive cells are genetically modified such that they, compared to the wild type thereof, are able to make fewer polyhydroxyalkanoates.

Such cells are, for example, described in Ren et al., Journal Applied Microbiology and Biotechnology 1998 June, 49(6):743-50 as GPp121, GPp122, GPp123 and GPp124, in Huisman et al., J Biol Chem. 1991 Feb. 5; 266(4):2191-8 as GPp104 and in De Eugenio et al., Environ Microbiol. 2010. 12(1):207-21 as KT42C1 and in Ouyang et al. Macromol Biosci. 2007. 7(2):227-33 as KTOY01 and KTOY02.

Such a cell able to make fewer polyhydroxyalkanoates, compared to the wild type thereof, is in particular characterized in that it has, compared to the wild type thereof, a decreased activity of at least one enzyme $E_{11}$, $E_{11}$ being a polyhydroxyalkanoate synthase of EC:2.3.1.-, preferably encoded by a phaC gene, especially a phAc1 or phaC2 gene, or having a polypeptide sequence in which up to 25%, preferably up to 20%, particularly preferably up to 15%, in particular up to 10, 9, 8, 7, 6, 5, 4, 3, 2, 1%, of the amino acid residues of the enzymes encoded by a phaC gene, especially a phAc1 or phaC2 gene, are modified by deletion, insertion, substitution or a combination thereof and which still has at least 10%, preferably 50%, particularly preferably 80%, in particular more than 90%, of the enzymatic activity of the enzyme encoded by a phaC gene, especially a phAc1 or phaC2 gene, enzymatic activity for an enzyme $E_{11}$ being understood to mean the ability to convert 3-hydroxyalkanoyl-coenzyme A to poly-3-hydroxyalkanoic acid, especially 3-hydroxydecanoyl-coenzyme A to poly-3-hydroxydecanoic acid.

Particularly preferred enzymes $E_{11}$ are selected from the enzymes having polypeptide sequence AAM63407.1 or AAM63409.1 or having a polypeptide sequence in which up to 25%, preferably up to 20%, particularly preferably up to 15%, in particular up to 10, 9, 8, 7, 6, 5, 4, 3, 2, 1%, of the amino acid residues are modified with respect to the particular aforementioned accession number by deletion, insertion, substitution or a combination thereof and which still has at least 10%, preferably 50%, particularly preferably 80%, in particular more than 90%, of the enzymatic activity of the enzyme having the particular aforementioned accession number.

The activity of the enzyme $E_{11}$ can be determined spectrophotometrically. After addition of all components, the assay mixture contains 108 mM potassium phosphate buffer (pH 6.0 at 25° C.), 33 mM sodium gluconate, 0.22 mM 2,6-dichlorophenolindophenol (sodium salt), 1.3 mM phenazine methosulphate and 0.005% (w/v) bovine serum albumin. The assay mixture is equilibrated at 25° C. until the absorption at 600 nm stays constant. The reaction is then started by addition of cell-free extracts containing the activity to be measured and the decline in absorption is recorded at 600 nm and 25° C. for about 5 minutes. The concentration of 2,6-dichlorophenolindophenol is determined spectrophotometrically, assuming a molar absorption coefficient of 10 $mM^{-1}$ $cm^{-1}$ at 600 nm. An enzyme activity of 1 unit is defined as the amount of enzyme leading to the reduction of 1.0 μmol of 2,6-dichlorophenolindophenol per minute at 25° C. and pH 6.0.

It is further advantageous and thus preferred when, additionally with respect to $E_1$, the cell according to the invention has been genetically modified such that it, compared to the wild type thereof, has a decreased activity of at least one enzyme $E_{12}$, which is a gluconate 2-dehydrogenase of EC 1.1.1.215.

Preferred enzymes $E_{12}$ are particularly selected from enzymes encoded by a gad gene or having a polypeptide sequence in which up to 25%, preferably up to 20%, particularly preferably up to 15%, in particular up to 10, 9, 8, 7, 6, 5, 4, 3, 2, 1%, of the amino acid residues of the enzymes encoded by a gad gene are modified by deletion, insertion, substitution or a combination thereof and which still has at least 10%, preferably 50%, particularly preferably 80%, in particular more than 90%, of the enzymatic activity of the enzyme encoded by a gad gene, enzymatic activity for an enzyme $E_{12}$ being understood to mean the ability to convert gluconate to 2-dehydrogluconate. The activity of the enzyme $E_{12}$ can be determined by quantification of the coenzyme A (CoA) released in the polymerization of 3-hydroxydecanoyl-coenzyme A. The assay mixture contains 2 mM 3-hydroxydecanoyl-CoA, 40 mM potassium phosphate buffer (pH 7.5), 10 mM 5,5'-dithiobis(2-nitrobenzoic acid) (DTNB) and 1 mg/ml bovine serum albumin. The reaction is started by addition of cell-free extracts containing the activity to be measured and the absorption is recorded at 412 nm and 30° C. The concentration of CoA is determined spectrophotometrically, assuming a molar absorption coefficient of 13 600 $M^{-1}$ $cm^{-1}$ at 412 nm. An enzyme activity of 1 unit is defined as the amount of enzyme leading to the release of 1.0 μmol of CoA per minute at 30° C. and pH 7.5.

It is further advantageous and thus preferred when, additionally with respect to $E_1$, the cell according to the invention has been genetically modified such that it, compared to the wild type thereof, has an increased activity of at least one enzyme $E_{13}$, which catalyses the export of a rhamnolipid of the general formula (I) from the cell into the surrounding medium.

In the case of cells preferred according to the invention, $E_{13}$ is selected from the group consisting of enzymes $E_{13}$ having polypeptide sequence AAG04520.1, AJY02996.1, ZP_05590661.1, YP_439278.1, YP_440069.1, ZP_04969301.1, ZP_04520234.1, YP_335528.1, YP_001075859.1, YP_001061817.1, ZP_02487499.1, YP_337251.1, ZP04897712.1, ZP_04810190.1, YP_990322.1, ZP_02476924.1, ZP_04899735.1, ZP_04893873.1, ZP_02365982.1, YP_001062909.1, YP_105611.1, ZP_03794061.1, ZP_03457011.1, ZP_02385401.1, ZP_02370552.1, YP_105236.1, ZP_04905097.1, YP_776387.1, YP_001811690.1, YP_004348730.1, YP_004348708.1, YP_371320.1, YP_623145.1, YP_001778810.1, YP_002234933.1, CCE52909.1, YP_002908248.1, ZP04954557.1, ZP_04956038.1, ZP_02408950.1, ZP_02375897.1, ZP_02389908.1, YP_439274.1, YP_001074762.1, YP_337247.1, YP_110559.1, ZP_02495927.1, YP_111360.1, YP_105608.1, ZP_02487826.1, ZP_02358947.1, YP_001078605.1, ZP_00438000.1, ZP_00440993.1, ZP_02477260.1, YP_371317.1, YP_001778807.1, ZP_02382843.1, YP_002234936.1, YP_623142.1, ZP_02907618.1, ZP_02891478.1, YP_776390.1, ZP_04943308.1, YP_001811693.1, ZP_02503985.1, YP_004362740.1, YP_002908245.1, YP_004348705.1, ZP_02408798.1, ZP_02417250.1, EGD05166.1, ZP_02458677.1, ZP_02465793.1, YP_001578240.1, ZP_04944344.1, YP_771932.1, ZP_02889166.1, YP_002232614.1, ZP_03574808.1, ZP_02906105.1, YP_001806764.1, YP_619912.1, YP_001117913.1, YP_106647.1, YP_001763368.1, ZP_02479535.1, ZP_02461743.1, YP_560998.1, YP_331651.1, ZP04893070.1, YP_003606714.1, ZP_02503995.1, ZP_06840428.1, YP_104288.1, ZP_02487849.1, ZP_02353848.1, YP_367475.1, ZP_02377399.1, ZP_02372143.1, YP_001897562.1, ZP_02361066.1, YP_440582.1, ZP_03268453.1, AET90544.1, YP_003908738.1, YP_004230049.1, ZP_02885418.1, CDH72316.1, WP_001297013.1, WP_010955775.1, WP_010955671.1, WP_010955672.1, WP_010955673.1, WP_010952401.1, WP_010952402.1, WP_010952403.1, WP_010952855.1, WP_010954573.1, WP_010954631.1, WP_010954632.1, WP_010954404.1, WP_004575310.1 or ZP_02511831.1 or having a polypeptide sequence in which up to 25%, preferably up to 20%, particularly preferably up to 15%, in particular up to 10, 9, 8, 7, 6, 5, 4, 3, 2, 1%, of the amino acid residues are modified with respect to the particular aforementioned accession number by deletion, insertion, substitution or a combination thereof and which still has at least 10%, preferably 50%, particularly preferably 80%, in particular more than 90%, of the enzymatic activity of the enzyme having the particular aforementioned accession number, enzymatic activity for an enzyme $E_{13}$ being understood to mean the ability to export a rhamnolipid of the general formula (I) from the cell into the surrounding medium.

The activity of the enzyme $E_{13}$ can then be determined using the crude cell-free extracts obtained as described above, by determining the amount of the enzyme $E_{13}$ made. This is based on the assumption that more enzyme $E_{13}$ per biomass unit is capable of exporting more rhamnolipid of the general formula (I) from the cell into the surrounding medium. Such a quantification can be carried out by immunological detection by means of antibodies specific for enzyme $E_{13}$ (see Kurien, T. B., Scofield, R. H (Eds.). Protein Blotting and Detection: Methods and Protocols. Methods in Molecular Biology, Vol. 536. 1st Ed., Humana Press. N.Y. USA, 2009) or by mass-spectrometry methods (see Schmidt, A., Kellermann, J. & Lottspeich, F. A novel strategy for quantitative proteornics using isotope-coded protein labels. *Proteomics* 5, 4-15 (2005)).

Alternatively, the activity of the enzyme $E_{13}$ can also be determined by carrying out uptake assays using radioactively labelled rhamnolipids and inside-out vesicles produced from the cells according to the invention. The general procedure is, for example, described in Nies D H. The cobalt, zinc, and cadmium efflux system CzcABC from *Alcaligenes eutrophus* functions as a cation-proton antiporter in *Escherichia coli*. J Bacteriol. 1995. 177(10):2707-12 or Lewinson O, Adler J, Poelarends G J, Mazurkiewicz P, Driessen A J, Bibi E. The *Escherichia coli* multidrug transporter MdfA catalyzes both electrogenic and electroneutral transport reactions. Proc Natl Acad Sci USA. 2003 Feb. 18; 100(4):1667-72.

Particularly preferably, the modified activities of the aforementioned enzymes are in the combinations $E_2E_3E_4E_{13}$, $E_2E_3E_4E_9E_{10}E_{13}$, $E_5E_6E_7E_8E_9E_{10}E_{13}$ and $E_2E_3E_4E_5E_6E_7E_8E_9E_{10}E_{13}$, wherein $E_2E_3E_4E_5E_6E_7E_8E_9E_{10}E_{13}$ is particularly preferred.

Cells according to the invention can be advantageously used for producing rhamnolipids. Therefore, the invention further provides for the use of cells according to the invention for producing compounds of the general formula (I).

The present invention further provides a method for producing rhamnolipids, especially those of the general formula (I),
where
m=2, 1 or 0, in particular 1 or 0,
n=1 or 0, in particular 1,
$R^1$ and $R^2$=mutually independently, identical or different, organic radical having 2 to 24, preferably 5 to 13, carbon atoms, in particular optionally branched, optionally substituted, particularly hydroxy-substituted, optionally unsaturated, in particular optionally mono-, bi- or tri-unsaturated, alkyl radical, preferably those selected from the group consisting of pentenyl, heptenyl, nonenyl, undecenyl and tridecenyl and $(CH_2)_o$—$CH_3$ where o=1 to 23, preferably 4 to 12,
comprising the method steps of
I) contacting the cell according to the invention with a medium containing a carbon source
II) culturing the cell under conditions allowing the cell to make rhamnolipid from the carbon source and
III) optionally isolating the rhamnolipids made.

The genetically modified cells according to the invention can be contacted with the culture medium and thus cultured in a continuous or discontinuous manner in a batch process or in a fed-batch process or repeated fed-batch process for the purposes of producing the aforementioned products. Also conceivable is a semi-continuous process, as described in GB-A-1009370. An overview of known cultivation methods is available in the textbook by Chmiel ("Bioprozesstechnik 1. Einführung in die Bioverfahrenstechnik" [Bioprocess technology 1. Introduction to Bioprocess Technology] (Gustav Fischer Verlag, Stuttgart, 1991)) or in the textbook by Storhas ("Bioreaktoren und periphere Einrichtungen" [Bioreactors and Peripheral Devices] (Vieweg Verlag, Braunschweig/Wiesbaden, 1994)).

The culture medium to be used has to satisfy the demands of the particular strains in a suitable manner. Descriptions of culture media of various yeast strains are, for example, included in "Nonconventional yeast in biotechnology" (Ed. Klaus Wolf, Springer-Verlag Berlin, 1996). The carbon source used can be carbohydrates such as, for example, glucose, sucrose, arabinose, xylose, lactose, fructose, maltose, molasses, starch, cellulose and hemicellulose, vegetable and animal oils and fats such as, for example, soya oil, safflower oil, arachis oil, hemp oil, jatropha oil, coconut fat, pumpkin seed oil, linseed oil, corn oil, poppy seed oil, evening primrose oil, olive oil, palm kernel oil, palm oil, rapeseed oil, sesame oil, sunflower oil, grape seed oil, walnut oil, wheatgerm oil and coconut fat, fatty acids, such as, for example, caprylic acid, capric acid, lauric acid, myristic acid, palmitic acid, palmitoleic acid, stearic acid, arachidonic acid, behenic acid, oleic acid, linoleic acid, linolenic acid, gamma-linolenic acid and the methyl or ethyl ester thereof and also fatty acid mixtures, mono-, di- and triglycerides containing the fatty acids just mentioned, alcohols such as, for example, glycerol, ethanol and methanol, hydrocarbons such as methane, carbonaceous gases and gas mixtures, such as CO, $CO_2$, synthesis or flue gas, amino acids such as L-glutamate or L-valine or organic acids such as, for example, acetic acid. These substances may be used individually or as a mixture. Particular preference is given to the use of carbohydrates, especially of monosaccharides, oligosaccharides or polysaccharides, as the carbon source, as described in U.S. Pat. Nos. 6,01,494 and 6,136,576, and of hydrocarbons, especially of alkanes, alkenes and alkynes and also the monocarboxylic acids derived therefrom and the mono-, di- and triglycerides derived from said monocarboxylic acids, and of glycerol and acetate. Very particular preference is given to mono-, di- and triglycerides containing the esterification products of glycerol with caprylic acid, capric acid, lauric acid, myristic acid, palmitic acid, palmitoleic acid, stearic acid, arachidonic acid, behenic acid, oleic acid, linoleic acid, linolenic acid and/or gamma-linolenic acid.

A major advantage of the present invention is that the cells according to the invention are able to make rhamnolipids from the simplest carbon sources such as, for example, glucose, sucrose or glycerol, meaning that it is not necessary to provide longer-chain carbon sources in the medium during the method according to the invention. Thus, in the event of insufficient availability, it is advantageous that the medium in step I) of the method according to the invention contains no amounts or no detectable amounts of carboxylic acids having a chain length of greater than six carbon atoms or esters or glycerides derivable therefrom.

The nitrogen source used may be organic nitrogen-containing compounds such as peptones, yeast extract, meat extract, malt extract, corn steep liquor, soya bean meal and urea or inorganic compounds such as ammonium sulphate, ammonium chloride, ammonium phosphate, ammonium carbonate and ammonium nitrate, ammonia, ammonium hydroxide or aqueous ammonia. The nitrogen sources may be used individually or as a mixture.

The phosphorus source used may be phosphoric acid, potassium dihydrogen phosphate or dipotassium hydrogen phosphate or the corresponding sodium-containing salts. Furthermore, the culture medium must contain salts of metals such as, for example, magnesium sulphate or iron sulphate that are necessary for growth. Finally, essential growth substances such as amino acids and vitamins may be used in addition to the substances mentioned above. Moreover, suitable precursors may be added to the culture medium. The aforementioned starting materials may be added to the culture in the form of a single batch or be appropriately fed in during cultivation.

To control the pH of the culture, appropriate use is made of basic compounds such as sodium hydroxide, potassium hydroxide, ammonia or aqueous ammonia or acidic compounds such as phosphoric acid or sulphuric acid. To control the evolution of foam, it is possible to use antifoams such as, for example, fatty acid polyglycol esters. To maintain the stability of plasmids, it is possible to add to the medium suitable selective substances such as, for example, antibiotics. In order to maintain aerobic conditions, oxygen or oxygenous gas mixtures, for example air, are introduced into the culture.

The temperature of the culture is normally more than 20° C., preferably more than 25° C., and it can also be more than 40° C., a cultivation temperature of 95° C., particularly preferably 90° C. and most preferably 80° C. advantageously not being exceeded.

In step III) of the method according to the invention, the rhamnolipids made by the cells can optionally be isolated from the cells and/or the culture medium, it being possible to use for the purposes of isolation all methods known to a person skilled in the art for isolating low-molecular-weight substances from complex compositions such as, for example, filtration, extraction, adsorption (chromatography) or crystallization.

Furthermore, the product phase contains remnants of biomass and various impurities, such as oils, fatty acids and other culture-medium constituents. The impurities are preferably removed in a solvent-free process. For example, the product phase can be diluted with water in order to facilitate pH adjustment. Product phase and aqueous phase can then be homogenized by transferring the rhamnolipids into a water-soluble form by lowering or raising the pH by means of acids or alkalis. Potentially, the solubilization of the rhamnolipids in the aqueous phase can be supported by incubation at relatively high temperatures, for example at from 60 to 90° C., and constant mixing. As a result of subsequent raising or lowering of the pH by means of alkalis or acids, the rhamnolipids can then be transferred into a water-insoluble form again, and so they can be easily separated from the aqueous phase. The product phase can then be additionally washed with water one or more times in order to remove water-soluble impurities.

Oil residues can, for example, be removed by extraction by means of suitable solvents, advantageously by means of organic solvents. An alkane such as, for example, n-hexane is preferred as solvent.

As an alternative to the above-described solvent-free process, the product can be removed from the aqueous phase using a suitable solvent, for example an ester such as, for example, ethyl acetate or butyl acetate. The stated extraction steps can be carried out in any desired order. Here, solvents are preferably used, in particular organic solvents. The preferred solvent is n-pentanol. The solvent is removed by, for example, distillation. Thereafter, the lyophilized product can be further purified, for example by means of chromatographic methods. Examples which can be mentioned at this point include precipitation using suitable solvents, extraction using suitable solvents, complexing, for example by means of cyclodextrins or cyclodextrin derivatives, crystallization, purification or isolation by means of chromatographic methods or transfer of the rhamnolipids into easily removable derivatives.

A particularly suitable rhamnolipid isolation procedure in method step III) comprises the method sub steps of
A) transferring the rhamnolipids to an aqueous medium having a pH of less than 6,
B) contacting the medium with at least one organic solvent to obtain a multi-phase system and removing the aqueous phase,
C) increasing the pH to a pH of 6 or greater to obtain a multi-phase organic system,
D) removing an organic phase enriched with rhamnolipid and
E) optionally further purifying the rhamnolipid.

A detailed description of how to carry out this preferred embodiment of method step III) is given in US20140148588.

The present invention likewise provides the rhamnolipids obtainable using the method according to the invention, especially also the above-described rhamnolipid mixtures obtainable using the method according to the invention.

Advantageously, the rhamnolipids and mixtures obtainable using the method according to the invention can be used in cleaning agents, in cosmetic or pharmaceutical formulations and in crop-protection formulations.

Thus, the present invention further provides for the use of the rhamnolipids obtained using the method according to the invention for producing cosmetic, dermatological or pharmaceutical formulations, crop-protection formulations and also care products and cleaning agents and surfactant concentrates.

The examples adduced hereinafter describe the present invention by way of example, without any intention that the invention, the scope of application of which is apparent from the entirety of the description and the claims, be restricted to the embodiments specified in the examples.

The following figures are a component of the examples:

FIG. 1: Total yields of the strains PP-155 and PP-099 [Δgcd] in parallel experiments (runs #1-3) and comparison of the mean values

EXAMPLES

Example 1 (not Inventive): Use was Made of Strain BS-PP-155 (*P. putida* KT2440 Δupp+pACYCATh5-{PrhaSR}[rhaSR_Ec]{PrhaBAD}[rhlABC_Pa]{Talk}[araC_Ec]{ParaBAD}[rmlBDAC_Pa]{Talk}; clone 1)

Construction of the Strain BS-PP-155

For the heterologous expression of the genes rhlA, rhlB and rhlC and of the genes rmlB, rmlD, rmlA and rmlC, both from *P. aeruginosa*, the plasmid pACYCATh5-{PrhaSR}[rhaSR_Ec]{PrhaBAD}[rhlABC_Pa]{Talk}[araC_Ec]{ParaBAD}[rmlBDAC_Pa]{Talk} was constructed. The plasmid contains, firstly, a synthetic operon consisting of the genes rhlA and rhlB (encoding a rhamnosyltransferase 1) and rhlC (encoding a rhamnosyltransferase 2) from *P. aeruginosa* DSM1128 (SEQ ID No 1) and, secondly, an operon consisting of the genes rmlB (encoding a dTDP-D-glucose 4,6-dehydratase), rmlD (encoding a dTDP-4-dehydrorhamnose reductase), rmlA (encoding a glucose-1-phosphate thymidylyltransferase) and rmlC (encoding a dTDP-4-dehydrorhamnose 3,5-epimerase) from *P. aeruginosa* DSM 19880 (SEQ ID No 2). The genes rhlABC are under the control of the rhamnose-inducible $P_{Rha}$ promoter; the rmlBDAC genes are under the control of the arabinose-inducible $P_{BAD}$ promoter. Situated downstream of the two operon structures is a terminator sequence (rrnB T1T2). The rmlBDAC genes were amplified from genomic DNA from *P. aeruginosa* DSM19880 and the synthetic rhlABC operon was obtained by gene synthesis. The $P_{Rha}$ promoter cassette (SEQ ID No 3) and $P_{BAD}$ promoter cassette (SEQ ID No 4) and also the terminator sequence (SEQ ID No 5) were amplified from genomic *E. coli* DNA. Whereas the rhlABC genes are required for the synthesis of di-rhamnolipids, the rmlBDAC genes are needed for the provision of activated dTDP-L-rhamnose.

The vector is based on the plasmid pACYC184 (New England Biolabs, Frankfurt am Main, Germany) and bears a p15A origin of replication for replication in *E. coli* and a pVS1 origin of replication for replication in *P. putida*. The pVS1 origin of replication was amplified from the *Pseudomonas* plasmid pVS1 (Itoh Y, Watson J M, Haas D, Leisinger T, Plasmid 1984, 11(3), 206-20). The vector part and the DNA fragments were cloned using a commercially available in vitro DNA assembly kit (e.g. NEBuilder HiFi DNA Assembly Cloning Kit in accordance with the manufacturer's instructions (NEB; Frankfurt am Main, Germany)). Chemically competent *E. coli* 10 beta cells (NEB, Frankfurt am Main, Germany) were transformed in a manner known to a person skilled in the art. The correct insertion of the target genes was checked by restriction analysis and the authenticity of the introduced homologous regions confirmed by DNA sequencing. The size of the resulting plasmid pACYCATh5-{PrhaSR}[rhaSR_Ec]{PrhaBAD}[rhlABC_Pa]{Talk}[araC_Ec]{ParaBAD}[rmlBDAC_Pa]{Talk} (SEQ ID No 6) is 17 337 bp. Thereafter, the plasmid was introduced into *P. putida* KT2440 Δupp. This strain is used as the starting strain for the construction of markerless gene deletions in *P. putida* (Graf & Altenbuchner, 2011, Applied and Environmental Microbiology, Vol 77, No. 15, 5549-5552, DOI: 10.1128/AEM.05055-11). The method is based on a negative counter-selection system for *P. putida*, which utilizes the activity of uracil phosphoribosyltransferase and the sensitivity of *P. putida* towards the antimetabolite 5-fluorouracil. The deletion of the upp gene has no effect on rhamnolipid biosynthesis.

The transformation of *P. putida* KT2440 Δupp with the vector pACYCATh5-{PrhaSR}[rhaSR_Ec]{PrhaBAD}[rhlABC_Pa]{Talk}[araC_Ec]{ParaBAD}[rmlBDAC_Pa]{Talk} was carried out as described in Iwasaki et al. (Iwasaki K, Uchiyama H, Yagi O, Kurabayashi, T, Ishizuka K, Takamura Y, Biosci. Biotech. Biochem. 1994. 58(5):851-854). The plasmid DNA from each of 10 clones was isolated and analysed. A strain bearing the plasmid was called *P. putida* KT2440 Δupp pACYCATh5-{PrhaSR}[rhaSR_Ec]{PrhaBAD}[rhlABC_Pa]{Talk}[araC_Ec]{ParaBAD}[rmlBDAC_Pa]{Talk}.

The biotechnological production of surfactant was carried out in the 8-fold parallel fermentation system "DASGIP" from Eppendorf.

For the fermentation, 1 L reactors were used. The pH probes were calibrated by means of a two-point calibration with measurement solutions of pH 4.0 and pH 7.0. The reactors were filled with 300 mL of water and autoclaved for 20 min at 121° C. in order to ensure sterility. The water was removed the next morning in a clean bench and replaced with sterile fermentation medium (autoclaved: 2.2 g/L $(NH_4)_2SO_4$, 0.02 g/L NaCl, 0.4 g/L $MgSO_4 \times 7H_2O$, 0.04 g/L $CaCl_2 \times 2H_2O$, sterilized separately: 2 g/L $KH_2PO_4$, 15 g/L glucose, 10 mL/L trace element solution M12 [sterile-filtered: 0.2 g/L $ZnSO_4 \times 7H_2O$, 0.1 g/L $MnCl_1 \times 4H_2O$, 1.5 g/L $Na_3$ citrate$\times 2H_2O$, 0.1 g/L $CuSO_4 \times 5H_2O$, 0.002 g/L $NiCl_2 \times 6H_2O$, 0.003 g/L $Na_2MoO_4 \times 2H_2O$, 0.03 g/L $H_3BO_3$, 1 g/L $FeSO_4 \times 7H_2O$]). Subsequently, the $pO_2$ probes were calibrated by means of a one-point calibration (stirrer: 600 rpm/aeration: 10 sL/h air), and the feed, correcting agent and induction agent lines cleaned by means of cleaning-in-place. To this end, the hoses were flushed with 70% ethanol, then with 1 M NaOH, then with sterile demineralized water and finally filled with the particular media. Using 100 μL from a cryoculture, the strain (*P. putida* KT2440 Δupp+pACYCATh5-{PrhaSR}[rhaSR_Ec]{PrhaBAD}[rhlABC_Pa]{Talk}[araC_Ec]{ParaBAD}[rmlBDAC_Pa]{Talk} was first grown overnight at 30° C. and 200 rpm for approximately 18 h in 25 mL of LB 1 medium (10 g/L casein hydrolysate, 5 g/L yeast extract, 1 g/L NaCl) in a 250 mL baffled flask containing 50 mg/L kanamycin. After measurement of the optical density of the culture, 50 mL of sterile seed medium (autoclaved: 4.4 g/L $Na_2HPO_4 * 2H_2O$, 1.5 g/L $KH_2PO_4$, 1 g/L $NH_4C_1$, 10 g/L yeast extract, sterilized separately: 20 g/L glucose, 0.2 g/L $MgSO_4 * 7H_2O$, 0.006 g/L $FeCl_3$, 0.015 g/L $CaCl_2$, 1 mL/L trace element solution SL6 [sterile-filtered: 0.3 g/L $H_3BO_3$, 0.2 g/L $CoCl_2 \times 6H_2O$, 0.1 g/L $ZnSO_4 \times 7H_2O$, 0.03 g/L $MnCl_2 \times 4H_2O$, 0.01 g/L $CuCl_2 \times 2H_2O$, 0.03 g/L $Na_2MoO_4 \times 2H_2O$, 0.02 g/L $NiCl_2 \times 6H_2O$]) in a 500 mL baffled flask were inoculated from the LB preculture using a start $OD_{600}$ of 0.2 and incubated for approximately 7 h at 30° C. and 200 rpm. At an optical density of approximately $OD_{600}$ 8, the main culture was inoculated using a start $OD_{600}$ of 0.7.

In order to inoculate the reactors using an optical density of 0.7, approximately 26 mL were filled in a 30 mL syringe and the reactors were inoculated by means of a needle across a septum.

The following standard program was used:

| DO regulator | | | pH regulator | | |
|---|---|---|---|---|---|
| Preset | 0% | | Preset | | 0 ml/h |
| P | 0.1 | | P | | 5 |
| Ti | 300 s | | Ti | | 200 s |
| Min | 0% | | Min | | 0 mlL/h |
| Max | 100% | | Max | | 40 mL/h |
| N (Rotation) | from | to | XO2 (gas mixture) | from | to |
| Growth and biotransformation | 0% 500 rpm | 40% 1500 rpm | Growth and biotransformation | 0% 21% | 100% 21% |
| F (gas flow rate) | | | from | | to |
| Growth and biotransformation | | | 35% 9 sL/h | | 100% 72 sL/h |
| Script | | | | | |
| Trigger activated | | | 31% DO (1/60 h) | | |
| Induction, rhamnose, arabinose | | | 3 h after feed start | | |
| Feed trigger | | | 50% DO | | |
| Feed rate | | | 1.5 [mL/h] | | | pH was one-sidedly adjusted to pH 7.0 using ammonia (12.5%). During cultivation and biotransformation, the dissolved oxygen in the culture was kept constant at 30% via stirrer speed and aeration rate. The fermentation was carried out as a fed batch, where, from the feed start, the feeding with 2.5 g/Lh glucose by means of a 500 g/L glucose feed was triggered via a DO peak. The expression of the recombinantly introduced genes was induced 3 h after the feed start by the automatic addition of 0.2% (w/v) rhamnose and 0.2% (w/v) arabinose. The required amounts of induction sugar are based on the fermentation starting volume. For both sugars, 220 g/L stock solutions were used. The production of surfactant started from the time of induction. All online measurement data such as pH, DO, CTR, OTR, but also the flow rates and amount of the substrates such as ammonia solution for pH adjustment, the glucose feed or the inducer flow rates, were logged by the DASGIP fermentation system.

For fermentation analysis, a 10 mL syringe was used to draw and discard 2 mL as forerun from each vessel. This was followed once more by 6 mL for the actual analysis. Rhamnolipid content, glucose concentration and dry biomass were determined. The fermentation was ended after 65 h.

Rhamnolipid concentration was determined by means of HPLC. 100 μL of the fermentation sample were admixed with 900 μL of 70% (v/v) n-propanol in an Eppendorf tube and shaken at 30 Hz for 1 min in a Retsch mill. Thereafter, the sample was centrifuged at 13 000 rpm for 5 min and the supernatant transferred to a fresh Eppendorf tube. In the event of a further dilution being necessary, this was done using 55% n-propanol. All tubes were closed quickly in order to avoid evaporation. The samples were then transferred to HPLC vials and stored at −20° C. until measurement.

1 ml of acetone was charged in a 2 ml reaction tube using a positive displacement pipette (Combitip) and the reaction tube immediately closed to minimize evaporation. This was followed by the addition of 1 ml of culture broth. After vortexing of the culture broth/acetone mixture, said mixture was centrifuged for 3 min at 13 000 rpm, and 800 μl of the supernatant transferred to an HPLC vial.

An evaporative light scattering detector (Sedex LT-ELSD Model 85LT) was used for detection and quantification of rhamnolipids. The actual measurement was carried out using an Agilent Technologies 1200 Series (Santa Clara, Calif.) and a Zorbax SB-C8 Rapid Resolution column (4.6×150 mm, 3.5 μm, Agilent). The injection volume was 5 μl and the method run time was 20 min. Aqueous 0.1% TFA (trifluoroacetic acid, solution A) and methanol (solution B) was used as mobile phase. The column temperature was 40° C. The ELSD (detector temperature 60° C.) and the DAD (diode array, 210 nm) served as detectors. The gradient used in the method was:

| t [min] | Solution B % by volume | Flow rate [ml/min] |
|---|---|---|
| 0.00 | 70% | 1.00 |
| 15.00 | 100% | 1.00 |
| 15.01 | 70% | 1.00 |
| 20.00 | 70% | 1.00 |

Dry biomass was determined by pipetting approximately 1 ml of the sample into a pre-weighed Eppendorf tube and determining the initial weight. Thereafter, the sample was admixed with approximately 1 mL of mains water, mixed, and centrifuged at 13 000 rpm for 5 min. The supernatant was discarded and the Eppendorf tube was coarsely wiped. 1 mL of mains water was added once more and resuspension was carried out at 30 Hz for 1 min in a Retsch mill. Thereafter, centrifugation was carried out at 13 000 rpm for 10 min, the supernatant was discarded, and the Eppendorf tube was then wiped dry, for example with cotton swabs, without biomass being taken from the Eppendorf tube at the same time. The samples were dried at 105° C. for 48 h and reweighed after cooling. A duplicate determination was carried out in each case.

Dry biomass calculation was then carried out in Excel:

$$DBM = \frac{\text{Back weight} - \text{Tare weight}}{\text{Initial weight} - \text{Tare weight}} \cdot 1000 \left[\frac{g}{L}\right]$$

Glucose concentration was measured with the aid of a Roche Cedex Bio HT as specified by the manufacturer after centrifugation and sterile-filtration of a fermentation sample. 3 experiments are carried out, each in parallel to Example 2.

Example 2: Use was Made of the Strain BS-PP-099 (*P. putida* KT2440 Δupp Δgcd+pACYCATh5-{PrhaSR}[rhaSR_Ec]{PrhaBAD}[rhlABC_Pa]{Talk}[araC_Ec]{ParaBAD}[rmlBDAC_Pa]{Talk})

Construction of a Vector for the Deletion of the Gcd Gene in *Pseudomonas putida* KT2440 Δupp A vector for the deletion of the gcd gene from *P. putida* KT2440 Δupp, encoding a glucose dehydrogenase, was prepared by PCR amplification of approximately 680 bp upstream and downstream of the gcd gene.

The following primers were used for the amplification of the homologous regions upstream and downstream of the gcd gene:

```
PCR 1: Region upstream of gcd
4*54
                                    (SEQ ID No 7)
5'-GCCGCTTTGGTCCCGGGTTTCAAGCTCAGCGG-3'

4*57
                                    (SEQ ID No 8)
5'-AAGGCGCGATCGCGGGTTAGAAACTGCTCTGG-3'

PCR 2: Region downstream of gcd
4*56
                                    (SEQ ID No 9)
5'-CCGCGATCGCGCCTTGTGTCGCGTTTC-3'

4*55
                                   (SEQ ID No 10)
5'-GCTTGCATGCCTGCAATGCCGTAGGCTTTGACC-3'
```

The following parameters were used for the PCR:

| Denaturation: | 98° C. | 30 s | |
| Denaturation: | 98° C. | 10 s | 30x |
| Annealing: | 62° C. | 12 s | 30x |
| Elongation: | 72° C. | 22 s | 30x |
| Final elongation: | 72° C. | 5 min | |

For the amplification, the Phusion™ High-Fidelity Master Mix from NEB (Frankfurt am Main, Germany) was used according to the manufacturer's recommendations. 50 μl of each of the PCR reactions were then resolved on a 1% TAE agarose gel. The PCR, the agarose gel electrophoresis, ethidium bromide staining of the DNA and determination of the PCR fragment sizes were performed in a manner known to a person skilled in the art. PCR fragments of the expected size (PCR 1, 679 bp (SEQ ID No 11); PCR 2, 682 bp, (SEQ ID No 12)) were amplified. The PCR products were purified using the "QIAquick PCR Purification Kit" from Qiagen as specified by the manufacturer. Using the NEBuilder HiFi DNA Assembly Cloning Kit in accordance with the manufacturer's instructions (NEB; Frankfurt am Main, Germany), the purified PCR products were cloned into a BamHI- and SbfI-cut pKOPp vector (SEQ ID No. 13). Chemically competent E. coli 10 beta cells (NEB, Frankfurt am Main, Germany) were transformed in a manner known to a person skilled in the art. The correct insertion of the target genes was checked by restriction analysis and the authenticity of the introduced homologous regions confirmed by DNA sequencing. The resultant knock-out vector was referred to as pKOPp_gcd (SEQ ID No. 14).

Construction of the strain BS-PP-099

The construction of the strain P. putida KT2440 Δupp Δgcd was carried out with the aid of the plasmid pKOPp_gcd and a method described in Graf et al., 2011 (Graf N, Altenbuchner J, Appl. Environ. Micorbiol., 2011, 77(15): 5549; DOI: 10.1128/AEM.05055-11). The DNA sequence after the deletion of gcd is described in SEQ ID No. 15. The transformation of P. putida KT2440 Δupp Δgcd with the vector pACYCATh5-{PrhaSR}[rhaSR_Ec]{PrhaBAD} [rhlABC_Pa]{Talk}[araC_Ec]{ParaBAD}[rmlBDAC_Pa] {Talk} was carried out as described in Iwasaki et al. (Iwasaki K, Uchiyama H, Yagi O, Kurabayashi, T, Ishizuka K, Takamura Y, Biosci. Biotech. Biochem. 1994. 58(5):851-854). Thereafter, the cells were plated out on LB agar plates supplemented with kanamycin (50 μg/ml). The plasmid pACYCATh5-{PrhaSR}[rhaSR_Ec]{PrhaBAD} [rhlABC_Pa]{Talk}[araC_Ec]{ParaBAD}[rmlBDAC_Pa] {Talk}(SEQ ID No. 6) has already been described in Example 1. The plasmid DNA from each of 10 clones was isolated and analysed by means of restriction analysis. A strain bearing the plasmid was called P. putida KT2440 Δupp Δgcd pACYCATh5-{PrhaSR}[rhaSR_Ec]{PrhaBAD}[rhlABC_Pa]{Talk}[araC_Ec]{ParaBAD}[rmlBDAC_Pa]{Talk}.

Technical realization was carried out as described in Example 1.

3 experiments were carried out, each in parallel to Example 1.

What was evaluated was the total yield, determined as the sum of biomass plus rhamnolipid made divided by glucose used and consumed.

As can be seen in FIG. 1, a P. putida strain containing not only rhlA, rhlB and rhlC but also the native gene for glucose dehydrogenase achieves a total yield of 0.258 [(g biomass+g RL)/g glucose] on average. By comparison, the strain with deletion of the gcd gene achieves a total yield of 0.283 [(g biomass+g RL)/g glucose] on average.

Example 3: Construction of the Strain Pseudomonas aeruginosa PAO1 Δgcd

The construction of the strain P. aeruginosa PAO1 Δgcd is carried out with the aid of a method described in Choi & Schweizer (Choi & Schweizer, MBC Microbiology, 2005 5:30, DOI: 10.1186/1471-2180-5-30). The method allows the production of markerless gene deletions in P. aeruginosa and is based on a negative counter-selection system (sacB) using homologous recombination and an Flp-FRT recombination system for the removal of the selection marker. The DNA sequence after the deletion of gcd is described in SEQ ID No. 16. Technical realization is carried out as described in Example 1 with the exception that all cultivation steps are carried out at 37° C.

3 experiments are carried out, each in parallel to the strain P. aeruginosa PAO1.

What is evaluated is the total yield, determined as the sum of biomass plus rhamnolipid made divided by glucose used and consumed. The P. aeruginosa strain still containing the native gene for glucose dehydrogenase achieves on average a lower total yield [(g biomass+g RL)/g glucose] compared to the strain having the deletion of the gcd gene.

Example 4 (not Inventive): Use is Made of the Strain P. putida KT2440 Δupp+pACYCATh5-{PrhaSR}[rhaSR_Ec]{PrhaBAD}[rhlAB_Pa]{Talk} [araC_Ec]{ParaBAD}[rmlBDAC_Pa]{Talk}; clone 1)

Construction of the Strain.

For the heterologous expression of the genes rhlA and rhlB and of the genes rmlB, rmlD, rmlA and rmlC, both from P. aeruginosa, the plasmid pACYCATh5-{PrhaSR}[rhaSR_Ec]{PrhaBAD}[rhlAB_Pa]{Talk}[araC_Ec]{ParaBAD} [rmlBDAC_Pa]{Talk} is constructed. The plasmid contains, firstly, an operon consisting of the genes rhlA and rhlB (encoding a rhamnosyltransferase 1) from P. aeruginosa DSM1128 (SEQ ID No 17) and, secondly an operon consisting of the genes rmlB (encoding a dTDP-D-glucose 4,6-dehydratase), rmlD (encoding a dTDP-4-dehydrorhamnose reductase), rmlA (encoding a glucose-1-phosphate thymidylyltransferase) and rmlC (encoding a dTDP-4-dehydrorhamnose 3,5-epimerase) from P. aeruginosa DSM 19880 (SEQ ID No 2). The rhlAB genes are under control of the rhamnose-inducible $P_{Rha}$ promotor; the rmlBDAC genes are under the control of the arabinose-inducible $P_{BAD}$ promotor. Situated downstream of the two operon structures is a terminator sequence (rrnB T1T2). Whereas the rhlAB genes are required for the synthesis of monorhamnolipids, the rmlBDAC genes are needed for the provision of activated dTDP-L-rhamnose.

The vector is based on the plasmid pACYCATh5-{PrhaSR}[rhaSR_Ec]{PrhaBAD}[rhlABC_Pa]{Talk}[araC_Ec]{ParaBAD}[rmlBDAC_Pa]{Talk} (SEQ ID No 6) (see Example 1). To remove the rhlC gene, the vector was cut with PacI and NsiI. In addition to rhlC, a section upstream and downstream of rhlC is also eliminated by the restriction. These missing regions are amplified by PCR. The template used is the plasmid pACYCATh5-{PrhaSR}[rhaSR_Ec]{PrhaBAD}[rhlABC_Pa]{Talk}[araC_Ec]{ParaBAD}[rmlBDAC_Pa]{Talk} (SEQ ID No 6) (see Example 1). The vector part and both PCR fragments are then cloned using a commercially available in vitro DNA assembly kit (e.g. NEBuilder HiFi DNA Assembly Cloning Kit in accordance with the manufacturer's instructions (NEB; Frankfurt/Main, Germany). Chemically competent E. coli 10 beta cells (NEB, Frankfurt/Main, Germany) are transformed in a manner known to a person skilled in the art. The correct insertion of the target genes is checked by restriction analysis and the authenticity of the introduced homologous regions confirmed by DNA sequencing. The size of the resulting plasmid pACYCATh5-{PrhaSR}[rhaSR_Ec]{PrhaBAD}[rhlAB_Pa]{Talk}[araC_Ec]{ParaBAD}[rmlBDAC_Pa]{Talk} (SEQ ID No 18) is 16 359 bp.

Thereafter, the plasmid is introduced into P. putida KT2440 Δupp. This strain is used as the starting strain for the construction of markerless gene deletions in P. putida (Graf & Altenbuchner, 2011, Applied and Environmental Microbiology, Vol 77, No. 15, 5549-5552, DOI:10.1128/AEM.05055-11). The method is based on a negative counter-selection system for P. putida, which utilizes the activity of uracil phosphoribosyltransferase and the sensitivity of P. putida towards the antimetabolite 5-fluorouracil. The deletion of the upp gene has no effect on rhamnolipid biosynthesis.

The transformation of P. putida KT2440 Δupp with the vector pACYCATh5-{PrhaSR}[rhaSR_Ec]{PrhaBAD}[rhlAB_Pa]{Talk}[araC_Ec]{ParaBAD}[rmlBDAC_Pa]{Talk} is carried out as described in Iwasaki et al. (Iwasaki K, Uchiyama H, Yagi O, Kurabayashi, T, Ishizuka K, Takamura Y, Biosci. Biotech. Biochem. 1994. 58(5):851-854). The plasmid DNA from each of 10 clones is isolated and analysed. A strain bearing the plasmid is called P. putida KT2440 Δupp pACYCATh5-{PrhaSR}[rhaSR_Ec]{PrhaBAD}[rhlAB_Pa]{Talk}[araC_Ec]{ParaBAD}[rmlBDAC_Pa]{Talk}.

Example 5 (Inventive): Use is Made of the Strain P. putida KT2440 Δupp Δgcd+pACYCATh5-{PrhaSR}[rhaSR_Ec]{rhaBAD}[rhlAB_Pa]{Talk} [araC_Ec]{ParaBAD}[rmlBDAC_Pa]{Talk})

Construction of the Strain P. putida KT2440 Δupp Δgcd+ pACYCATh5-{PrhaSR}[rhaSR_Ec]{rhaBAD} rhlAB_Pa {Talk}[araC_Ec]{ParaBAD}[rmlBDAC_Pa]{Talk})

To construct the strain P. putida KT2440 Δupp Δgcd+ pACYCATh5-{PrhaSR}[rhaSR_Ec]{PrhaBAD} [rhlAB_Pa]{Talk}[araC_Ec]{ParaBAD}[rmlBDAC_Pa] {Talk}), the plasmid pACYCATh5-{PrhaSR}[rhaSR_Ec] {PrhaBAD}[rhlAB_Pa]{Talk}[araC_Ec]{ParaBAD} [rmlBDAC_Pa]{Talk} is introduced into the strain P. putida KT2440 Δupp Δgcd. The construction of the strain has already been described in Example 2 and the plasmid construction in Example 4.

The transformation is carried out as described in Iwasaki et al. (Iwasaki K, Uchiyama H, Yagi O, Kurabayashi, T, Ishizuka K, Takamura Y, Biosci. Biotech. Biochem. 1994. 58(5):851-854). Thereafter, the cells are plated out on LB-agar plates supplemented with kanamycin (50 µg/ml). The plasmid DNA from each of 10 clones is isolated and analysed by means of restriction analysis. A strain bearing the plasmid is called P. putida KT2440 ☐upp ☐gcd pACYCATh5-{PrhaSR}[rhaSR_Ec]{PrhaBAD}[rhlABC_Pa] {Talk}[araC_Ec]{ParaBAD}[rmlBDAC_Pa]{Talk}. Technical realization is carried out as described in Example 1. 3 experiments are carried out, each in parallel to Example 4.

What is evaluated is the total yield, determined as the sum of biomass plus rhamnolipid made divided by glucose used and consumed.

The P. putida strain, which besides rhlA and rhlB contains the native gene for glucose dehydrogenase, achieves on average a lower total yield [(g biomass+g RL)/g glucose] compared to the strain with the deletion of the gcd gene.

The invention claimed is:

1. A cell able to make at least one rhamnolipid a compound comprising general formula 1, wherein the cell is *P. putida* KT2440 Aupp Agcd+pACYCATh5-{PrhaSR} [rhaS-R_Ec] {rhaBAD} [rhlAB_Pa] {Talk} [araC_Ec] {ParaBAD} [rmlBDAC_Pa] {Talk}[D]], and wherein general formula (I) is

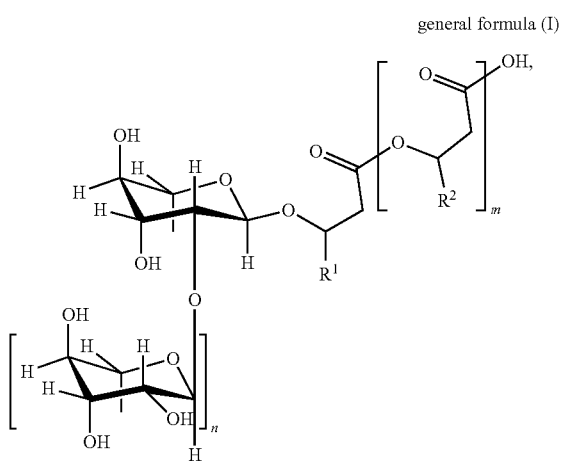

general formula (I)

where
m=2, 1, or 0
n=1 or 0,
and $R^1$ is an organic radical having from 2 to 24 carbon atoms, and $R^2$ is is an organic radical having from 2 to 24 carbon atoms.

2. The cell according to claim 1, wherein the rhamnolipid comprises a mixture of rhamnolipids comprising when n=1 in general formula (I) is more than 80% by weight of the rhamnolipids.

3. The cell according to claim 1, wherein $R^1$ is an organic radical having from 5 to 13 carbon atoms, and $R^2$ is an organic radical having from 5 to 13 carbon atoms.

4. The cell according to claim 1, wherein $R^1$ is selected from the group consisting of pentenyl, heptenyl, nonenyl, undecenyl and tridecenyl and $(CH_2)_o$—$CH_3$ where o=1 to 23.

5. The cell according to claim 1, wherein $R^2$ is selected from the group consisting of pentenyl, heptenyl, nonenyl, undecenyl and tridecenyl and $(CH_2)_o$—$CH_3$ where o=1 to 23.

6. The cell according to claim 1, wherein $R^2$ is selected from the group consisting of pentenyl, heptenyl, nonenyl, undecenyl and tridecenyl and $(CH_2)_o$—$CH_3$ where o=4 to 12.

7. The cell according to claim 1, wherein $R^1$ and $R^2$ is

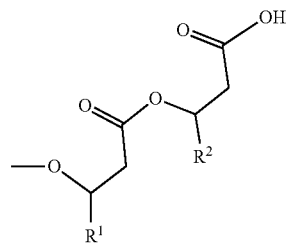

derived from 3-hydroxyoctanoyl-3-hydroxyoctanoic acid, 3-hydroxyoctanoyl-3-hydroxydecanoic acid, 3-hydroxydecanoyl-3-hydroxyoctanoic acid, 3-hydroxyoctanoyl-3-hydroxydecenoic acid, 3-hydroxydecenoyl-3-hydroxyoctanoic acid, 3-hydroxyoctanoyl-3-hydroxydodecanoic acid, 3-hydroxydodecanoyl-3-hydroxyoctanoic acid, 3-hydroxyoctanoyl-3-hydroxydodecenoic acid, 3-hydroxydodecenoyl-3-hydroxyoctanoic acid, 3-hydroxydecanoyl-3-hydroxydecanoic acid, 3-hydroxydecenoic acid, 3-hydroxydecanoyl-3-hydroxydecenoic acid, 3-hydroxydecenoyl-3-hydroxydecanoic acid, 3-hydroxydodecanoyl-3-hydroxydecanoic acid, 3-hydroxydecanoyl-3- hydroxydodecenoic acid, 3-hydroxydecanoyl-3-hydroxytetradecenoic acid, 3-hydroxytetradecanoyl-3-hydroxydecenoic acid, 3-hydroxydodecenoyl-3-hydroxydecanoic acid, 3-hydroxydecanoyl-3-hydroxytetradecanoic acid, 3-hydroxytetradecanoyl-3-hydroxydecanoic acid, 3-hydroxydecanoyl-3-hydroxytetradecenoic acid, 3-hydroxytetradecenoyl-3-hydroxydecanoic acid, 3-hydroxydodecanoyl-3-hydroxydodecanoic acid, 3-hydroxydodecenoyl-3-hydroxydodecanoic acid, 3-hydroxydodecanoyl-3-hydroxydodecenoic acid, 3-hydroxydodecanoyl-3-hydroxytetradecanoic acid, 3-hydroxytetradecanoyl-3-hydroxydodecanoic acid, 3-hydroxytetradecanoyl-3-hydroxytetradecanoic acid, 3-hydroxyhexadecanoyl-3-hydroxytetradecanoic acid, 3-hydroxytetradecanoyl-3-hydroxyhexadecanoic acid or 3-hydroxyhexadecanoyl-3-hydroxyhexadecanoic acid.

8. The method for producing rhamnolipids, comprising the method steps of
   I) contacting the cell according to claim 1, combining these measures as appropriate, with a medium containing a carbon source
   II) culturing the cell under conditions allowing the cell to make rhamnolipid from the carbon source and
   III) optionally isolating the rhamnolipids made.

* * * * *

SEQUENCE LISTING

```
<160> NUMBER OF SEQ ID NOS: 18

<210> SEQ ID NO 1
<211> LENGTH: 3272
<212> TYPE: DNA
<213> ORGANISM: Artificial Sequence
<220> FEATURE:
<223> OTHER INFORMATION: synthetic operon

<400> SEQUENCE: 1
ggcccaggag gggggatctg gcattttgg gaggtgtgaa atgcggcgcg aaagtctgtt      60
ggtatcggtt tgcaagggcc tgcgggtaca tgtcgagcgc gttgggcagg atcccgggcg    120
cagcacggtg atgctggtca acggcgcgat ggcgaccacc gcctcgttcg cccggacctg    180
caagtgcctg gccgaacatt tcaacgtggt gctgttcgac ctgcccttcg ccgggcagtc    240
gcgtcagcac aacccgcagc gggggttgat caccaaggac gacgaggtgg aaatcctcct    300
ggcgctgatc gagcgcttcg aggtcaatca cctggtctcc gcgtcctggg gcggtatctc    360
cacgctgctg gcgctgtcgc gcaatccgcg cggcatccgc agctcggtgg tgatggcatt    420
```

-continued

```
cgcccctgga ctgaaccagg cgatgctcga ctacgtcggg cgggcgcagg cgctgatcga      480
gctggacgac aagtcggcga tcggccatct gctcaacgag accgtcggca aatacctgcc      540
gccgcgcctg aaagccagca accatcagca catggcttcg ctggccaccg gcgaatacga      600
gcaggcgcgc tttcacatcg accaggtgct ggcgctcaac gatcgggct acctggcttg       660 cctggagcgg atccagagcc acgtgcattt catcaacggc agctgggacg aatacaccac      720
cgccgaggac gcccgccagt tccgcgacta cctgccgcac tgcagtttct cgcgggtgga      780
gggcaccggg catttcctcg acctggagtc caagctggcc gcggtacgcg tgcaccgcgc      840
cctgctcgag cacctgctga agcaaccgga gccgcagcgg gcggaacgcg cggcgggatt      900
ccacgagatg gccatcggct acgcctgaac ccttgacctg cgaagacccg gcctggccgg      960
gctttgcggt tgcataacgc acggagtagc accatgcacg ccatcctcat cgccatcggc     1020
tcggccggcg acgtatttcc cttcatcggc ctggcccgga ccctgaaatt gcgcgggcac     1080
cgcgtgagcc tctgcaccat cccggtgttt cgcgacgcgg tggagcagca cggcatcgcg     1140
ttcgtcccgc tgagcgacga actgacctac cgccggacca tgggcgatcc gcgcctgtgg     1200
gaccccaaga cgtccttcgg cgtgctctgg caaaccatcg ccgggatgat cgagccggtc     1260
tacgagtacg tctcggcgca gcgccatgac gacatcgtgg tggtcggctc gctctgggcg     1320
ctgggcgcac gcatcgctca cgagaagtac gggattccct acctgtccgc gcaggtctcg     1380
ccatcgacct tgttgtcggc gcacctgccg ccggtacacc ccaagttcaa cgtgcccgag     1440
cagatgccgc tggcgatgcg caagctgctc tggcgctgca tcgagcgctt caagctggat     1500
cgcacctgcg cgccggatat caacgcggtg cggcgcaagg tcggcctgga gacgccggtg     1560
aagcgcatct tcacccaatg gatgcattcg ccgcagggcg tggtctgcct gttcccggcc     1620
tggttcgcgc cgccccagca ggattggccg caacccctgc acatgaccgg cttcccgctg     1680
ttcgacggca gtatcccggg gaccccgctc gacgacgaac tgcaacgctt tctcgatcag     1740
ggcagccggc cgctggtgtt cacccagggc tcgaccgaac acctgcaggg cgacttctac     1800
gccatggccc tgcgcgcgct ggaacgcctc ggcgcgcgtg ggatcttcct caccggcgcc     1860
ggccaggaac cgctgcgcgg cttgccgaac cacgtgctgc agcgcgccta cgcgccactg     1920
ggagccttgc tgccatcgtg cgccgggctg gtccatccgg gcggtatcgg cgccatgagc     1980
ctggccttgg cggcggggt gccgcaggtg ctgctgccct cgcgccacga ccagttcgac     2040
aatgccgaac ggctggtccg gctcggctgc gggatgcgcc tgggcgtgcc attgcgcgag     2100
caggagttgc gcggggcgct gtggcgcttg ctcgaggacc cggccatggc ggcggcctgt     2160
cggcgtttca tggaattgtc acaaccgcac agtatcgctt gcggtaaagc ggcccaggtg     2220
gtcgaacgtt gtcataggga gggggatgcg cgatggctga aggctgcgtc ctgacctacg     2280
ggagaagaac gatcatggac cggatagaca tgggcgtgct ggtggtactg ttcaatcctg     2340
gcgacgacga cctggaacac cttggcgaac tggcggcggc gtttccgcaa ctgcgcttcc     2400
ttgccgtcga caactcaccg cacagcgatc cgcagcgcaa tgcccggctg cgcgggcaag     2460
gcatcgccgt gctgcaccac ggcaaccggc agggcatcgc cggcgccttc aaccagggac     2520
tcgacgcgct attccggcgt ggcgtgcagg gtgtgctgct gctcgaccag gactcccgtc     2580
ccggcggcgc cttcctcgcc gcccagtggc gcaacctgca ggcgcgcaac ggtcaggcct     2640
gcctgctcgg cccacggatc ttcgaccggg gtgaccggcg cttcctgccg gccatccatc     2700
tcgacggact gacgctcagg caattgtctc tggacggcct gacgacccg cagcgcacct      2760
```

| | |
|---|---|
| cgttcctgat ctcctccggc tgcctgctga cccgcgaggc ctaccagcgc ctcggccact | 2820 |
| tcgacgagga actgttcatc gaccacgtgg acaccgaata cagcctgcgc gcccaggcgc | 2880 |
| tggacgtgcc cctgtacgtc gacccgcggc tggtcctcga gcaccgcatc ggcacgcgca | 2940 |
| agacccgccg cctcggcggt ctcagcctca gcgcgatgaa ccacgccccg ctgcgccgct | 3000 |
| actacctggc gcgcaacggc ctgctggtcc tgcgccgcta cgcccggtcc tcgccgctgg | 3060 |
| ccctgctggc gaacctgccg accctgaccc agggcctcgc ggtgctcctg ctcgaacgcg | 3120 |
| acaagctgct caagctgcgc tgcctgggct ggggcctgtg gacggcctg cggggacgcg | 3180 |
| gcggcgcgct ggagaccaac cgcccgcgcc tgctgaagcg cctcgccggc ccggccgtgg | 3240 |
| cgtccgtagc ttccggcaag gccaaggcct ag | 3272 |

<210> SEQ ID NO 2
<211> LENGTH: 3413
<212> TYPE: DNA
<213> ORGANISM: Artificial Sequence
<220> FEATURE:
<223> OTHER INFORMATION: synthetic operon

<400> SEQUENCE: 2

| | |
|---|---|
| ttaattaaca ggaggaggta tgactcatga cgattctcgt gaccggcagc gccggcttca | 60 |
| tcggcgccaa tttcgtgctc gactggctgg ccctgcatga cgagccggtg gtcagcctcg | 120 |
| acaagctcac ctacgccggc aaccggcaga acctcgccag cctcgacggc gacgcccggc | 180 |
| acaccttcgt cgccggcgat atcggcgata ccagctggt agcccgcctg ctcgccgagc | 240 |
| accagccgcg ggcgatcctc aacttcgccg cggaatccca tgtggaccgc tcgatccacg | 300 |
| gccccgagga cttcatccag accaacatcg tcggcacctt ccgcctgctg aagaagtgc | 360 |
| gcgcctactg gggcgcgctg gagccggaag cgaaggcggc attccgcttc ctccacgtct | 420 |
| ccaccgacga agtctatggc tcgctggcac cgagcgatcc ggccttcacc gagaacaacc | 480 |
| gctacgagcc gaacagtccc tactcggcgt ccaaggcggc ctccgaccac ctagtgcggg | 540 |
| cctatcacca cacctatggg ctgccggtgc tgaccaccaa ctgctcgaac aactacggcc | 600 |
| cgtaccactt cccggaaaag ctcatcccac tggtgatcca caacgccctg ccggcaagc | 660 |
| cgctgccgat ctacggcgac ggccagcaga tccgcgactg gctctacgtc aaggaccatt | 720 |
| gcagcgccat ccgccgggtc ctcgaagccg gcaactggg cgagacctac aatgtcggcg | 780 |
| gctggaacga aaaggccaac ctcgacgtgg tcgagaccct ctgcgccatc ctcgaccagg | 840 |
| agcagccgcg cgccgacggc cgcagctatc gcgagcagat caccttcgtc aaggatcgtc | 900 |
| cgggccatga tcgccgctac gccatcgatg ccacgcgcct ggagcgcgag ctgggctgga | 960 |
| agccggcgga aaccttcgag accggcatcc gcaagaccgt cgcgctggta ctggacaacc | 1020 |
| aggactgggt ggccaacgta accagcggtg cctaccgcga gtgggtgggt aagcagtacg | 1080 |
| catgaaccgg atccttctcc tcggcgccaa cggccaggtc ggctgggagc tgcagcgcgc | 1140 |
| cctggcgccc ctgggcgaac tgctggtctg tgaccgtcgg cgcgccgatc tcgccgaccc | 1200 |
| cgaaggcctg gcgcgactgg ttcgcgccga gcggccgcag ttcatcgtca acgccggtgc | 1260 |
| ctacaccgcg gtggacaagg ccgagagcga tgccgacaac gcccgcctga tcaatgcccg | 1320 |
| cgccgtcgcg gtactggccg aggaggccgc ggcctgcggc gcctggctgg tgcattactc | 1380 |
| caccgactac gtgttcgacg gcgcgggcag cgtgccttc gccgaggacg cgccgaccgg | 1440 |
| cccgctgagc gtctacggc agaccaagct ggaaggcgag caggccatcc gcgccagcgg | 1500 |
| ctgccgccac ctgatcttcc gcaccagctg gtctacgcc gcgcgcggcg aaaacttcgc | 1560 |

-continued

```
caagaccatg ctgcgcctgg ccgggcaacg cgacgaactc aaggtcgtgg ccgaccagtt    1620
cggcgcgccc accagcgccg agctgatcgc cgacgtcacc gcccaggccc tgcagcgcct    1680
gtgctgggat gtcgagctgg cagcacgggc cagcggcacc taccacctgg tcgccagcgg    1740
cgagacgtcc tggcacctct atgcgcgctt cgtcatcgaa caggcgctgg agcggggctg    1800
ggagttgcag gcgacgccgc agcgggtcct gccgatcgcc accgaggact acccggtgcc    1860
ggcgaagcgt ccggccaatt cgcgcctcga caaccgcaag ctgcaacagg tcttcggcct    1920
ggtactgcca gactggcgct accatgccgg acgcatgatc caggaactga gcgagcaggg    1980
accactatga aacgcaaggg catcatcctc gccggaggct cgggcacccg cctgcacccg    2040
gcaacgctgg ccatctccaa gcagttgctg ccggtgtacg acaagccgat gatctactac    2100
ccgctcagta ccctgatgct ggcgggcatc cgcgagatac tgatcatctc gaccccacag    2160
gacaccccac gcttccagca gttgctgggc gacggttcga actggggcct ggacctgcaa    2220
tatgccgtgc aaccgtcgcc ggacggcctg gcccaggcct tcctgatcgg cgagtcgttc    2280
atcggcaacg acctcagcgc gctggtcctg ggcgacaacc tctattacgg ccacgacttc    2340
cacgagttgc tcggcagcgc ttcgcagcgc cagaccggcg ccagtgtctt cgcctaccac    2400
gtgctggacc cggagcgcta cggcgtggtc gagttcgacc agggcggcaa ggccatcagc    2460
ctggaagaga agccactgga gccgaagtcg aactacgcgg tcaccggcct gtatttctac    2520
gaccagcagg tggtggacat cgccagggac ctgaagcctt cgccgcgcgg cgagctggag    2580
atcaccgacg tcaaccgcgc ctatctggag cgcggccagc tcagcgtgga gatcatgggc    2640
cgcggctacg cctggctgga taccggcacc cacgattcgc tgctcgaggc cggccagttc    2700
atcgccaccc tggagaaccg ccagggtctc aaggtggcct gccggaagaa gatcgcctac    2760
cggcagaagt ggatcgacgc cgcgcaactg gaaaaactcg ccgcgccgct ggccaagaac    2820
ggctacggcc aataccctcaa cgcgcctgctg accgagaccg tgtactgatg aaagcgaccc    2880
gcctggcaat tcccgacgtc atcctcttcg aaccccgggt gttcggcgac gatcgcggat    2940
tcttcttcga aagctacaac cagcgcgcct tcgaggaagc ctgcggtcat ccggtcagct    3000
tcgtccagga caaccattcg cgttccgccc gtggcgtcct ccgcggcctg cactaccaga    3060
tccggcaagc cagggaaaaa ctggtgcgcg ccactctcgg cgaggtattc gacgtggccg    3120
tcgacctgcg tcgcggctcg ccgaccttcg gccagtgggg aggcgaacgc ctgagcgcg    3180 agaacaagcg ccagatgtgg attccggccg gcttcgcgca cggcttcgtg gtgctcagcg    3240
aatacgccga gttcctctac aagaccaccg acttctgggc gccggaacac gaacgctgca    3300
tcgtctggaa cgatcccgag ctgaagatcg actggccgct gcaggatgcc cccctgcttt    3360
cggagaagga ccgccagggc aaggcattcg ccgacgccga ctgcttcccc tga            3413
```

<210> SEQ ID NO 3
<211> LENGTH: 2028
<212> TYPE: DNA
<213> ORGANISM: Artificial Sequence
<220> FEATURE:
<223> OTHER INFORMATION: Promtor

<400> SEQUENCE: 3

```
ttaatctttc tgcgaattga gatgacgcca ctggctgggc gtcatcccgg tttcccgggt      60
aaacaccacc gaaaaatagt tactatcttc aaagccacat tcggtcgaaa tatcactgat     120
taacaggcgg ctatgctgga gaagatattg cgcatgcaca actctgacct gtcgcagata     180
```

```
ttgattgatg tcattccag tctgctggcg aaattgctga cgcaaaacgc gctcactgca    240
cgatgcctca tcacaaaatt tatccagcgc aaagggactt ttcaggctag ccgccagccg    300
ggtaatcagc ttatccagca acgtttcgct ggatgttggc ggcaacgaat cactggtgta    360
acgatggcga ttcagcaaca tcaccaactg cccgaacagc aactcagcca tttcgttagc    420
aaacggcaca tgctgactac tttcatgctc aagctgaccg ataacctgcc gcgcctgcgc    480 catcccatg ctacctaagc gccagtgtgg ttgccctgcg ctggcgttaa atcccggaat    540
cgccccctgc cagtcaagat tcagcttcag acgctccggg caataaataa tattctgcaa    600
aaccagatcg ttaacggaag cgtaggagtg tttatcgtca gcatgaatgt aaaagagatc    660
gccacgggta atgcgataag ggcgatcgtt gagtacatgc aggccattac cgcgccagac    720
aatcaccagc tcacaaaaat catgtgtatg ttcagcaaag acatcttgcg gataacggtc    780
agccacagcg actgcctgct ggtcgctggc aaaaaaatca tctttgagaa gttttaactg    840
atgcgccacc gtggctacct cggccagaga acgaagttga ttattcgcaa tatggcgtac    900
aaatacgttg agaagattcg cgttattgca gaaagccatc ccgtccctgg cgaatatcac    960
gcggtgacca gttaaactct cggcgaaaaa gcgtcgaaaa gtggttactg tcgctgaatc    1020
cacagcgata ggcgatgtca gtaacgctgg cctcgctgtg gcgtagcaga tgtcgggctt    1080
tcatcagtcg caggcggttc aggtatcgct gaggcgtcag tcccgtttgc tgcttaagct    1140
gccgatgtag cgtacgcagt gaaagagaaa attgatccgc cacggcatcc caattcacct    1200
catcggcaaa tggtcctcc agccaggcca gaagcaagtt gagacgtgat gcgctgtttt    1260
ccaggttctc ctgcaaactg cttttacgca gcaagagcag taattgcata acaagatct    1320 cgcgactggc ggtcgagggt aaatcatttt ccccttcctg ctgttccatc tgtgcaacca    1380
gctgtcgcac ctgctgcaat acgctgtggt taacgcgcca gtgagacgga tactgcccat    1440
ccagctcttg tggcagcaac tgattcagcc cggcgagaaa ctgaaatcga tccggcgagc    1500
gatacagcac attggtcaga cacagattat cggtatgttc atacagatgc cgatcatgat    1560
cgcgtacgaa acagaccgtg ccaccggtga tggtataggg ctgcccatta acacatgaa    1620 tacccgtgcc atgttcgaca atcacaattt catgaaaatc atgatgatgt tcaggaaaat    1680
ccgcctgcgg gagccggggt tctatcgcca cggacgcgtt accagacgga aaaaatcca    1740 cactatgtaa tacggtcata ctggcctcct gatgtcgtca acacggcgaa atagtaatca    1800
cgaggtcagg ttcttacctt aaattttcga cggaaaacca cgtaaaaaac gtcgattttt    1860
caagatacag cgtgaatttt caggaaatgc ggtgagcatc acatcaccac aattcagcaa    1920
attgtgaaca tcatcacgtt catctttccc tggttgccaa tggcccattt tcctgtcagt    1980
aacgagaagg tcgcgaattc aggcgctttt tagactggtc gtaatgaa              2028
```

<210> SEQ ID NO 4
<211> LENGTH: 1181
<212> TYPE: DNA
<213> ORGANISM: Artificial Sequence
<220> FEATURE:
<223> OTHER INFORMATION: Promotor

<400> SEQUENCE: 4

```
ttatgacaac ttgacggcta catcattcac ttttttcttca caaccggcac ggaactcgct     60
cgggctggcc ccggtgcatt ttttaaatac ccgcgagaaa tagagttgat cgtcaaaacc    120
aacattgcga ccgacggtgg cgataggcat ccgggtggtg ctcaaaagca gcttcgcctg    180
gctgatacgt tggtcctcgc gccagcttaa gacgctaatc cctaactgct ggcggaaaag    240
```

```
atgtgacaga cgcgacggcg acaagcaaac atgctgtgcg acgctggcga tatcaaaatt    300
gctgtctgcc aggtgatcgc tgatgtactg acaagcctcg cgtacccgat tatccatcgg    360
tggatggagc gactcgttaa tcgcttccat gcgccgcagt aacaattgct caagcagatt    420
tatcgccagc agctccgaat agcgcccttc cccttgcccg cgttaatgca tttgcccaaa    480
caggtcgctg aaatgcggct ggtgcgcttc atccgggcga agaaccccg tattggcaaa     540 tattgacggc cagttaagcc attcatgcca gtaggcgcgc ggacgaaagt aaacccactg    600
gtgataccat cgcgagcct ccggatgacg accgtagtga tgaatctctc ctggcgggaa     660
cagcaaaata tcacccggtc ggcaaacaaa ttctcgtccc tgattttca ccacccctg      720 accgcgaatg gtgagattga aatataacc tttcattccc agcggtcggt cgataaaaaa     780
atcgagataa ccgttggcct caatcggcgt taaacccgcc accagatggg cattaaacga    840
gtatcccggc agcaggggat cattttgcgc ttcagccata ctttcatac tcccgccatt     900 cagagaagaa accaattgtc catattgcat cagacattgc cgtcactgcg tcttttactg    960
gctcttctcg ctaaccaaac cggtaacccc gcttattaaa agcattctgt aacaaagcgg   1020
gaccaaagcc atgacaaaaa cgcgtaacaa aagtgtctat aatcacggca gaaagtcca    1080 cattgattat ttgcacggcg tcacactttg ctatgccata gcattttat ccataagatt    1140 agcggatcct acctgacgct ttttatcgca actctctact g                       1181

<210> SEQ ID NO 5
<211> LENGTH: 107
<212> TYPE: DNA
<213> ORGANISM: Artificial Sequence
<220> FEATURE:
<223> OTHER INFORMATION: Terminator

<400> SEQUENCE: 5
caaataaaac gaaaggctca gtcgaaagac tgggcctttc gttttatctg ttgtttgtcg     60
gtgaacgctc tcctgagtag gacaaatccg ccgggagcgg atttgaa                  107

<210> SEQ ID NO 6
<211> LENGTH: 17337
<212> TYPE: DNA
<213> ORGANISM: Artificial Sequence
<220> FEATURE:
<223> OTHER INFORMATION: Vector

<400> SEQUENCE: 6
cacaaaattc ctgcaggggc cggcccagcg ccggcggtcg agtggcgacg gcgcggcttg     60
tccgcgccct ggtagattgc ctggccgtag gccagccatt tttgagcggc cagcggccgc   120
gataggccga cgcgaagcgg cggggcgtag ggagcgcagc gaccgaaggg taggcgcttt   180
ttgcagctct tcggctgtgc gctggccaga cagttatgca caggccaggc gggttttaag   240
agttttaata gttttaaag agttttaggc ggaaaaatcg cctttttct cttttatatc     300 agtcacttac atgtgtgacc ggttcccaat gtacggcttt gggttcccaa tgtacgggtt   360
ccggttccca atgtacggct ttgggttccc aatgtacgtg ctatccacag gaaagagacc   420
ttttcgacct ttttccctg ctagggcaat tgcccctage atctgctccg tacattagga    480
accggcggat gcttcgccct cgatcaggtt gcggtagcgc atgactagga tcgggccagc   540
ctgccccgcc tcctccttca aatcgtactc cggcaggtca tttgacccga tcagcttgcg   600
cacggtgaaa cagaacttct tgaactctcc ggcgctgcca ctgcgttcgt agatcgtctt   660
```

```
gaacaaccat ctggcttctg ccttgcctgc ggcgcggcgt gccaggcggt agagaaaacg     720
gccgatgccg ggatcgatca aaaagtaatc ggggtgaacc gtcagcacgt ccgggttctt     780
gccttctgtg atctcgcggt acatccaatc aactagctcg atctcgatgt actccggccg    840
cccggtttcg ctctttacga tcttgtagcg gctaatcaag gcttcaccct cggataccgt    900
caccaggcgg ccgttcttgg ccttcttcgt acgctgcatg gcaacgtgcg tggtgtttaa    960
ccgaatgcag gtttctacca ggtcgtcttt ctgctttccg ccatcggctc gccggcagaa   1020
cttgagtacg tccgcaacgt gtggacggaa cacgcggccg gcttgtctc ccttcccttc    1080
ccggtatcgg ttcatggatt cggttagatg gaaaccgcc atcagtacca ggtcgtaatc    1140
ccacacactg gccatgccgg ccggccctgc ggaaacctct acgtgccgt ctggaagctc    1200
gtagcggatc acctcgccag ctcgtcggtc acgcttcgac agacggaaaa cggcacgtc    1260
catgatgctg cgactatcgc gggtgcccac gtcatagagc atcggaacga aaaaatctgg   1320
ttgctcgtcg cccttgggcg gcttcctaat cgacggcgca ccggctgccg gcggttgccg   1380
ggattctttg cggattcgat cagcggccgc ttgccacgat tcaccggggc gtgcttctgc   1440
ctcgatgcgt tgccgctggg cggcctgcgc ggccttcaac ttctccacca ggtcatcacc   1500
cagcgccgcg ccgatttgta ccgggccgga tggtttgcga ccgctcacgc cgattcctcg   1560
ggcttggggg ttccagtgcc attgcagggc cggcagacaa cccagccgct tacgcctggc   1620
caaccgcccg ttcctccaca catggggcat tccacggcgt cggtgcctgg ttgttcttga   1680
ttttccatgc cgcctccttt agccgctaaa attcatctac tcatttattc atttgctcat   1740
ttactctggt agctgcgcga tgtattcaga tagcagctcg gtaatggtct tgccttggcg   1800
taccgcgtac atcttcagct tggtgtgatc ctccgccggc aactgaaagt tgacccgctt   1860
catggctggc gtgtctgcca ggctggccaa cgttgcagcc ttgctgctgc gtgcgctcgg   1920
acggccggca cttagcgtgt ttgtgctttt gctcattttc tctttacctc attaactcaa   1980
atgagttttg atttaatttc agcggccagc gcctggacct cgcgggcagc gtcgccctcg   2040
ggttctgatt caagaacggt tgtgccggcg gcggcagtgc ctgggtagct cacgcgctgc   2100
gtgatacggg actcaagaat gggcagctcg taccggccca gcgcctcggc aacctcaccg   2160
ccgatgcgcg tgcctttgat cgcccgcgac acgacaaagg ccgcttgtag ccttccatcc   2220
gtgacctcaa tgcgctgctt aaccagctcc accaggtcgg cggtggccca tatgtcgtaa   2280
gggcttggct gcaccggaat cagcacgaag tcggctgcct tgatcgcgga cacagccaag   2340
tccgccgcct ggggcgctcc gtcgatcact acgaagtcgc gccggccgat ggccttcacg   2400
tcgcggtcaa tcgtcgggcg gtcgatgccg acaacggtta gcggttgatc ttcccgcacg   2460
gccgcccaat cgcgggcact gccctgggga tcggaatcga ctaacagaac atcgccccg    2520
gcgagttgca gggcgcgggc tagatgggtt gcgatggtcg tcttgcctga cccgcctttc    2580
tggttaagta cagcgataac cttcatgcgt tccccttgcg tatttgttta tttactcatc    2640
gcatcatata cgcagcgacc gcatgacgca agctgtttta ctcaaataca catcacctt    2700
ttagacggcg gcgctcggtt tcttcagcgg ccaagctggc cggccaggcc gccagcttgg    2760
catcagacaa accggccagg attttcatgca gccgcacggt tccggatgag cattcatcag   2820
gcgggcaaga atgtgaataa aggccggata aaacttgtgc ttatttttct ttacggtctt    2880
taaaaaggcc gtaatatcca gctgaacggt ctggttatag gtacattgag caactgactg    2940
aaatgcctca aaatgttctt tacgatgcca ttgggatata tcaacggtgg tatatccagt    3000
gatttttttc tccatttag cttccttagc tcctgaaaat ctcgataact caaaaaatac     3060
```

```
gcccggtagt gatcttattt cattatggtg aaagttggaa cctcttacgt gccgatcaac    3120
gtctcatttt cgccaaaagt tggcccaggg cttcccggta tcaacaggga caccaggatt    3180
tatttattct gcgaagtgat cttccgtcac aggtatttat tcggcgcaaa gtgcgtcggg    3240
tgatgctgcc aacttactga tttagtgtat gatggtgttt ttgaggtgct ccagtggctt    3300
ctgtttctat cagctgtccc tcctgttcag ctactgacgg ggtggtgcgt aacggcaaaa    3360
gcaccgccgg acatcagcgc tagcggagtg tatactggct tactatgttg cactgatga    3420 gggtgtcagt gaagtgcttc atgtggcagg agaaaaaagg ctgcaccggt gcgtcagcag    3480
aatatgtgat acaggatata ttccgcttcc tcgctcactg actcgctacg ctcggtcgtt    3540
cgactgcggc gagcggaaat ggcttacgaa cggggcggag atttcctgga agatgccagg    3600
aagatactta acagggaagt gagagggccg cggcaaagcc gttttttccat aggctccgcc    3660 cccctgacaa gcatcacgaa atctgacgct caaatcagtg gtggcgaaac ccgacaggac    3720
tataaagata ccaggcgttt ccccctggcg gctccctcgt gcgctctcct gttcctgcct    3780
ttcggtttac cggtgtcatt ccgctgttat ggccgcgttt gtctcattcc acgcctgaca    3840
ctcagttccg ggtaggcagt tcgctccaag ctggactgta tgcacgaacc ccccgttcag    3900
tccgaccgct gcgccttatc cggtaactat cgtcttgagt ccaacccgga aagacatgca    3960
aaagcaccac tggcagcagc cactggtaat tgatttagag gagttagtct tgaagtcatg    4020
cgccggttaa ggctaaactg aaaggacaag ttttggtgac tgcgctcctc caagccagtt    4080
acctcggttc aaagagttgg tagctcagag aaccttcgaa aaaccgcccct gcaaggcggt    4140 ttttttcgttt tcagagcaag agattacgcg cagaccaaaa cgatctcaag aagatcatct    4200
tattaatcag ataaaatatt tctagatttc agtgcaattt atctcttcaa atgtagcacc    4260
tgaagtcagc cccatacgat ataagttgta attctcatgt ttgacagctt atcatcgata    4320
agctttaatg cggtagttta tcacagttaa attgctaacg cagtcaggca ccgtgtatga    4380
aatctaacaa tgcgctcatc gtcatcctcg gcaccgtcac cctggatgct gtaggcatag    4440
gcttggttat gccggtactg ccgggcctct tgcgggatat cgtccattcc gacagcatcg    4500
ccagtcacta tggcgtgctg ctagcgctat atgcgttgat gcaatttcta tgcgcacccg    4560
ttctcggagc actgtccgac cgctttggcc gccgcccagt cctgctcgct tcgctacttg    4620
gagccactat cgactacgcg atcatggcga ccacacccgt cctgtggatc ctctacgccg    4680
gacgcatcgt ggccggcatc accggcgcca caggtgcggt tgctggcgcc tatatcgccg    4740
acatcaccga tggggaagat cgggctcgcc acttcgggct catgagcgct tgtttcggcg    4800
tgggtatggt ggcaggcccc gtggccgggg gactgttggg cgccatctcc ttgcatgcac    4860
cattccttgc ggcggcggtg ctcaacggcc tcaacctact actgggctgc ttcctaatgc    4920
aggagtcgca taagggagag cgtcgaccga tgcccttgag agccttcaac ccagtcagct    4980
ccttccggtg ggcgcgggc atgactatcg tcgccgcact tatgactgtc ttctttatca    5040
tgcaactcgt aggacaggtg ccggcagcgc tctgggtcat tttcggcgag gaccgctttc    5100
gctggagcgc gacgatgatc ggcctgtcgc ttgcggtatt cggaatcttg cacgccctcg    5160
ctcaagcctt cgtcactggt cccgccacca acgtttcgg cgagaagcag gccattatcg    5220
ccggcatggc ggccgacgcg ctgggctacg tcttgctggc gttcgcgacg cgaggctgga    5280
tggccttccc cattatgatt cttctcgctt ccggcggcat cgggatgccc gcgttgcagg    5340
ccatgctgtc caggcaggta gatgacgacc atcagggaca gcttcaagga tcgctcgcgg    5400
```

```
ctcttaccag cctaacttcg atcattggac cgctgatcgt cacggcgatt tatgccgcct    5460
cggcgagcac atggaacggg ttggcatgga ttgtaggcgc cgccctatac cttgtctgcc    5520
tccccgcgtt gcgtcgcggt gcatggagcc gggccacctc gacctgaatg gaagccggcg    5580
gcacctcgct aacggattca ccactccaag aattggagcc aatcaattct gcggagaac     5640 tgtgaatgcg caaaccaacc cttggcagaa catatccatc gcgtccgcca tctccagcag    5700
ccgcacgcgg cgcatctcgg gcagcgttgg gtcctggcca cgggtgcgca tgatcgtgct    5760
cctgtcgttg aggacccggc taggctggcg gggttgcctt actggttagc agaatgaatc    5820
accgatacgc gagcgaacgt gaagcgactg ctgctgcaaa cgtctgcga cctgagcaac     5880 aacatgaatg gtcttcggtt tccgtgtttc gtaaagtctg gaaacgcgga agtccctac     5940 gtgctgctga gttgcccgc aacagagagt ggaaccaacc ggtgatacca cgatactatg     6000
actgagagtc aacgccatga gcggcctcat ttcttattct gagttacaac agtccgcacc    6060
gctgtccggt agctccttcc ggtgggcgcg gggcatgact atcgtcgccg cacttatgac    6120
tgtcttcttt atcatgcaac tcgtaggaca ggtgccggca gcgcccaaca gtccccggc    6180 cacggggcct gccaccatac ccacgccgaa acaagcgccc tgcaccatta tgttccggat    6240
ctgcatcgca ggatgctgct ggctaccctg tggaacacct acatctgtat taacgaagcg    6300
ctaaccgttt ttatcaggct ctgggaggca gaataaatga tcatatcgtc aattattacc    6360
tccacgggga gagcctgagc aaactggcct caggcatttg agaagcacac ggtcacactg    6420
cttccggtag tcaataaacc ggtaaaccag caatagacat aagcggctat ttaacgaccc    6480
tgccctgaac cgacgaccgg gtcgaatttg ctttcgaatt tctgccattc atccgcttat    6540
tatcacttat tcaggcgtag caccaggcgt ttaagggcac caataactgc cttaaaaaaa    6600
ttacgccccg ccctgccact catcgcagta ctgttgtaat tcattaagca ttctgccgac    6660
atggaagcca tcacaaacgg catgatgaac ctgaatcgcc agcggcatca gcaccttgtc    6720
gccttgcgta taatatttgc ccatggattt aaatttaatc tttctgcgaa ttgagatgac    6780
gccactggct gggcgtcatc ccggtttccc gggtaaacac caccgaaaaa tagttactat    6840
cttcaaagcc acattcggtc gaaatatcac tgattaacag gcggctatgc tggagaagat    6900
attgcgcatg acacactctg acctgtcgca gatattgatt gatggtcatt ccagtctgct    6960
ggcgaaattg ctgacgcaaa acgcgctcac tgcacgatgc ctcatcacaa aatttatcca    7020
gcgcaaaggg acttttcagg ctagccgcca gccgggtaat cagcttatcc agcaacgttt    7080
cgctggatgt tggcggcaac gaatcactgg tgtaacgatg gcgattcagc aacatcacca    7140
actgcccgaa cagcaactca gccatttcgt tagcaaacgg cacatgctga ctactttcat    7200
gctcaagctg accgataacc tgccgcgcct gcgccatccc catgctacct aagcgccagt    7260
gtggttgccc tgcgctggcg ttaaatcccg gaatcgcccc ctgccagtca agattcagct    7320
tcagacgctc cgggcaataa ataatattct gcaaaaccag atcgttaacg gaagcgtagg    7380
agtgtttatc gtcagcatga atgtaaaaga gatcgccacg ggtaatgcga taagggcgat    7440
cgttgagtac atgcaggcca ttaccgcgcc agacaatcac cagctcacaa aaatcatgtg    7500
tatgttcagc aaagacatct gcggataac ggtcagccac agcgactgcc tgctggtcgc     7560
tggcaaaaaa atcatctttg agaagtttta actgatgcgc caccgtggct acctcggcca    7620
gagaacgaag ttgattattc gcaatatggc gtacaaatac gttgagaaga ttcgcgttat    7680
tgcagaaagc catcccgtcc ctggcgaata tcacgcggtg accagttaaa ctctcggcga    7740
aaaagcgtcg aaaagtggtt actgtcgctg aatccacagc gataggcgat gtcagtaacg    7800
```

```
ctggcctcgc tgtggcgtag cagatgtcgg gctttcatca gtcgcaggcg gttcaggtat    7860
cgctgaggcg tcagtcccgt ttgctgctta agctgccgat gtagcgtacg cagtgaaaga    7920
gaaaattgat ccgccacggc atcccaattc acctcatcgg caaaatggtc ctccagccag    7980
gccagaagca agttgagacg tgatgcgctg ttttccaggt tctcctgcaa actgctttta    8040
cgcagcaaga gcagtaattg cataaacaag atctcgcgac tggcggtcga gggtaaatca    8100 ttttccccctt cctgctgttc catctgtgca accagctgtc gcacctgctg caatacgctg    8160
tggttaacgc gccagtgaga cggatactgc ccatccagct cttgtggcag caactgattc    8220
agcccggcga gaaactgaaa tcgatccggc gagcgataca gcacattggt cagacacaga    8280
ttatcggtat gttcatacag atgccgatca tgatcgcgta cgaaacagac cgtgccaccg    8340
gtgatggtat agggctgccc attaaacaca tgaatacccg tgccatgttc gacaatcaca    8400
atttcatgaa aatcatgatg atgttcagga aaatccgcct gcgggagccg gggttctatc    8460 gccacgacg cgttaccaga cggaaaaaaa tccacactat gtaatacggt catactggcc    8520
tcctgatgtc gtcaacacgg cgaaatagta atcacgaggt caggttctta ccttaaattt    8580
tcgacggaaa accacgtaaa aaacgtcgat ttttcaagat acagcgtgaa ttttcaggaa    8640
atgcggtgag catcacatca ccacaattca gcaaattgtg aacatcatca cgttcatctt    8700
tccctggttg ccaatggccc attttcctgt cagtaacgag aaggtcgcga attcaggcgc    8760
tttttagact ggtcgtaatg aacatttaaa tgaattccct tgggactcta gagatccgcg    8820
ggggcccagg aggggggatc tggcattttt gggaggtgtg aaatgcggcg cgaaagtctg    8880
ttggtatcgg tttgcaaggg cctgcgggta catgtcgagc gcgttgggca ggatcccggg    8940
cgcagcacgg tgatgctggt caacggcgcg atggcgacca ccgcctcgtt cgcccggacc    9000
tgcaagtgcc tggccgaaca tttcaacgtg gtgctgttcg acctgccctt cgccgggcag    9060
tcgcgtcagc acaacccgca gcggggttg atcaccaagg acgacgaggt ggaaatcctc    9120
ctggcgctga tcgagcgctt cgaggtcaat cacctggtct ccgcgtcctg ggcggtatc    9180 tccacgctgc tggcgctgtc gcgcaatccg cgcggcatcc gcagctcggt ggtgatggca    9240
ttcgcccctg gactgaacca ggcgatgctc gactacgtcg ggcgggcgca ggcgctgatc    9300
gagctggacg acaagtcggc gatcggccat ctgctcaacg agaccgtcgg caaatacctg    9360
ccgccgcgcc tgaaagccag caaccatcag cacatggctt cgctggccac cggcgaatac    9420
gagcaggcgc gctttcacat cgaccaggtg ctggcgctca cgatcggggg ctacctggct    9480
tgcctggagc ggatccagag ccacgtgcat ttcatcaacg gcagctggga cgaatacacc    9540
accgccgagg acgcccgcca gttccgcgac tacctgccgc actgcagttt ctcgcgggtg    9600
gagggcaccg gcatttcct cgacctggag tccaagctgg ccgcgtacg cgtgcaccgc    9660 gccctgctcg agcacctgct gaagcaaccg gagccgcagc gggcggaacg cgcggcggga    9720
ttccacgaga tggccatcgg ctacgcctga acccttgacc tgcgaagacc cggcctggcc    9780
gggctttgcg gttgcataac gcacggagta gcaccatgca cgccatcctc atcgccatcg    9840
gctcggccgg cgacgtattt cccttcatcg gcctggcccg gaccctgaaa ttgcgcgggc    9900
accgcgtgag cctctgcacc atcccggtgt ttcgcgacgc ggtggagcag cacggcatcg    9960
cgttcgtccc gctgagcgac gaactgacct accgccggac catgggcgat ccgcgcctgt   10020
gggaccccaa gacgtccttc ggcgtgctct ggcaaaccat cgccgggatg atcgagccgg   10080
tctacgagta cgtctcggcg cagcgccatg acgacatcgt ggtggtcggc tcgctctggg   10140
```

```
cgctgggcgc acgcatcgct cacgagaagt acgggattcc ctacctgtcc gcgcaggtct   10200
cgccatcgac cttgttgtcg gcgcacctgc cgccggtaca ccccaagttc aacgtgcccg   10260
agcagatgcc gctggcgatg cgcaagctgc tctggcgctg catcgagcgc ttcaagctgg   10320
atcgcacctg cgcgccggat atcaacgcgg tgcggcgcaa ggtcggcctg agacgccgg    10380 tgaagcgcat cttcacccaa tggatgcatt cgccgcaggg cgtggtctgc ctgttcccgg   10440
cctggttcgc gccgcccag caggattggc cgcaacccct gcacatgacc ggcttcccgc    10500
tgttcgacgg cagtatcccg ggacccgc tcgacgacga actgcaacgc tttctcgatc     10560
agggcagccg gccgctggtg ttcacccagg gctcgaccga acacctgcag gcgacttct    10620 acgccatggc cctgcgcgcg ctggaacgcc tcggcgcgcg tgggatcttc ctcaccggcg   10680
ccggccagga accgctgcgc ggcttgccga accacgtgct gcagcgcgcc tacgcgccac   10740
tgggagcctt gctgccatcg tgcgccgggc tggtccatcc gggcggtatc ggcgccatga   10800
gcctggcctt ggcggcgggg gtgccgcagg tgctgctgcc ctgcgcccac gaccagttcg   10860
acaatgccga acggctggtc cggctcggct gcgggatgcg cctgggcgtg ccattgcgcg   10920
agcaggagtt gcgcggggcg ctgtggcgct tgctcgagga cccggccatg gcggcggcct   10980
gtcggcgttt catggaattg tcacaaccgc acagtatcgc ttgcgtaaa gcggcccagg    11040 tggtcgaacg ttgtcatagg gaggggatg cgcgatggct gaaggctgcg tcctgaccta    11100
cgggagaaga acgatcatgg accgataga catgggcgtg ctggtggtac tgttcaatcc    11160
tggcgacgac gacctggaac accttggcga actggcggcg gcgtttccgc aactgcgctt    11220
ccttgccgtc gacaactcac cgcacagcga tcccagcgc aatgcccggc tgcgcgggca    11280
aggcatcgcc gtgctgcacc acggcaaccg gcagggcatc gccggcgcct tcaaccaggg   11340
actcgacgcg ctattccggc gtggcgtgca gggtgtgctg ctgctcgacc aggactcccg    11400
tcccggcggc gccttcctcg ccgcccagtg gcgcaacctg caggcgcgca acggtcaggc    11460
ctgcctgctc ggcccacgga tcttcgaccg gggtgaccgg cgcttcctgc cggccatcca    11520
tctcgacgga ctgacgctca ggcaattgtc tctggacggc ctgacgaccc cgcagcgcac    11580
ctcgttcctg atctcctccg gctgcctgct gacccgcgag gcctaccagc gcctcggcca    11640
cttcgacgag gaactgttca tcgaccacgt ggacaccgaa tacagcctgc gcgcccaggc    11700
gctggacgtg cccctgtacg tcgacccgcg gctggtcctc gagcaccgca tcggcacgcg    11760
caagacccgc cgcctcggcg gtctcagcct cagcgcgatg aaccacgccc cgctgcgccg    11820
ctactacctg gcgcgcaacg gcctgctggt cctgcgccgc tacgcccggt cctcgccgct    11880
ggccctgctg gcgaacctgc cgaccctgac ccagggcctc gcggtgctcc tgctcgaacg    11940
cgacaagctc tcaagctgc gctgcctggg ctggggcctg tgggacgcc tgcggggacg     12000 cggcggcgcg ctggagacca accgcccgcg cctgctgaag cgcctcgccg gcccggccgt    12060
ggcgtccgta gcttccggca aggccaaggc ctagtcggcg aaacgcattc cctctagagt    12120
ttaaacacca ggtgcgatcg cgcggccgcg ctcgagcacg cgagagtagg gaactgccag    12180
gcatcaaata aaacgaaagg ctcagtcgaa agactgggcc tttcgtttta tctgttgttt    12240
gtcggtgaac gctctcctga gtaggacaaa tccgccggga gcggatttga acgatgataa    12300
gctgtcaaac atgagaattc ttgaagacga aagggcctcg tgtgtacaat aatatttgcc    12360 catggatttta aataaccct tgctactccg tcaagccgtc aattgtctga ttcgttacca     12420
attatgacaa cttgacggct acatcattca ctttttcttc acaaccggca cggaactcgc    12480
tcgggctggc cccggtgcat ttttttaaata cccgcgagaa atagagttga tcgtcaaaac    12540
```

```
caacattgcg accgacggtg gcgataggca tccgggtggt gctcaaaagc agcttcgcct    12600
ggctgatacg ttggtcctcg cgccagctta agacgctaat ccctaactgc tggcggaaaa    12660
gatgtgacag acgcgacggc gacaagcaaa catgctgtgc gacgctggcg atatcaaaat    12720
tgctgtctgc caggtgatcg ctgatgtact gacaagcctc gcgtacccga ttatccatcg    12780
gtggatggag cgactcgtta atcgcttcca tgcgccgcag taacaattgc tcaagcagat    12840
ttatcgccag cagctccgaa tagcgccctt ccccttgccc ggcgttaatg atttgcccaa    12900
acaggtcgct gaaatgcggc tggtgcgctt catccgggcg aaagaacccc gtattggcaa    12960
atattgacgg ccagttaagc cattcatgcc agtaggcgcg cggacgaaag taaacccact    13020
ggtgatacca ttcgcgagcc tccggatgac gaccgtagtg atgaatctct cctggcggga    13080
acagcaaaat atcacccggt cggcaaacaa attctcgtcc ctgattttc accaccccct    13140 gaccgcgaat ggtgagattg agaatataac cttttcattcc cagcggtcgg tcgataaaaa    13200
aatcgagata accgttggcc tcaatcggcg ttaaacccgc caccagatgg gcattaaacg    13260
agtatcccgg cagcagggga tcattttgcg cttcagccat acttttcata ctcccgccat    13320
tcagagaaga aaccaattgt ccatattgca tcagacattg ccgtcactgc gtcttttact    13380
ggctcttctc gctaaccaaa ccggtaaccc cgcttattaa aagcattctg taacaaagcg    13440
ggaccaaagc catgacaaaa acgcgtaaca aaagtgtcta taatcacggc agaaaagtcc    13500
acattgatta tttgcacggc gtcacacttt gctatgccat agcatttta tccataagat    13560 tagcggatcc tacctgacgc tttttatcgc aactctctac tgtttctcca tacccgattt    13620
aaatgaattc ccttgggact cttaattaac aggaggaggt atgactcatg acgattctcg    13680
tgaccggcag cgccggcttc atcgcgcca atttcgtgct cgactggctg gccctgcatg    13740
acgagccggt ggtcagcctc gacaagctca cctacgccgg caaccggcag aacctcgcca    13800
gcctcgacgg cgacgcccgg cacaccttcg tcgccggcga tatcggcgat agccagctgg    13860
tagcccgcct gctcgccgag caccagccgc gggcgatcct caacttcgcc gcggaatccc    13920
atgtggaccg ctcgatccac ggccccgagg acttcatcca gaccaacatc gtcggcacct    13980
tccgcctgct ggaagaagtg cgcgcctact ggggcgcgct ggagccggaa gcgaaggcgg    14040
cattccgctt cctccacgtc tccaccgacg aagtctatgg ctcgctggca ccgagcgatc    14100
cggccttcac cgagaacaac cgctacgagc cgaacagtcc ctactcggcg tccaaggcgg    14160
cctccgacca cctagtgcgg gcctatcacc acacctatgg gctgccggtg ctgaccacca    14220
actgctcgaa caactacggc ccgtaccact tcccggaaaa gctcatccca ctggtgatcc    14280
acaacgccct ggccggcaag ccgctgccga tctacggcga cggccagcag atccgcgact    14340
ggctctacgt caaggaccat tgcagcgcca tccgccgggt cctcgaagcc gggcaactgg    14400
gcgagaccta caatgtcggc ggctggaacg aaaaggccaa cctcgacgtg gtcgagaccc    14460
tctgcgccat cctcgaccag gagcagccgc gcgccgacgg ccgcagctat cgcgagcaga    14520
tcaccttcgt caaggatcgt ccgggccatg atcgccgcta cgccatcgat gccacgcgcc    14580
tggagcgcga gctgggctgg aagccggcgg aaaccttcga gaccggcatc cgcaagaccg    14640
tgcgctggta cctggacaac caggactggg tggccaacgt aaccagcggt gcctaccgcg    14700
agtgggtggg taagcagtac gcatgaaccg gatccttctc ctcggcgcca acggccaggt    14760
cggctgggag ctgcagcgcg ccctggcgcc gctgggcgaa ctgctggtct gtgaccgtcg    14820
gcgcgccgat ctcgccgacc ccgaaggcct ggcgcgactg gttcgcgccg agcggccgca    14880
```

```
gttcatcgtc aacgccggtg cctacaccgc ggtggacaag gccgagagcg atgccgacaa   14940
cgcccgcctg atcaatgccc gcgccgtcgc ggtactggcc gaggaggccg cggcctgcgg   15000
cgcctggctg gtgcattact ccaccgacta cgtgttcgac ggcgcgggca gcgtgccttt   15060
cgccgaggac gcgccgaccg gcccgctgag cgtctacggg cagaccaagc tggaaggcga   15120
gcaggccatc cgcgccagcg gctgccgcca cctgatcttc cgcaccagct gggtctacgc   15180
cgcgcgcggg ggaaacttcg ccaagaccat gctgcgcctg gccgggcaac gcgacgaact   15240
caaggtcgtg gccgaccagt cggcgcgcc caccagcgcc gagctgatcg ccgacgtcac   15300
cgcccaggcc ctgcagcgcc tgtgctggga tgtcgagctg gcagcacggg ccagcggcac   15360
ctaccacctg gtcgccagcg gcgagacgtc ctggcacctc tatgcgcgct tcgtcatcga   15420
acaggcgctg gagcggggct gggagttgca ggcgacgccg cagcgggtcc tgccgatcgc   15480
caccgaggac tacccggtgc cggcgaagcg tccggccaat tcgcgcctcg acaaccgcaa   15540
gctgcaacag gtcttcggcc tggtactgcc agactggcgc taccatgccg gacgcatgat   15600
ccaggaactg agcgagcagg gaccactatg aaacgcaagg gcatcatcct cgccggaggc   15660
tcgggcaccc gcctgcaccc ggcaacgctg gccatctcca gcagttgct gccggtgtac   15720
gacaagccga tgatctacta cccgctcagt accctgatgc tggcgggcat ccgcgagata   15780
ctgatcatct cgaccccaca ggacaccca cgcttccagc agttgctggg cgacggttcg   15840
aactggggcc tggacctgca atatgccgtg caaccgtcgc cggacggcct ggcccaggcc   15900
ttcctgatcg gcgagtcgtt catcggcaac gacctcagcg cgctggtcct gggcgacaac   15960
ctctattacg ccacgacctt ccacgagttg ctcggcagcg cttcgcagcg ccagaccggc   16020
gccagtgtct tcgcctacca cgtgctggac ccggagcgct acggcgtggt cgagttcgac   16080
cagggcggca aggccatcag cctggaagag aagccactgg agccgaagtc gaactacgcg   16140
gtcaccggcc tgtatttcta cgaccagcag gtggtggaca tcgccaggga cctgaagcct   16200
tcgccgcgcg gcgagctgga gatcaccgac gtcaaccgcg cctatctgga gcgcggccag   16260
ctcagcgtgg agatcatggg ccgcggctac gcctggctgg ataccggcac ccacgattcg   16320
ctgctcgagg ccgccagtt catcgccacc ctggagaacc gccagggtct caaggtggcc   16380
tgcccggaag agatcgccta ccggcagaag tggatcgacg ccgcgcaact ggaaaaactc   16440
gccgcgccgc tggccaagaa cggctacggc caatacctca gcgcctgct gaccgagacc   16500
gtgtactgat gaaagcgacc cgcctggcaa ttcccgacgt catcctcttc gaaccccggg   16560
tgttcggcga cgatcgcgga ttcttcttcg aaagctacaa ccagcgcgcc ttcgaggaag   16620
cctgcggtca tccggtcagc ttcgtccagg acaaccattc gcgttccgcc cgtggcgtcc   16680
tccgcggcct gcactaccag atccggcaag cccagggaaa actggtgcgc gccactctcg   16740
gcgaggtatt cgacgtggcc gtcgacctgc gtcgcggctc gccgaccttc ggccagtggg   16800
taggcgaacg cctgagcgcg gagaacaagc gccagatgtg gattccggcc ggcttcgcgc   16860
acggcttcgt ggtgctcagc gaatacgccg agttcctcta caagaccacc gacttctggg   16920
cgccggaaca cgaacgctgc atcgtctgga cgatcccga gctgaagatc gactggccgc   16980
tgcaggatgc cccctgcttt tcggagaagg accgccaggg caaggcattc gccgacgccg   17040
actgcttccc ctgaacggca gggagcgacc ggactcggcg caaggcgtgg taatttaggg   17100
tttaaacacc aggtgcgatc gcgcggccgc gctcgagcac gcgagagtag ggaactgcca   17160
ggcatcaaat aaaacgaaag gctcagtcga aagactgggc ctttcgtttt atctgttgtt   17220
tgtcggtgaa cgctctcctg agtaggacaa atccgccggg agcggatttg aacgatgata   17280
```
agctgtcaaa catgagaatt cttgaactag ttgtacaaac gttcgtcaaa agggcga        17337

<210> SEQ ID NO 7
<211> LENGTH: 32
<212> TYPE: DNA
<213> ORGANISM: Artificial Sequence
<220> FEATURE:
<223> OTHER INFORMATION: Primer

<400> SEQUENCE: 7
gccgctttgg tcccgggttt caagctcagc gg        32

<210> SEQ ID NO 8
<211> LENGTH: 32
<212> TYPE: DNA
<213> ORGANISM: Artificial Sequence
<220> FEATURE:
<223> OTHER INFORMATION: Primer

<400> SEQUENCE: 8
aaggcgcgat cgcgggttag aaactgctct gg        32

<210> SEQ ID NO 9
<211> LENGTH: 27
<212> TYPE: DNA
<213> ORGANISM: Artificial Sequence
<220> FEATURE:
<223> OTHER INFORMATION: Primer

<400> SEQUENCE: 9
ccgcgatcgc gccttgtgtc gcgtttc        27

<210> SEQ ID NO 10
<211> LENGTH: 33
<212> TYPE: DNA
<213> ORGANISM: Artificial Sequence
<220> FEATURE:
<223> OTHER INFORMATION: Primer

<400> SEQUENCE: 10
gcttgcatgc ctgcaatgcc gtaggctttg acc        33

<210> SEQ ID NO 11
<211> LENGTH: 679
<212> TYPE: DNA
<213> ORGANISM: Artificial Sequence
<220> FEATURE:
<223> OTHER INFORMATION: PCR product

<400> SEQUENCE: 11
gccgctttgg tcccgggttt caagctcagc ggcagcggca cccagggtgc ggtaatgccg        60
ttcgaactgg tatggacccc acgtatccaa ggcttgaaag gggaatatcg tgccggctac        120
tactacagta atgccaaggc acaagatgtt ctcaaggaca gcaacggtca gccgccgcc        180 ctcagcggcg ccgcctaccg cagcagttcg agcaagcacg gcttgtggat tggcgcccag        240
cagcaggtca cctcgctggc gtccgaccag tcgcgcggct tgagcgtgtt cgccaacgcc        300
acggtgcatg acaaaaagac caatgccatc gacaactatg tgcaggcagg actggtattc        360
aaagggcctt tcgatgcccg cgccaaggac gacatcggtt tcgccctggc ccgcgtgcac        420
gtcaaccctg cctatcgcaa gaacgcccgc ctggtcaacc aggccgccgg cctctatgac        480
tacgacaacc cgggcttcct gccagtgcag gacaccgagt acagcgccga gctgtattac        540

| | | |
|---|---|---|
| ggcattcact tggccgactg gctcacggta cgccccaacc tgcagtacat ccgccacccg | 600 | |
| ggcggggtgt cgcaggtcga tggcgccctg atcggcggcc tgaagatcca gagcagtttc | 660 | |
| taacccgcga tcgcgcctt | 679 | |

```
<210> SEQ ID NO 12
<211> LENGTH: 682
<212> TYPE: DNA
<213> ORGANISM: Artificial Sequence
<220> FEATURE:
<223> OTHER INFORMATION: PCR product

<400> SEQUENCE: 12
```

| | |
|---|---|
| ccgcgatcgc gccttgtgtc gcgtttcggt cgcgcagcgg ccccaacgat ctagaatgct | 60 |
| ggatggattc tggggctgct gcgcagccca atcgcgacac aaggctgctc ccgaaccatt | 120 |
| gaaacccatc cctccccgcc ccatctaagc accatagtca ttcacgcagg tgccccatga | 180 |
| gcgaccagca ggatttcccc gaacaccctg acgaacacag cgaagtcgaa cacaccctcc | 240 |
| aggccgaagt cagccacgcc ctcgccctgc cggtcaaca gctgccggac aaggtctacg | 300 |
| tcatcccgat ccacaaccgc ccgttcttcc cggcccaggt actgccggtg atcgtcaatg | 360 |
| aagagccctg ggccgaaacg ctcgacctgg tagccaagtc accggaccac tgcctggcgc | 420 |
| tgttcttcat ggacaccccg ccagaagacc accgccactt cgacacctcg gcactgccgc | 480 |
| agtacggcac gctggtcaag gtgcaccatg ccagccgcga aaacggcaaa ttgcagttcg | 540 |
| tcgcccaggg cctgtcccgg gtgcgcatcc gcaactggct caagcaccac cgcccgccct | 600 |
| acctggtcga agtcgaatac ccgcgccagc ccgccgagcc gaccgacgag gtcaaagcct | 660 |
| acggcattgc aggcatgcaa gc | 682 |

```
<210> SEQ ID NO 13
<211> LENGTH: 4831
<212> TYPE: DNA
<213> ORGANISM: Artificial Sequence
<220> FEATURE:
<223> OTHER INFORMATION: Vector

<400> SEQUENCE: 13
```

| | |
|---|---|
| atggcgcagg ggatcaagat ctgatcaaga acaggatga ggatcgtttc gcatgattga | 60 |
| acaagatgga ttgcacgcag gttctccggc cgcttgggtg gagaggctat tcggctatga | 120 |
| ctgggcacaa cagacaatcg gctgctctga tgccgccgtg ttccggctgt cagcgcaggg | 180 |
| gcgcccggtt cttttttgtca agaccgacct gtccggtgcc ctgaatgaac tgcaggacga | 240 |
| ggcagcgcgg ctatcgtggc tggccacgac gggcgttcct tgcgcagctg tgctcgacgt | 300 |
| tgtcactgaa gcgggaaggg actggctgct attgggcgaa gtgccggggc aggatctcct | 360 |
| gtcatctcac cttgctcctg ccgagaaagt atccatcatg gctgatgcaa tgcggcggct | 420 |
| gcatacgctt gatccggcta cctgcccatt cgaccaccaa gcgaaacatc gcatcgagcg | 480 |
| agcacgtact cggatggaag ccggtcttgt cgatcaggat gatctggacg aagagcatca | 540 |
| ggggctcgcg ccagccgaac tgttcgccag gctcaaggcg cgcatgcccg acggcgagga | 600 |
| tctcgtcgtg acccatggcg atgcctgctt gccgaatatc atggtggaaa atggccgctt | 660 |
| ttctggattc atcgactgtg gccggctggg tgtggcggac cgctatcagg acatagcgtt | 720 |
| ggctacccgt gatattgctg aagagcttgg cggcgaatgg gctgaccgct tcctcgtgct | 780 |
| ttacggtatc gccgctcccg attcgcagcg catcgccttc tatcgccttc ttgacgagtt | 840 |
| cttctgagcg ggactctggg gttcgaaatg accgaccaag cgacgcccaa cctgccatca | 900 |

```
cgagatttcg attccaccgc cgccttctat gaaaggttgg gcttcggaat cgttttccgg      960
gacgccggct ggatgatcct ccagcgcggg gatctcatgc tggagttctt cgcccacccc     1020
gggctcgatc ccctcgcgag ttggttcagc tgctgcctga ggctggacga cctcgcggag     1080
ttctaccggc agtgcaaatc cgtcggcatc caggaaacca gcagcggcta ccgcgcatc      1140 catgcccccg aactgcagga gtggggaggc acgatggccg ctttggtccc ggatcctcta     1200
gagtcgacct gcaggcatgc aagcttggcg taatcatggt catagctgtt tcctgtgtga     1260
aattgttatc cgctcacaat tccacacaac atacgagccg gaagcataaa gtgtaaagcc     1320
tggggtgcct aatgagtgag ctaactcaca ttaattgcgt tgcgctcact gcccgctttc     1380
cagtcgggaa acctgtcgtg ccagctgcat taatgaatcg gccaacgcgc ggggagaggc     1440
ggtttgcgta ttgggcgctc ttccgcttcc tcgctcactg actcgctgcg ctcggtcgtt     1500
cggctgcggc gagcggtatc agctcactca aaggcggtaa tacggttatc cacagaatca     1560
ggggataacg caggaaagaa catgtgagca aaaggccagc aaaaggccag gaaccgtaaa     1620
aaggccgcgt tgctggcgtt tttccatagg ctccgccccc ctgacgagca tcacaaaaat     1680
cgacgctcaa gtcagaggtg gcgaaacccg acaggactat aaagatacca ggcgtttccc     1740
cctggaagct ccctcgtgcg ctctcctgtt ccgaccctgc cgcttaccgg atacctgtcc     1800
gcctttctcc cttcgggaag cgtggcgctt tctcatagct cacgctgtag gtatctcagt     1860
tcggtgtagg tcgttcgctc caagctgggc tgtgtgcacg aaccccccgt tcagcccgac     1920
cgctgcgcct tatccggtaa ctatcgtctt gagtccaacc cggtaagaca cgacttatcg     1980
ccactggcag cagccactgg taacaggatt agcagagcga ggtatgtagg cggtgctaca     2040
gagttcttga agtggtggcc taactacggc tacactagaa ggacagtatt tggtatctgc     2100
gctctgctga agccagttac cttcggaaaa agagttggta gctcttgatc cggcaaacaa     2160
accaccgctg gtagcggtgg tttttttgtt tgcaagcagc agattacgcg cagaaaaaaa     2220
ggatctcaag aagatccttt gatcttttct acggggtctg acgctcagtg gaacgaaaac     2280
tcacgttaag ggattttggt catgagatta tcaaaaagga tcttcaccta gatccttta     2340 aattaaaaat gaagttttaa atcaatctaa agtatatatg agtaaacttg gtctgacagt     2400
taccaatgct taatcagtga ggcacctatc tcagcgatct gtctatttcg ttcatccata     2460
gttgcctgac tccccgtcgt gtagataact acgatacggg agggcttacc atctggcccc     2520
agtgctgcaa tgataccgcg agacccacgc tcaccggctc cagatttatc agcaataaac     2580
cagccagccg gaagggccga gcgcagaagt ggtcctgcaa ctttatccgc ctccatccag     2640
tctattaatt gttgccggga agctagagta gtagttcgc cagttaatag tttgcgcaac     2700
gttgttgcca ttgctacagg catcgtggtg tcacgctcgt cgtttggtat ggcttcattc     2760
agctccggtt cccaacgatc aaggcgagtt acatgatccc ccatgttgtg caaaaaagcg     2820
gttagctcct tcggtcctcc gatcgttgtc agaagtaagt tggccgcagt gttatcactc     2880
atggttatgg cagcactgca taattctctt actgtcatgc catccgtaag atgcttttct     2940
gtgactggtg agtactcaac caagtcattc tgagaatagt gtatgcggcg accgagttgc     3000
tcttgcccgg cgtcaatacg ggataatacc gcgccacata gcagaacttt aaaagtgctc     3060
atcattggaa aacgttcttc ggggcgaaaa ctctcaagga tcttaccgct gttgagatcc     3120
agttcgatgt aacccactcg tgcacccaac tgatcttcag catctttac tttcaccagc      3180 gtttctgggt gagcaaaaac aggaaggcaa atgccgcaa aaagggaat aagggcgaca       3240
```

```
cggaaatgtt gaatactcat actcttcctt tttcaatatt attgaagcat ttatcagggt    3300
tattgtctca tgagcggata catatttgaa tgtatttaga aaaataaaca aataggggtt    3360
ccgcgcacat ttccccgaaa agtgccacct ttccttcttc actgtccctt ctagaacgtt    3420
ctagaaggga cagtgaagaa ggaacacccg ctcgcgggtg ggcctactct aagaaaccat    3480
tattatcatg acattaacct ataaaaatag gcgtatcacg aggccctttc gtctcgcgcg    3540
tttcggtgat gacggtgaaa acctctgaca catgcagctc ccggagacgg tcacagcttg    3600
tctgtaagcg gatgccggga gcagacaagc ccgtcagggc gcgtcagcgg gtgttggcgg    3660
gtgtcggggc tggcttaact atgcggcatc agagcagatt gtactgagag tgcaccatat    3720
ggtcaggcgt ccttttgctt ggtgccgaag atcttgtcac cggcatcacc caggcctggc    3780
acgatgtagc cgtgctcgtt caggcgctgg tcgatcgagg cggtgtagat cttcacgtcc    3840
gggtgggctt tttccaccac ctcgatgcct tctggtgcgg cgaccagcac catggcgcga    3900
atctctttgc agccggcctt tttcagcagg tcgatggtgg caaccatcga gccgccggtg    3960
gccagcatcg ggtcgatgat cagggccagg cgctggttga tgtccggcgc gagcttttcc    4020
agataggtgt gggcttcgag ggtttcttcg tttcgggcaa cgccgacggc gctgaccttg    4080
gcccccggga tcaggctgag cacgccgtcg agcatgccga tgccggcgcg caggatcggt    4140
actacggtga tcttcttgcc ggcgattttt tcaaccgaga ccttgccaca ccagccgtcg    4200
atctcgtagg tttcgagggg caggtcctgg gtggcttcat acgtcaggag cgcgccgact    4260
tcctgggcga gttcgcgaaa attcttggtg ctgatatcgg cacggcgcat caggccaagc    4320
ttgtggcgga tcagcggatg gcggatctca cgagtgggca taggggaggg ctccgaaagg    4380
cgggcaaaaa aaccgcgcta gattaatcta ttcagcctgt gctgtcgtct ggtcattctg    4440
gacgttagtc cataaatgct tgatctgtga cgagcggatg cgtacctttg cccgcttttc    4500
caaaatgcta gccggctacg tatcgataag cttcacgctg ccgcaagcac tcagggcgca    4560
agggctgcta aaggaagcgg aacacgtaga aagccagtcc gcagaaacgg tgctgacccc    4620
ggatgaatgt cagctactgg gctatctgga caagggaaaa cgcaagcgca aagagaaagc    4680
aggtagcttg cagtgggctt acatggcgat agctagactg gcggttttta tggacagcaa    4740
gcgaaccgga attgccagct ggggcgccct ctggtaaggt tgggaagccc tgcaaagtaa    4800
actggatggc tttcttgccg ccaaggatct g                                    4831
```

<210> SEQ ID NO 14
<211> LENGTH: 6129
<212> TYPE: DNA
<213> ORGANISM: Artificial Sequence
<220> FEATURE:
<223> OTHER INFORMATION: Vector

<400> SEQUENCE: 14

```
atggcgcagg ggatcaagat ctgatcaaga gacaggatga ggatcgtttc gcatgattga      60
acaagatgga ttgcacgcag gttctccggc cgcttgggtg gagaggctat tcggctatga     120
ctgggcacaa cagacaatcg gctgctctga tgccgccgtg ttccggctgt cagcgcaggg     180
gcgcccggtt cttttttgtca agaccgacct gtccggtgcc ctgaatgaac tgcaggacga     240
ggcagcgcgg ctatcgtggc tggccacgac gggcgttcct tgcgcagctg tgctcgacgt     300
tgtcactgaa gcgggaaggg actggctgct attgggcgaa gtgccggggc aggatctcct     360
gtcatctcac cttgctcctg ccgagaaagt atccatcatg gctgatgcaa tgcggcggct     420
gcatacgctt gatccggcta cctgcccatt cgaccaccaa gcgaaacatc gcatcgagcg     480
```

```
agcacgtact cggatggaag ccggtcttgt cgatcaggat gatctggacg aagagcatca    540
ggggctcgcg ccagccgaac tgttcgccag gctcaaggcg cgcatgcccg acggcgagga    600
tctcgtcgtg acccatggcg atgcctgctt gccgaatatc atggtggaaa atggccgctt    660
ttctggattc atcgactgtg gccggctggg tgtggcggac cgctatcagg acatagcgtt    720
ggctacccgt gatattgctg aagagcttgg cggcgaatgg gctgaccgct tcctcgtgct    780
ttacggtatc gccgctcccg attcgcagcg catcgccttc tatcgccttc ttgacgagtt    840
cttctgagcg ggactctggg gttcgaaatg accgaccaag cgacgcccaa cctgccatca    900
cgagatttcg attccaccgc cgccttctat gaaaggttgg gcttcggaat cgttttccgg    960
gacgccggct ggatgatcct ccagcgcggg gatctcatgc tggagttctt cgcccacccc   1020
gggctcgatc ccctcgcgag ttggttcagc tgctgcctga ggctggacga cctcgcggag   1080
ttctaccggc agtgcaaatc cgtcggcatc caggaaacca gcagcggcta ccgcgcatc    1140 catgcccccg aactgcagga gtggggaggc acgatggccg cttcggtccc gggttcaag   1200 ctcagcggca gcggcaccca gggtgcggta atgccgttcg aactggtatg accccacgt    1260 atccaaggct tgaaagggga atatcgtgcc ggctactact acagtaatgc caaggcacaa   1320
gatgttctca aggacagcaa cggtcagccg ccgccctca gcggcgccgc ctaccgcagc    1380
agttcgagca agcacggctt gtggattggc gcccagcagc aggtcacctc gctggcgtcc   1440
gaccagtcgc gcggcttgag cgtgttcgcc aacgccacgg tgcatgacaa aaagaccaat   1500
gccatcgaca actatgtgca ggcaggactg gtattcaaag gccttcga tgcccgcgcc    1560 aaggacgaca tcggttcgc cctggcccgc gtgcacgtca accctgccta tcgcaagaac   1620
gcccgcctgg tcaaccaggc cgccggcctc tatgactacg acaacccggg cttcctgcca   1680
gtgcaggaca ccgagtacag cgccgagctg tattacggca ttcacttggc cgactggctc   1740
acggtacgcc caaccctgca gtacatccgc caccgggcg gggtgtcgca ggtcgatggc    1800
gccctgatcg gcggcctgaa gatccagagc agtttctaac ccgcgatcgc gccttgtgtc   1860
gcgtttcggt cgcgcagcgg ccccaacgat ctagaatgct ggatggattc tggggctgct   1920
gcgcagccca atcgcgacac aaggctgctc ccgaaccatt gaaacccatc cctccccgcc   1980
ccatctaagc accatagtca ttcacgcagg tgccccatga gcgaccagca ggatttcccc   2040
gaacaccctg acgaacacag cgaagtcgaa cacaccctcc aggccgaagt cagccacgcc   2100
ctcgccctgc ccggtcaaca gctgccggac aaggtctacg tcatcccgat ccacaaccgc   2160
ccgttcttcc cggccaggt actgccggtg atcgtcaatg aagagccctg gccgaaacg    2220 ctcgacctgg tagccaagtc accggaccac tgcctggcgc tgttcttcat ggacaccccg   2280
ccagaagacc accgccactt cgacacctcg gcactgccgc agtacggcac gctggtcaag   2340
gtgcaccatg ccagccgcga aaacggcaaa ttgcagttcg tcgcccaggg cctgtcccgg   2400
gtgcgcatcc gcaactggct caagcaccac cgcccgccct acctggtcga agtcgaatac   2460
ccgcgccagc ccgccgagcc gaccgacgag gtcaaagcct acggcattgc aggcatgcaa   2520
gcttggcgta atcatggtca tagctgtttc ctgtgtgaaa ttgttatccg ctcacaattc   2580
cacacaacat acgagccgga agcataaagt gtaaagcctg gggtgcctaa tgagtgagct   2640
aactcacatt aattgcgttg cgctcactgc ccgctttcca gtcgggaaac ctgtcgtgcc   2700
agctgcatta atgaatcggc caacgcgcgg ggagaggcgg tttgcgtatt gggcgctctt   2760
ccgcttcctc gctcactgac tcgctgcgct cggtcgttcg gctgcggcga gcggtatcag   2820
```

```
ctcactcaaa ggcggtaata cggttatcca cagaatcagg ggataacgca ggaaagaaca    2880
tgtgagcaaa aggccagcaa aaggccagga accgtaaaaa ggccgcgttg ctggcgtttt    2940
tccataggct ccgccccct gacgagcatc acaaaaatcg acgctcaagt cagaggtggc    3000
gaaacccgac aggactataa agataccagg cgtttccccc tggaagctcc ctcgtgcgct    3060
ctcctgttcc gaccctgccg cttaccggat acctgtccgc ctttctccct tcgggaagcg    3120
tggcgctttc tcatagctca cgctgtaggt atctcagttc ggtgtaggtc gttcgctcca    3180
agctgggctg tgtgcacgaa ccccccgttc agcccgaccg ctgcgcctta ccggtaact    3240 atcgtcttga gtccaacccg gtaagacacg acttatcgcc actggcagca gccactggta    3300
acaggattag cagagcgagg tatgtaggcg gtgctacaga gttcttgaag tggtggccta    3360
actacggcta cactagaagg acagtatttg gtatctgcgc tctgctgaag ccagttacct    3420
tcggaaaaag agttggtagc tcttgatccg gcaaacaaac caccgctggt agcggtggtt    3480
tttttgtttg caagcagcag attacgcgca gaaaaaaagg atctcaagaa gatcctttga    3540
tcttttctac ggggtctgac gctcagtgga acgaaaactc acgttaaggg attttggtca    3600
tgagattatc aaaaaggatc ttcacctaga tccttttaaa ttaaaaatga agttttaaat    3660
caatctaaag tatatatgag taaacttggt ctgacagtta ccaatgctta atcagtgagg    3720
cacctatctc agcgatctgt ctatttcgtt catccatagt tgcctgactc cccgtcgtgt    3780
agataactac gatacgggag ggcttaccat ctggccccag tgctgcaatg ataccgcgag    3840
acccacgctc accggctcca gatttatcag caataaacca gccagccgga agggccgagc    3900
gcagaagtgg tcctgcaact ttatccgcct ccatccagtc tattaattgt tgccgggaag    3960
ctagagtaag tagttcgcca gttaatagtt tgcgcaacgt tgttgccatt gctacaggca    4020
tcgtggtgtc acgctcgtcg tttggtatgg cttcattcag ctccggttcc caacgatcaa    4080
ggcgagttac atgatccccc atgttgtgca aaaaagcggt tagctccttc ggtcctccga    4140
tcgttgtcag aagtaagttg gccgcagtgt tatcactcat ggttatggca gcactgcata    4200
attctcttac tgtcatgcca tccgtaagat gcttttctgt gactggtgag tactcaacca    4260
agtcattctg agaatagtgt atgcggcgac cgagttgctc ttgcccggcg tcaatacggg    4320
ataataccgc gccacatagc agaactttaa aagtgctcat cattggaaaa cgttcttcgg    4380
ggcgaaaact ctcaaggatc ttaccgctgt tgagatccag ttcgatgtaa cccactcgtg    4440
cacccaactg atcttcagca tcttttactt tcaccagcgt ttctgggtga gcaaaaacag    4500
gaaggcaaaa tgccgcaaaa aagggaataa gggcgacacg gaaatgttga atactcatac    4560
tcttcctttt tcaatattat tgaagcattt atcagggtta ttgtctcatg agcggataca    4620
tatttgaatg tatttagaaa aataaacaaa taggggttcc gcgcacattt ccccgaaaag    4680
tgccaccttt ccttcttcac tgtcccttct agaacgttct agaagggaca gtgaagaagg    4740
aacacccgct cgcgggtggg cctactctaa gaaaccatta ttatcatgac attaacctat    4800
aaaaataggc gtatcacgag gccctttcgt ctcgcgcgtt tcggtgatga cggtgaaaac    4860
ctctgacaca tgcagctccc ggagacggtc acagcttgtc tgtaagcgga tgccgggagc    4920
agacaagccc gtcagggcgc gtcagcgggt gttggcgggt gtcggggctg gcttaactat    4980
gcggcatcag agcagattgt actgagagtg caccatatgg tcaggcgtcc ttttgcttgg    5040
tgccgaagat cttgtcaccg gcatcaccca ggcctggcac gatgtagccg tgctcgttca    5100
ggcgctggtc gatcgaggcg gtgtagatct tcacgtccgg gtgggctttt tccaccacct    5160
cgatgccttc tggtgcggcg accagcacca tggcgcgaat ctctttgcag ccggccttt    5220
```

```
tcagcaggtc gatggtggca accatcgagc cgccggtggc cagcatcggg tcgatgatca    5280
gggccaggcg ctggttgatg tccggcgcga gcttttccag ataggtgtgg gcttcgaggg    5340
tttcttcgtt tcgggcaacg ccgacggcgc tgaccttggc ccccgggatc aggctgagca    5400
cgccgtcgag catgccgatg ccggcgcgca ggatcggtac tacggtgatc ttcttgccgg    5460 cgatttttc aaccgagacc ttgccacacc agccgtcgat ctcgtaggtt tcgaggggca    5520
ggtcctgggt ggcttcatac gtcaggagcg ccgacttc ctgggcgagt tcgcgaaaat    5580
tcttggtgct gatatcggca cggcgcatca ggccaagctt gtggcggatc agcggatggc    5640
ggatctcacg agtgggcata ggggagggct ccgaaaggcg ggcaaaaaaa ccgcgctaga    5700
ttaatctatt cagcctgtgc tgtcgtctgg tcattctgga cgttagtcca taaatgcttg    5760
atctgtgacg agcggatgcg tacctttgcc cgcttttcca aaatgctagc cggctacgta    5820
tcgataagct tcacgctgcc gcaagcactc agggcgcaag ggctgctaaa ggaagcggaa    5880
cacgtagaaa gccagtccgc agaaacggtg ctgaccccgg atgaatgtca gctactgggc    5940
tatctggaca agggaaaacg caagcgcaaa gagaaagcag gtagcttgca gtgggcttac    6000
atggcgatag ctagactggg cggttttatg gacagcaagc gaaccggaat tgccagctgg    6060
ggcgccctct ggtaaggttg ggaagccctg caaagtaaac tggatggctt tcttgccgcc    6120
aaggatctg    6129

<210> SEQ ID NO 15
<211> LENGTH: 1316
<212> TYPE: DNA
<213> ORGANISM: Artificial Sequence
<220> FEATURE:
<223> OTHER INFORMATION: k/o sequence

<400> SEQUENCE: 15
ggtttcaagc tcagcggcag cggcacccag ggtgcggtaa tgccgttcga actggtatgg      60
accccacgta tccaaggctt gaaagggaa tatcgtgccg gctactacta cagtaatgcc     120
aaggcacaag atgttctcaa ggacagcaac ggtcagccgg ccgccctcag cggcgccgcc     180
taccgcagca gttcgagcaa gcacggcttg tggattggcg cccagcagca ggtcacctcg     240
ctggcgtccg accagtcgcg cggcttgagc gtgttcgcca acgccacggt gcatgacaaa     300
aagaccaatg ccatcgacaa ctatgtgcag gcaggactgg tattcaaagg cctttcgat    360 gcccgcgcca aggacgacat cggtttcgcc ctggcccgcg tgcacgtcaa ccctgcctat     420
cgcaagaacg cccgcctggt caaccaggcc gccggcctct atgactacga caacccgggc     480
ttcctgccag tgcaggacac cgagtacagc gccgagctgt attacggcat tcacttggcc     540
gactggctca cggtacgccc caacctgcag tacatccgcc accgggcgg ggtgtcgcag     600 gtcgatggcg ccctgatcgg cggcctgaag atccagagca gtttctaacc cgcgatcgcg     660
ccttgtgtcg cgtttcggtc gcgcagcggc cccaacgatc tagaatgctg gatgattct    720 ggggctgctg cgcagcccaa tcgcgacaca aggctgctcc gaaccattg aaacccatcc     780 ctccccgccc catctaagca ccatagtcat tcacgcaggt gccccatgag cgaccagcag     840
gatttccccg aacaccctga cgaacacagc gaagtcgaac acaccctcca ggccgaagtc     900
agccacgccc tcgccctgcc cggtcaacag ctgccggaca aggtctacgt catcccgatc     960
cacaaccgcc cgttcttccc ggcccaggta ctgccggtga tcgtcaatga agagccctg    1020 gccgaaacgc tcgacctggt agccaagtca ccggaccact gcctggcgct gttcttcatg    1080
```

| | |
|---|---|
| gacaccccgc cagaagacca ccgccacttc gacacctcgg cactgccgca gtacggcacg | 1140 |
| ctggtcaagg tgcaccatgc cagccgcgaa acggcaaat tgcagttcgt cgcccagggc | 1200 |
| ctgtcccggg tgcgcatccg caactggctc aagcaccacc gcccgcccta cctggtcgaa | 1260 |
| gtcgaatacc cgcgccagcc cgccgagccg accgacgagg tcaaagccta cggcat | 1316 |

<210> SEQ ID NO 16
<211> LENGTH: 4787
<212> TYPE: DNA
<213> ORGANISM: Artificial Sequence
<220> FEATURE:
<223> OTHER INFORMATION: result of gene knock-out

<400> SEQUENCE: 16

| | |
|---|---|
| atgacccagc cgccgctgcg cctgcgcaat tccgccaggg acggctggct gatgctcgaa | 60 |
| tgggcggacg gcgcggtcag ccggatcgac catgcgcgcc tgcgcgccgc ctgtccctgt | 120 |
| gcgcaatgcc gggcgcagcg cctgcgcgga cggatcgtcg cggcggagca gggcgtgcgc | 180 |
| ctgcgcgata tccgcctgca gggctacggc gtgcagttgc tgttcgacga tggtcacgag | 240 |
| cgcggtatct accctggtc ctatctgcgc gacgaactct gaggcgggta ttgttccgct | 300 |
| cccggcaaca acgtgaagcg tgttcatggg tttcagattg ttgccaatcc ctgcgttgtc | 360 |
| cccgtcccgc cacggccacc acccgggtga cccgctcgga ggcccgccgc ctggcttcgt | 420 |
| tgtcgtttcc gtaacactgt tttccagcct gaaacgtttc agctttactt gcaaagacct | 480 |
| tatcattcgc aaattaacca ttgttctgct tggctcagat catgagtcct cttcataaac | 540 |
| ccttgctcct tgcaaggtta tcgaggaagt agagcggtcg ctgcgtgcgg ccagtcgacc | 600 |
| attcgcaacg aggaagcgtt cgcgtgaaat cccatcttct ccgcccggcc ctgcgccccg | 660 |
| tggccggcgg cctattgtcc gcctcccgc tgtgcaacgc ggtgcacgcc gccgaggcgt | 720 |
| tctcgccgaa ctcgaaatgg atgctcggcg actgggcgg caagcgcacc gagctgctgg | 780 |
| agaagggcta cgacttcaag ctggagtacg tcggcgaggg ggcggccaac ctcgatggcg | 840 |
| gctatgacga cgacaagacc ggacgctaca ccgaccagtt cgccctgggc gtgcacatgg | 900 |
| acctggagaa gatcctcggc tggaaggcta ccgagttcca gttcaccgtc accgagcgca | 960 |
| acggcaagaa ccttttccaa cgaccgcatcg gcgacccgcg tgccgggcac atcagctcgg | 1020 |
| tgcaggaggt ctggggccgc gggcagacct ggcggctgac ccagctgtgg ctcaagcagc | 1080 |
| agtacttcgc cggcgcgctg acgtgaaat tcggccgttt cggcgagggc gaggacttca | 1140 |
| acagcttccc ctgcgatttc cagaacctgg ccttctgcgg ctcgcaggtg ggcaactggg | 1200 |
| cggggagcat ctggtacaac tggccggtca gccagtgggc gttgcgggtg aagtacaact | 1260 |
| tcgcgccgga ctggtacgtg caggtcggcg cctacgagca gaacccgtcg aacctggaga | 1320 |
| ccggcaacgg cttcaagatg agcggcagcg ggaccaaggg cgcgctgctg ccggtggagc | 1380 |
| tgatctggca gccgaaggtc ggcgccgagc aactgccggg cgagtaccgg ctgggttact | 1440 |
| actacagcac ggcgaaggcc gatgacgtct acgacgacgt cgacgccag ccgcagggcc | 1500 |
| tgaccggcaa cgacttcaag tcgcgcggca gcaagcatgg ctggtgggtg gtggcgcagc | 1560 |
| agcaggtcac ttcgcacaac ggcgatgcct cgcgcgggtt gagcctgttc gccaacctga | 1620 |
| cggtccacga caaggcgacc aacgtggtgg acaactacca gcagctcggg gtggtctaca | 1680 |
| aggggccgtt cgacgcgcgg ccgaaggacg acatcggcct gggtatcgcg cgcatccatg | 1740 |
| tcaacgacga tgtgaagaag cgccagcgcc tggtgaacca ggtgaacggc atcgacgact | 1800 |
| acgacaaccc gctgtaccag ccgctgcagg acaccgagta caacgccgag ctgtactacg | 1860 |

| | |
|---|---|
| gggtgcatgt gaccgactgg ctgacggtgc ggccgaacct gcaatacatc aagcagccgg | 1920 |
| gcggggtcga cgaggtcgac aacgcgctgg tggcggggat caagatccag acggtgttct | 1980 |
| aggctgttgc ttcggacaac cgcgattcgg tcatggccag cggccatttc ttcagcgccg | 2040 |
| cccaacgcgg cgcggcgggc tgaacagccc ggcgtgcaga acgtaatagg agagtaagca | 2100 |
| atgcctgtca tcaaccccgc ccaccgggag cccacagccg gctcccggcc ttccgggcct | 2160 |
| cggcccggaa ggggctttgc caaggggagg cgcgttcccg cccttggcaa agccccttcg | 2220 |
| ataccttgcg acccgcggaa ccctgcatgc cgtcccgacc ccgacccagc ttcgtctccc | 2280 |
| acctgttgcc cggctccctg gcgctctgcg gcctggccat cgcctgcgcc gtccagggcg | 2340 |
| aggagcgacg cagcctcgaa cccatggtgg tgaccggcag ctacaacccc agcgacacct | 2400 |
| tcgacctgcc gttctcggtg gatagcatcg agcgtcggca gatcgccgac ggccagctcg | 2460 |
| gcatcaacct ctccgaagtc ctgccgcggg tacctggcct ggtggtgcag aaccgccaga | 2520 |
| actacgccca ggacctgcaa atctcctcgc gcggctacgg cgcccgctcg gccttcggta | 2580 |
| tccgcgggct gaagctgctc gccgacggca tcccggccag tacgccggat ggccagggcc | 2640 |
| aggccgcgac cctcaacctc gacgtcgccg agcgcatcga ggtactgcgc gggccggcct | 2700 |
| cgacgatcta cggcagcaac gccggcgggg tgatccagat gttctcccgc gacggccagg | 2760 |
| gcgcccgcg gtcggcgcg gaagccaccg tcggcagcga tggcctgagc cgcaaccacc | 2820 |
| tgtacacgga aggcgagggc gacggggtcg gtttcctggt ggatgcctcg cggatggaca | 2880 |
| ccgacggcta ccgcgaccac agcgccgcgc gccgcgacca gaccttcgcc aagctcaact | 2940 |
| tcaggcccga cgccgacagc cgcctggcgc tgatctacag cagcctggaa cagaacgaca | 3000 |
| ttgaagatcc gctggggcag acctgggacg cctacaagta cgaccgcgc tccgtcaccg | 3060 |
| ccaacgccga gctgtacgac acgcgcaaga gcatcgacca ccagcaggcc gggatgaact | 3120 |
| acgagcgcta cttcggcgag gcgaccttgc aggtcaacgc ctacgtgggc aagcgcagtg | 3180 |
| tcgtgcagta tcaggcgata cccaagcaga taggatgcga gagtaatccg cgttgccaga | 3240 |
| gaaacggcgc ggtgatcgac ttcgaccgcg acttccacgg tggcaccgtg cgctggctgc | 3300 |
| aaccggtaag ccaggcgccg ggcgagctga acctgaccgt cggcctcgac tacgaccaga | 3360 |
| gccgcgacga ccgtcgcggc taccagaact tcaacggcga ccagctcggc gtgaagggca | 3420 |
| agttgcgccg cgacgaggtg gacaccgcca ccagcctcga tccctacctg caggcgagct | 3480 |
| gggccatcga cgcctggacc ctgcaggccg gggtgcgcca cagcaccatg aagatggagg | 3540 |
| tcgacgaccg ctacctgagc aacggcgatg ccagcggctc gcggcgctac cggaagaaca | 3600 |
| ccccgtcgtt ctcggtgatg tacgccttca cccccgacct gcacggctac ctcagcgccg | 3660 |
| gcaagggctt cgagactccg acccaggcgg agatggccta tgcgccggtg gcggcgaacg | 3720 |
| cgccggacgt cttcaacttc ggcctcaagc cagccaccag cagccagtac gaagccgggc | 3780 |
| tgaaggcgcg cctgtgggc aatacgcggg tcaacgcggc gatcttccag gtccgcaccg | 3840 |
| aggacgagat cgtcgtcgcc agctccctcg gcggtcgcac cagctaccag aacgccggca | 3900 |
| agaccctgcg tcgcggcttc gaactgggcc tggagagcga actgagcgag cactggaacg | 3960 |
| ccaacctggc ctatacccgg ctatccgcca cctacgattc ggatttcgag gccggcggca | 4020 |
| agaccatcgg caagggcaag cacctgccgg gcgtgccgga aagcagcctg ttcggcgaac | 4080 |
| tggtgtggaa gcccgcggag ggcatcagca tgggctggga aggcatgtac cgcagccagg | 4140 |
| tctacgtcga ggacagcaac agcgaaaagg ccgcgccgag ctatgcggta ttcaactggc | 4200 |

```
gcacccgctt cgaacagcgc ctgggggcct ggaccttcca ccagctggtg cgcctggaca    4260
acctgttcga ccgccagtac gtcggctcgg tcatcgtcgg cgacggcaac cggcgttact    4320
acgaagcggc ccccgggctg tcctggtacg cgggagccgg ggtcgaatac cagttctgaa    4380
gtgccggatg cgcttgttcg cgctacccgg ccagcccttg tcagcgtcgt caattccgat    4440
tactgtatga atgtacagta atcggaaatc gcctgcctgc gcgacaagga gcaccgatca    4500
tgagccacaa ccttgccgaa ctgccgctgt cccgacgcca cgcccggagc gcgagaaac    4560 aggcctgcct gcgcctccac ctgtcccgca atcgtgccag cgaacgcctg gagcgcgccg    4620
tgcgcgacga gtcgagcgc ctgctggggg ctcgcgagcg ccagggaacc ggctggccgg    4680
agtgggtcag cgcggagctc tgcgtggcgg acgacccgct cttcgtgcgc aaggtggtgg    4740
cgcgcctgaa agccgcggtg gactggcaac gccagcgcgc agcctga                  4787

<210> SEQ ID NO 17
<211> LENGTH: 2274
<212> TYPE: DNA
<213> ORGANISM: Pseudomonas aeruginosa

<400> SEQUENCE: 17
ggcccaggag gggggatctg gcattttggg gaggtgtgaa atgcggcgcg aaagtctgtt      60
ggtatcggtt tgcaagggcc tgcgggtaca tgtcgagcgc gttgggcagg atcccgggcg     120
cagcacggtg atgctggtca acggcgcgat ggcgaccacc gcctcgttcg cccggacctg     180
caagtgcctg gccgaacatt tcaacgtggt gctgttcgac ctgcccttcg ccgggcagtc     240
gcgtcagcac aacccgcagc gggggttgat caccaaggac gacgaggtgg aaatcctcct     300
ggcgctgatc gagcgcttcg aggtcaatca cctggtctcc gcgtcctggg gcggtatctc     360
cacgctgctg gcgctgtcgc gcaatccgcg cggcatccgc agctcggtgg tgatggcatt     420
cgcccctgga ctgaaccagg cgatgctcga ctacgtcggg cgggcgcagg cgctgatcga     480
gctggacgac aagtcggcga tcggccatct gctcaacgag accgtcggca aatacctgcc     540
gccgcgcctg aaagccagca accatcagca catggcttcg ctggccaccg gcgaatacga     600
gcaggcgcgc tttcacatcg accaggtgct ggcgctcaac gatcgggct acctggcttg     660 cctggagcgg atccagagcc acgtgcattt catcaacggc agctgggacg aatacaccac     720
cgccgaggac gcccgccagt tccgcgacta cctgccgcac tgcagtttct cgcgggtgga     780
gggcaccggg catttcctcg acctggagtc caagctggcc gcggtacgcg tgcaccgcgc     840
cctgctcgag cacctgctga gcaaccgga gccgcagcgg gcggaacgcg cggcgggatt     900
ccacgagatg gccatcggct acgcctgaac ccttgacctg cgaagacccg gcctggccgg     960
gctttgcggt tgcataacgc acggagtagc accatgcacg ccatcctcat cgccatcggc    1020
tcggccggcg acgtatttcc cttcatcggc ctggcccgga ccctgaaatt gcgcgggcac    1080
cgcgtgagcc tctgcaccat cccggtgttt cgcgacgcgg tggagcagca cggcatcgcg    1140
ttcgtcccgc tgagcgacga actgacctac cgccggacca tgggcgatcc cgcgcctgtgg   1200 gaccccaaga cgtccttcgg cgtgctctgg caaaccatcg ccgggatgat cgagccggtc    1260
tacgagtacg tctcggcgca gcgccatgac gacatcgtgg tggtcggctc gctctgggcg    1320
ctgggcgcac gcatcgctca cgagaagtac gggattccct acctgtccgc gcaggtctcg    1380
ccatcgacct tgttgtcggc gcacctgccg ccggtacacc ccaagttcaa cgtgcccgag    1440
cagatgccgc tggcgatgcg caagctgctc tggcgctgca tcgagcgctt caagctggat    1500
cgcacctgcg cgccggatat caacgcggtg cggcgcaagg tcggcctgga gacgccggtg    1560
```

```
aagcgcatct tcacccaatg gatgcattcg ccgcagggcg tggtctgcct gttcccggcc    1620
tggttcgcgc cgccccagca ggattggccg caacccctgc acatgaccgg cttcccgctg    1680
ttcgacggca gtatcccggg gaccccgctc gacgacgaac tgcaacgctt tctcgatcag    1740
ggcagccggc cgctggtgtt cacccagggc tcgaccgaac acctgcaggg cgacttctac    1800
gccatggccc tgcgcgcgct ggaacgcctc ggcgcgcgtg gatcttcct caccggcgcc     1860 ggccaggaac cgctgcgcgg cttgccgaac cacgtgctgc agcgcgccta cgcgccactg    1920
ggagccttgc tgccatcgtg cgccgggctg gtccatccgg gcggtatcgg cgccatgagc    1980
ctggccttgg cggcggggt gccgcaggtg ctgctgccct cgcccacga ccagttcgac      2040 aatgccgaac ggctggtccg gctcggctgc gggatgcgcc tgggcgtgcc attgcgcgag    2100
caggagttgc gcggggcgct gtggcgcttg ctcgaggacc cggccatggc ggcggcctgt    2160
cggcgtttca tggaattgtc acaaccgcac agtatcgctt gcggtaaagc ggcccaggtg    2220
gtcgaacgtt gtcataggga gggggatgcg cgatggctga aggctgcgtc ctga          2274

<210> SEQ ID NO 18
<211> LENGTH: 16359
<212> TYPE: DNA
<213> ORGANISM: Artificial Sequence
<220> FEATURE:
<223> OTHER INFORMATION: vector

<400> SEQUENCE: 18
cacaaaattc ctgcaggggc cggcccagcg ccggcggtcg agtggcgacg gcgcggcttg      60
tccgcgccct ggtagattgc ctggccgtag gccagccatt tttgagcggc cagcggccgc     120
gataggccga cgcgaagcgg cggggcgtag ggagcgcagc gaccgaaggg taggcgcttt     180
ttgcagctct tcggctgtgc gctggccaga cagttatgca caggccaggc gggttttaag    240
agttttaata gttttaaag agttttaggc ggaaaaatcg cctttttct cttttatatc      300 agtcacttac atgtgtgacc ggttcccaat gtacggcttt gggttcccaa tgtacgggtt    360
ccggttccca atgtacggct ttgggttccc aatgtacgtg ctatccacag gaaagagacc    420
ttttcgacct ttttcccctg ctagggcaat ttgccctagc atctgctccg tacattagga    480
accggcggat gcttcgccct cgatcaggtt gcggtagcgc atgactagga tcggccagc    540 ctgccccgcc tcctccttca atcgtactc cggcaggtca tttgacccga tcagcttgcg    600
cacggtgaaa cagaacttct tgaactctcc ggcgctgcca ctgcgttcgt agatcgtctt    660
gaacaaccat ctggcttctg ccttgcctgc ggcgcggcgt gccaggcggt agagaaaacg    720
gccgatgccg ggatcgatca aaagtaatc ggggtgaacc gtcagcacgt ccgggttctt    780
gccttctgtg atctcgcggt acatccaatc aactagctcg atctcgatgt actccggccg    840
cccggtttcg ctctttacga tcttgtagcg gctaatcaag gcttcaccct cggataccgt    900
caccaggcgg ccgttcttgg ccttcttcgt acgctgcatg gcaacgtgcg tggtgtttaa    960
ccgaatgcag gtttctacca ggtcgtcttt ctgctttccg ccatcggctc gccggcagaa    1020
cttgagtacg tccgcaacgt gtggacggaa cacgcggccg ggcttgtctc ccttcccttc    1080
ccggtatcgg ttcatggatt cggttagatg gaaaccgcc atcagtacca ggtcgtaatc     1140
ccacacactg gccatgccgg ccggccctgc ggaaacctct acgtgcccgt ctggaagctc    1200
gtagcggatc acctcgccag ctcgtcggtc acgcttcgac agacggaaaa cggccacgtc    1260
catgatgctg cgactatcgc gggtgcccac gtcatagagc atcggaacga aaaaatctgg    1320
```

```
ttgctcgtcg cccttgggcg gcttcctaat cgacggcgca ccggctgccg gcggttgccg    1380
ggattctttg cggattcgat cagcggccgc ttgccacgat tcaccggggc gtgcttctgc    1440
ctcgatgcgt tgccgctggg cggcctgcgc ggccttcaac ttctccacca ggtcatcacc    1500
cagcgccgcg ccgatttgta ccgggccgga tggtttgcga ccgctcacgc cgattcctcg    1560
ggcttggggg ttccagtgcc attgcagggc cggcagacaa cccagccgct tacgcctggc    1620
caaccgcccg ttcctccaca catggggcat tccacggcgt cggtgcctgg ttgttcttga    1680
ttttccatgc cgcctccttt agccgctaaa attcatctac tcatttattc atttgctcat    1740
ttactctggt agctgcgcga tgtattcaga tagcagctcg gtaatggtct tgccttggcg    1800
taccgcgtac atcttcagct tggtgtgatc ctccgccggc aactgaaagt tgacccgctt    1860
catggctggc gtgtctgcca ggctggccaa cgttgcagcc ttgctgctgc gtgcgctcgg    1920
acggccggca cttagcgtgt ttgtgctttt gctcattttc tctttacctc attaactcaa    1980
atgagttttg atttaatttc agcggccagc gcctggacct cgcgggcagc gtcgccctcg    2040
ggttctgatt caagaacggt tgtgccggcg gcggcagtgc ctgggtagct cacgcgctgc    2100
gtgatacggg actcaagaat gggcagctcg tacccggcca gcgcctcggc aacctcaccg    2160
ccgatgcgcg tgcctttgat cgcccgcgac acgacaaagg ccgcttgtag ccttccatcc    2220
gtgacctcaa tgcgctgctt aaccagctcc accaggtcgg cggtggccca tatgtcgtaa    2280
gggcttggct gcaccggaat cagcacgaag tcggctgcct tgatcgcgga cacagccaag    2340
tccgccgcct ggggcgctcc gtcgatcact acgaagtcgc gccggccgat ggccttcacg    2400
tcgcggtcaa tcgtcgggcg gtcgatgccg acaacggtta gcggttgatc ttcccgcacg    2460
gccgcccaat cgcgggcact gccctgggga tcggaatcga ctaacagaac atcggccccg    2520
gcgagttgca gggcgcgggc tagatgggtt gcgatggtcg tcttgcctga cccgcctttc    2580
tggttaagta cagcgataac cttcatgcgt tccccttgcg tatttgttta tttactcatc    2640
gcatcatata cgcagcgacc gcatgacgca agctgtttta ctcaaataca catcacctttt   2700
ttagacggcg gcgctcggtt tcttcagcgg ccaagctggc cggccaggcc gccagcttgg    2760
catcagacaa accggccagg atttcatgca gccgcacggt tccggatgag cattcatcag    2820
gcgggcaaga atgtgaataa aggccggata aaacttgtgc ttatttttct ttacggtctt    2880
taaaaaggcc gtaatatcca gctgaacggt ctggttatag gtacattgag caactgactg    2940
aaatgcctca aaatgttctt tacgatgcca ttgggatata tcaacggtgg tatatccagt    3000
gatttttttc tccattttag cttccttagc tcctgaaaat ctcgataact caaaaaatac    3060
gcccggtagt gatcttattt cattatggtg aaagttggaa cctcttacgt gccgatcaac    3120
gtctcatttt cgccaaaagt tggcccaggg cttcccggta tcaacaggga caccaggatt    3180
tatttattct gcgaagtgat cttccgtcac aggtatttat tcggcgcaaa gtgcgtcggg    3240
tgatgctgcc aacttactga tttagtgtat gatggtgttt ttgaggtgct ccagtggctt    3300
ctgtttctat cagctgtccc tcctgttcag ctactgacgg ggtggtgcgt aacggcaaaa    3360
gcaccgccgg acatcagcgc tagcggagtg tatactggct tactatgttg gcactgatga    3420
gggtgtcagt gaagtgcttc atgtggcagg agaaaaaagg ctgcaccggt gcgtcagcag    3480
aatatgtgat acaggatata ttccgcttcc tcgctcactg actcgctacg ctcggtcgtt    3540
cgactgcggc gagcggaaat ggcttacgaa cggggcggag atttcctgga agatgccagg    3600
aagatactta acagggaagt gagagggccg cggcaaagcc gttttccat aggctccgcc    3660
cccctgacaa gcatcacgaa atctgacgct caaatcagtg gtggcgaaac ccgacaggac    3720
```

```
tataaagata ccaggcgttt ccccctggcg gctccctcgt gcgctctcct gttcctgcct    3780
ttcggtttac cggtgtcatt ccgctgttat ggccgcgttt gtctcattcc acgcctgaca    3840
ctcagttccg ggtaggcagt tcgctccaag ctggactgta tgcacgaacc ccccgttcag    3900
tccgaccgct gcgccttatc cggtaactat cgtcttgagt ccaacccgga agacatgca     3960
aaagcaccac tggcagcagc cactggtaat tgatttagag gagttagtct tgaagtcatg    4020
cgccggttaa ggctaaactg aaaggacaag ttttggtgac tgcgctcctc caagccagtt    4080
acctcggttc aaagagttgg tagctcagag aaccttcgaa aaaccgccct gcaaggcggt    4140
tttttcgttt tcagagcaag agattacgcg cagaccaaaa cgatctcaag aagatcatct    4200
tattaatcag ataaaatatt tctagatttc agtgcaattt atctcttcaa atgtagcacc    4260
tgaagtcagc cccatacgat ataagttgta attctcatgt ttgacagctt atcatcgata    4320
agctttaatg cggtagttta tcacagttaa attgctaacg cagtcaggca ccgtgtatga    4380
aatctaacaa tgcgctcatc gtcatcctcg gcaccgtcac cctggatgct gtaggcatag    4440
gcttggttat gccggtactg ccgggcctct tgcgggatat cgtccattcc gacagcatcg    4500
ccagtcacta tggcgtgctg ctagcgctat atgcgttgat gcaatttcta tgcgcacccg    4560
ttctcggagc actgtccgac cgctttggcc gccgcccagt cctgctcgct tcgctacttg    4620
gagccactat cgactacgcg atcatggcga ccacacccgt cctgtggatc ctctacgccg    4680
gacgcatcgt ggccggcatc accggcgcca caggtgcggt tgctggcgcc tatatcgccg    4740
acatcaccga tggggaagat cgggctcgcc acttcgggct catgagcgct tgtttcggcg    4800
tgggtatggt ggcaggcccc gtggccgggg gactgttggg cgccatctcc ttgcatgcac    4860
cattccttgc ggcggcggtg ctcaacggcc tcaacctact actgggctgc ttcctaatgc    4920
aggagtcgca taagggagag cgtcgaccga tgcccttgag agccttcaac ccagtcagct    4980
ccttccggtg ggcgcggggc atgactatcg tcgccgcact tatgactgtc ttctttatca    5040
tgcaactcgt aggacaggtg ccggcagcgc tctgggtcat tttcggcgag gaccgctttc    5100
gctggagcgc gacgatgatc ggcctgtcgc ttgcggtatt cggaatcttg cacgccctcg    5160
ctcaagcctt cgtcactggt cccgccacca acgtttcgg cgagaagcag gccattatcg    5220
ccggcatggc ggccgacgcg ctgggctacg tcttgctggc gttcgcgacg cgaggctgga    5280
tggccttccc cattatgatt cttctcgctt ccggcggcat cgggatgccc gcgttgcagg    5340
ccatgctgtc caggcaggta gatgacgacc atcagggaca gcttcaagga tcgctcgcgg    5400
ctcttaccag cctaacttcg atcactggac cgctgatcgt cacggcgatt tatgccgcct    5460
cggcgagcac atggaacggg ttggcatgga ttgtaggcgc cgccctatac cttgtctgcc    5520
tccccgcgtt gcgtcgcggt gcatggagcc gggccacctc gacctgaatg gaagccggcg    5580
gcacctcgct aacggattca ccactccaag aattggagcc aatcaattct tgcggagaac    5640
tgtgaatgcg caaaccaacc cttggcagaa catatccatc gcgtccgcca tctccagcag    5700
ccgcacgcgg cgcatctcgg gcagcgttgg gtcctggcca cgggtgcgca tgatcgtgct    5760
cctgtcgttg aggacccggc taggctggcg gggttgcctt actggttagc agaatgaatc    5820
accgatacgc gagcgaacgt gaagcgactg ctgctgcaaa acgtctgcga cctgagcaac    5880
aacatgaatg gtcttcggtt tccgtgtttc gtaaagtctg gaaacgcgga agtcccctac    5940
gtgctgctga gttgcccgc aacagagagt ggaaccaacc ggtgatacca cgatactatg    6000
actgagagtc aacgccatga gcggcctcat ttcttattct gagttacaac agtccgcacc    6060
```

```
gctgtccggt agctccttcc ggtgggcgcg gggcatgact atcgtcgccg cacttatgac    6120
tgtcttcttt atcatgcaac tcgtaggaca ggtgccggca gcgcccaaca gtccccggc     6180
cacgggcct gccaccatac ccacgccgaa acaagcgccc tgcaccatta tgttccggat     6240
ctgcatcgca ggatgctgct ggctaccctg tggaacacct acatctgtat taacgaagcg    6300
ctaaccgttt ttatcaggct ctgggaggca gaataaatga tcatatcgtc aattattacc    6360
tccacgggga gagcctgagc aaactggcct caggcatttg agaagcacac ggtcacactg    6420
cttccggtag tcaataaacc ggtaaaccag caatagacat aagcggctat ttaacgaccc    6480
tgccctgaac cgacgaccgg gtcgaatttg cttttcgaatt tctgccattc atccgcttat   6540
tatcacttat tcaggcgtag caccaggcgt ttaagggcac caataactgc cttaaaaaaa    6600
ttacgccccg ccctgccact catcgcagta ctgttgtaat tcattaagca ttctgccgac    6660
atggaagcca tcacaaacgg catgatgaac ctgaatcgcc agcggcatca gcaccttgtc    6720
gccttgcgta taatatttgc ccatggattt aaatttaatc tttctgcgaa ttgagatgac    6780
gccactggct gggcgtcatc ccggtttccc gggtaaacac caccgaaaaa tagttactat    6840
cttcaaagcc acattcggtc gaaatatcac tgattaacag gcggctatgc tggagaagat    6900
attgcgcatg acacactctg acctgtcgca gatattgatt gatggtcatt ccagtctgct    6960
ggcgaaattg ctgacgcaaa acgcgctcac tgcacgatgc ctcatcacaa aatttatcca    7020
gcgcaaaggg acttttcagg ctagccgcca gccgggtaat cagcttatcc agcaacgttt    7080
cgctggatgt tggcggcaac gaatcactgg tgtaacgatg gcgattcagc aacatcacca    7140
actgcccgaa cagcaactca gccatttcgt tagcaaacgg cacatgctga ctactttcat    7200
gctcaagctg accgataacc tgccgcgcct gcgccatccc catgctacct aagcgccagt    7260
gtggttgccc tgcgctggcg ttaaatcccg gaatcgcccc ctgccagtca agattcagct    7320
tcagacgctc cggcaataa ataatattct gcaaaaccag atcgttaacg aagcgtagg     7380
agtgtttatc gtcagcatga atgtaaaaga gatcgccacg ggtaatgcga taagggcgat    7440
cgttgagtac atgcaggcca ttaccgcgcc agacaatcac cagctcacaa aaatcatgtg    7500
tatgttcagc aaagacatct tgcggataac ggtcagccac agcgactgcc tgctggtcgc    7560
tggcaaaaaa atcatctttg agaagttttta actgatgcgc caccgtggct acctcggcca    7620
gagaacgaag ttgattattc gcaatatggc gtacaaatac gttgagaaga ttcgcgttat    7680
tgcagaaagc catcccgtcc ctggcgaata tcacgcggtg accagttaaa ctctcggcga    7740
aaaagcgtcg aaaagtggtt actgtcgctg aatccacagc gataggcgat gtcagtaacg    7800
ctggcctcgc tgtggcgtag cagatgtcgg gctttcatca gtcgcaggcg gttcaggtat    7860
cgctgaggcg tcagtcccgt ttgctgctta agctgccgat gtagcgtacg cagtgaaaga    7920
gaaaattgat ccgccacggc atcccaattc acctcatcgg caaaatggtc ctccagccag    7980
gccagaagca agttgagacg tgatgcgctg ttttccaggt tctcctgcaa actgcttta     8040
cgcagcaaga gcagtaattg cataaacaag atctcgcgac tggcggtcga gggtaaatca    8100
ttttcccctt cctgctgttc catctgtgca accagctgtc gcacctgctg caatacgctg    8160
tggttaacgc gccagtgaga cggatactgc ccatccagct cttgtggcag caactgattc    8220
agcccggcga gaaactgaaa tcgatccggc gagcgataca gcacattggt cagacacaga    8280
ttatcggtat gttcatacag atgccgatca tgatcgcgta cgaaacagac cgtgccaccg    8340
gtgatggtat agggctgccc attaaacaca tgaatacccg tgccatgttc gacaatcaca    8400
atttcatgaa aatcatgatg atgttcagga aaatccgcct gcgggagccg gggttctatc    8460
```

```
gccacggacg cgttaccaga cggaaaaaaa tccacactat gtaatacggt catactggcc    8520
tcctgatgtc gtcaacacgg cgaaatagta atcacgaggt caggttctta ccttaaattt    8580
tcgacggaaa accacgtaaa aaacgtcgat ttttcaagat acagcgtgaa ttttcaggaa    8640
atgcggtgag catcacatca ccacaattca gcaaattgtg aacatcatca cgttcatctt    8700
tccctggttg ccaatggccc attttcctgt cagtaacgag aaggtcgcga attcaggcgc    8760
tttttagact ggtcgtaatg aacatttaaa tgaattccct tgggactcta gagatccgcg    8820
ggggcccagg agggggatc tggcatttttt gggaggtgtg aaatgcggcg cgaaagtctg    8880
ttggtatcgg tttgcaaggg cctgcgggta catgtcgagc gcgttgggca ggatcccggg    8940
cgcagcacgg tgatgctggt caacggcgcg atggcgacca ccgcctcgtt cgcccggacc    9000
tgcaagtgcc tggccgaaca tttcaacgtg gtgctgttcg acctgccctt cgccgggcag    9060
tcgcgtcagc acaacccgca gcggggttg atcaccaagg acgacgaggt ggaaatcctc    9120
ctggcgctga tcgagcgctt cgaggtcaat cacctggtct ccgcgtcctg gggcggtatc    9180
tccacgctgc tggcgctgtc gcgcaatccg cgcggcatcc gcagctcggt ggtgatggca    9240
ttcgcccctg gactgaacca ggcgatgctc gactacgtcg ggcgggcgca ggcgctgatc    9300
gagctggacg acaagtcggc gatcggccat ctgctcaacg agaccgtcgg caaatacctg    9360
ccgccgcgcg tgaaagccag caaccatcag cacatggctt cgctggccac cggcgaatac    9420
gagcaggcgc gctttcacat cgaccaggtg ctggcgctca cgatcggggg ctacctggct    9480
tgcctggagc ggatccagag ccacgtgcat ttcatcaacg gcagctggga cgaatacacc    9540
accgccgagg acgcccgcca gttccgcgac tacctgccgc actgcagttt ctcgcgggtg    9600
gagggcaccg ggcatttcct cgacctggag tccaagctgg ccgcggtacg cgtgcaccgc    9660
gccctgctcg agcacctgct gaagcaaccg gagccgcagc gggcggaacg cgcggcggga    9720
ttccacgaga tggccatcgg ctacgcctga acccttgacc tgcgaagacc cggcctggcc    9780
gggctttgcg gttgcataac gcacggagta gcaccatgca cgccatcctc atcgccatcg    9840
gctcggccgg cgacgtattt cccttcatcg gcctggcccg gaccctgaaa ttgcgcgggc    9900
accgcgtgag cctctgcacc atcccggtgt tcgcgacgc ggtggagcag cacggcatcg    9960
cgttcgtccc gctgagcgac gaactgacct accgccggac catgggcgat ccgcgcctgt   10020
gggaccccaa gacgtccttc ggcgtgctct ggcaaaccat cgccgggatg atcgagccgg   10080
tctacgagta cgtctcggcg cagcgccatg acgacatcgt ggtggtcggc tcgctctggg   10140
cgctgggcgc acgcatcgct cacgagaagt acgggattcc ctacctgtcc gcgcaggtct   10200
cgccatcgac cttgttgtcg gcgcacctgc cgccggtaca ccccaagttc aacgtgcccg   10260
agcagatgcc gctggcgatg cgcaagctgc tctggcgctg catcgagcgc ttcaagctgg   10320
atcgcacctg cgcgccggat atcaacgcgg tgcggcgcaa ggtcggcctg gagacgccgg   10380
tgaagcgcat cttcacccaa tggatgcatt cgccgcaggg cgtggtctgc ctgttcccgg   10440
cctggttcgc gccgccccag caggattggc cgcaacccct gcacatgacc ggcttcccgc   10500
tgttcgacgg cagtatcccg ggacccccgc tcgacgacga actgcaacgc tttctcgatc   10560
agggcagccg gccgctggtg ttcacccagg gctcgaccga acacctgcag gcgacttct   10620
acgccatggc cctgcgcgcg ctggaacgcc tcggcgcgcg tgggatcttc ctcaccggcg   10680
ccggccagga accgctgcgc ggcttgccga accacgtgct gcagcgcgcc tacgcgccac   10740
tgggagcctt gctgccatcg tgcgccgggc tggtccatcc gggcggtatc ggcgccatga   10800
```

```
gcctggcctt ggcggcgggg gtgccgcagg tgctgctgcc ctgcgcccac gaccagttcg    10860
acaatgccga acggctggtc cggctcggct gcgggatgcg cctgggcgtg ccattgcgcg    10920
agcaggagtt gcgcggggcg ctgtggcgct tgctcgagga cccggccatg gcggcggcct    10980
gtcggcgttt catggaattg tcacaaccgc acagtatcgc ttgcggtaaa gcggcccagg    11040
tggtcgaacg ttgtcatagg gagggggatg cgcgatggct gaaggctgcg tcctgaccta    11100
cgggagaaga acgatctcgg cgaaacgcat tccctctaga gtttaaacac caggtgcgat    11160
cgcgcggccg cgctcgagca cgcgagagta gggaactgcc aggcatcaaa taaaacgaaa    11220
ggctcagtcg aaagactggg cctttcgttt tatctgttgt ttgtcggtga acgctctcct    11280
gagtaggaca aatccgccgg gagcggattt gaacgatgat aagctgtcaa acatgagaat    11340
tcttgaagac gaaagggcct cgtgtgtaca ataatatttg cccatggatt taaataaccc    11400
tatgctactc cgtcaagccg tcaattgtct gattcgttac caattatgac aacttgacgg    11460
ctacatcatt cacttttcct tcacaaccgg cacggaactc gctcgggctg gccccggtgc    11520 atttttaaa tacccgcgag aaatagagtt gatcgtcaaa accaacattg cgaccgacgg    11580
tggcgatagg catccgggtg gtgctcaaaa gcagcttcgc ctggctgata cgttggtcct    11640
cgcgccagct taagacgcta atccctaact gctggcggaa aagatgtgac agacgcgacg    11700
gcgacaagca acatgctgt gcgacgctgg cgatatcaaa attgctgtct gccaggtgat    11760
cgctgatgta ctgacaagcc tcgcgtaccc gattatccat cggtggatgg agcgactcgt    11820
taatcgcttc catgcgccgc agtaacaatt gctcaagcag atttatcgcc agcagctccg    11880
aatagcgccc ttccccttgc ccggcgttaa tgatttgccc aaacaggtcg ctgaaatgcg    11940
gctggtgcgc ttcatccggg cgaaagaacc ccgtattggc aaatattgac ggccagttaa    12000
gccattcatg ccagtaggcg cgcggacgaa agtaaaccca ctggtgatac cattcgcgag    12060
cctccggatg acgaccgtag tgatgaatct ctcctggcgg gaacagcaaa atatcacccg    12120
gtcggcaaac aaattctcgt ccctgatttt tcaccacccc ctgaccgcga atggtgagat    12180
tgagaatata acctttcatt cccagcggtc ggtcgataaa aaaatcgaga taaccgttgg    12240
cctcaatcgg cgttaaaccc gccaccagat gggcattaaa cgagtatccc ggcagcaggg    12300
gatcattttg cgcttcagcc atacttttca tactcccgcc attcagagaa gaaaccaatt    12360
gtccatattg catcagacat tgccgtcact gcgtctttta ctggctcttc tcgctaacca    12420
aaccggtaac cccgcttatt aaaagcattc tgtaacaaag cgggaccaaa gccatgacaa    12480
aaacgcgtaa caaaagtgtc tataatcacg gcagaaaagt ccacattgat tatttgcacg    12540
gcgtcacact ttgctatgcc atagcatttt tatccataag attagcggat cctacctgac    12600
gctttttatc gcaactctct actgtttctc cataccccgat ttaaatgaat tcccttggga    12660
ctcttaatta acaggaggag gtatgactca tgacgattct cgtgaccggc agcgccggct    12720
tcatcggcgc caatttcgtg ctcgactggc tggccctgca tgacgagccg gtggtcagcc    12780
tcgacaagct cacctacgcc ggcaaccggc agaacctcgc cagcctcgac ggcgacgccc    12840
ggcacacctt cgtcgccggc gatatcggcg ataggcagct ggtagcccgc ctgctcgccg    12900
agcaccagcc gcgggcgatc ctcaacttcg ccgcggaatc ccatgtggac cgctcgatcc    12960
acggccccga ggacttcatc cagaccaaca tcgtcggcac cttccgcctg ctggaagaag    13020
tgcgcgccta ctgggcgcg ctggagccgg aagcgaaggc ggcattccgc ttcctccacg    13080
tctccaccga cgaagtctat ggctcgctgg caccgagcga tccggccttc accgagaaca    13140
accgctacga gccgaacagt ccctactcgg cgtccaaggc ggcctccgac cacctagtgc    13200
```

```
gggcctatca ccacacctat gggctgccgg tgctgaccac caactgctcg aacaactacg    13260
gcccgtacca cttcccggaa aagctcatcc cactggtgat ccacaacgcc ctggccggca    13320
agccgctgcc gatctacggc gacggccagc agatccgcga ctggctctac gtcaaggacc    13380
attgcagcgc catccgccgg gtcctcgaag ccgggcaact gggcgagacc tacaatgtcg    13440
gcggctggaa cgaaaaggcc aacctcgacg tggtcgagac cctctgcgcc atcctcgacc    13500
aggagcagcc gcgcgccgac ggccgcagct atcgcgagca gatcaccttc gtcaaggatc    13560
gtccgggcca tgatcgccgc tacgccatcg atgccacgcg cctggagcgc gagctgggct    13620
ggaagccggc ggaaaccttc gagaccggca tccgcaagac cgtgcgctgg tacctggaca    13680
accaggactg ggtggccaac gtaaccagcg gtgcctaccg cgagtgggtg ggtaagcagt    13740
acgcatgaac cggatccttc tcctcggcgc caacggccag gtcggctggg agctgcagcg    13800
cgccctggcg ccgctgggcg aactgctggt ctgtgaccgt cggcgcgccg atctcgccga    13860
ccccgaaggc ctggcgcgac tggttcgcgc cgagcggccg cagttcatcg tcaacgccgg    13920
tgcctacacc gcggtggaca aggccgagag cgatgccgac aacgcccgcc tgatcaatgc    13980
ccgcgccgtc gcggtactgg ccgaggaggc gcggcctgc ggcgcctggc tggtgcatta    14040
ctccaccgac tacgtgttcg acggcgcggg cagcgtgcct ttcgccgagg acgcgccgac    14100
cggcccgctg agcgtctacg gcagaccaa gctggaaggc gagcaggcca tccgcgccag    14160
cggctgccgc cacctgatct tccgcaccag ctgggtctac gccgcgcgcg cggaaacttt    14220
cgccaagacc atgctgcgcc tggccgggca acgcgacgaa ctcaaggtcg tggccgacca    14280
gttcggcgcg cccaccagcg ccgagctgat cgccgacgtc accgcccagg ccctgcagcg    14340
cctgtgctgg gatgtcgagc tggcagcacg ggccagcggc acctaccacc tggtcgccag    14400
cggcgagacg tcctggcacc tctatgcgcg cttcgtcatc gaacaggcgc tggagcgggg    14460
ctgggagttg caggcgacgc cgcagcgggt cctgccgatc gccaccgagg actacccggt    14520
gccggcgaag cgtccggcca attcgcgcct cgacaaccgc aagctgcaac aggtcttcgg    14580
cctggtactg ccagactggc gctaccatgc cggacgcatg atccaggaac tgagcgagca    14640
gggaccacta tgaaacgcaa gggcatcatc ctcgccggag gctcgggcac ccgcctgcac    14700
ccggcaacgc tggccatctc caagcagttg ctgccggtgt acgacaagcc gatgatctac    14760
tacccgctca gtaccctgat gctggcgggc atcgcgaga tactgatcat ctcgaccccca    14820
caggacaccc cacgcttcca gcagttgctg ggcgacggtt cgaactgggg cctggacctg    14880
caatatgccg tgcaaccgtc gccggacggc ctggcccagg ccttcctgat cggcgagtcg    14940
ttcatcggca acgacctcag cgcgctggtc ctgggcgaca acctctatta cggccacgac    15000
ttccacgagt tgctcggcag cgcttcgcag cgccagaccg gcgccagtgt cttcgcctac    15060
cacgtgctgg acccggagcg ctacggcgtg gtcgagttcg accagggcgg caaggccatc    15120
agcctggaag agaagccact ggagccgaag tcgaactacg cggtcaccgg cctgtatttc    15180
tacgaccagc aggtggtgga catcgccagg gacctgaagc cttcgccgcg cggcgagctg    15240
gagatcaccg acgtcaaccg cgcctatctg gagcgcggcc agctcagcgt ggagatcatg    15300
ggccgcggct acgcctggct ggataccggc acccacgatt cgctgctcga ggccggccag    15360
ttcatcgcca ccctggagaa ccgccagggt ctcaaggtgg cctgcccgga agagatcgcc    15420
taccggcaga agtggatcga cgccgcgcaa ctggaaaaac tcgccgcgcc gctgccaag    15480
aacggctacg gccaatacct caagcgcctg ctgaccgaga ccgtgtactg atgaaagcga    15540
```

```
cccgctggc aattcccgac gtcatcctct tcgaaccccg ggtgttcggc gacgatcgcg   15600
gattcttctt cgaaagctac aaccagcgcg ccttcgagga agcctgcggt catccggtca   15660
gcttcgtcca ggacaaccat tcgcgttccg cccgtggcgt cctccgcggc ctgcactacc   15720
agatccggca agcccaggga aaactggtgc gcgccactct cggcgaggta ttcgacgtgg   15780
ccgtcgacct gcgtcgcggc tcgccgacct tcggccagtg ggtaggcgaa cgcctgagcg   15840
cggagaacaa gcgccagatg tggattccgg ccggcttcgc gcacggcttc gtggtgctca   15900
gcgaatacgc cgagttcctc tacaagacca ccgacttctg ggcgccggaa cacgaacgct   15960
gcatcgtctg gaacgatccc gagctgaaga tcgactggcc gctgcaggat gccccctgc    16020 tttcggagaa ggaccgccag ggcaaggcat tcgccgacgc cgactgcttc ccctgaacgg   16080
cagggagcga ccggactcgg cgcaaggcgt ggtaatttag ggtttaaaca ccaggtgcga   16140
tcgcgcggcc gcgctcgagc acgcgagagt agggaactgc caggcatcaa ataaaacgaa   16200
aggctcagtc gaaagactgg gcctttcgtt ttatctgttg tttgtcggtg aacgctctcc   16260
tgagtaggac aaatccgccg ggagcggatt tgaacgatga taagctgtca aacatgagaa   16320
ttcttgaact agttgtacaa acgttcgtca aaagggcga                          16359
```